United States Patent
Zhou et al.

(10) Patent No.: US 10,280,408 B2
(45) Date of Patent: May 7, 2019

(54) METHOD OF SUPPRESSING GENE TRANSCRIPTION THROUGH HISTONE LYSINE METHYLATION

(71) Applicant: ICAHN SCHOOL OF MEDICINE AT MOUNT SINAI, New York, NY (US)

(72) Inventors: Ming-ming Zhou, Old Greenwich, CT (US); Shiraz Mujtaba, New York, NY (US)

(73) Assignee: ICAHN SCHOOL OF MEDICINE AT MOUNT SINAI, New York, NY (US)

(*) Notice: Subject to any disclaimer, the term of this patent is extended or adjusted under 35 U.S.C. 154(b) by 78 days.

(21) Appl. No.: 15/003,174

(22) Filed: Jan. 21, 2016

(65) Prior Publication Data

US 2016/0137989 A1   May 19, 2016

Related U.S. Application Data

(60) Division of application No. 12/896,510, filed on Oct. 1, 2010, now Pat. No. 9,249,190, which is a continuation of application No. PCT/US2009/039187, filed on Apr. 1, 2009.

(60) Provisional application No. 61/041,563, filed on Apr. 1, 2008.

(51) Int. Cl.
| | |
|---|---|
| A61K 38/00 | (2006.01) |
| C12N 9/10 | (2006.01) |
| A61K 38/43 | (2006.01) |
| C07K 14/005 | (2006.01) |
| A61K 48/00 | (2006.01) |

(52) U.S. Cl.
CPC ............ *C12N 9/1007* (2013.01); *A61K 38/43* (2013.01); *C07K 14/005* (2013.01); *A61K 38/00* (2013.01); *A61K 48/00* (2013.01); *C07K 2319/09* (2013.01); *C12N 2710/00022* (2013.01); *C12N 2710/10343* (2013.01); *C12N 2740/15043* (2013.01); *C12Y 201/01043* (2013.01)

(58) Field of Classification Search
None
See application file for complete search history.

(56) References Cited

U.S. PATENT DOCUMENTS

| 2004/0241756 A1 | 12/2004 | Kouzarides et al. |
| 2006/0009408 A1 | 1/2006 | Davidson et al. |
| 2007/0196373 A1 | 8/2007 | Le et al. |
| 2008/0063701 A1 | 3/2008 | Keller et al. |

OTHER PUBLICATIONS

U.S. Appl. No. 12/896,510 (now U.S. Pat. No. 9,249,190), filed Oct. 1, 2010 (Feb. 2, 2016).
U.S. Appl. No. 12/896,510, Dec. 17, 2015 Issue Fee Payment.
U.S. Appl. No. 12/896,510, Sep. 18, 2015 Notice of Allowance.
U.S. Appl. No. 12/896,510, Oct. 28, 2014 Amendment and Request for Continued Examination (RCE).
U.S. Appl. No. 12/896,510, Jul. 29, 2014 Final Office Action.
U.S. Appl. No. 12/896,510, Apr. 7, 2014 Response to Non-Final Office Action.
U.S. Appl. No. 12/896,510, Dec. 6, 2013 Non-Final Office Action.
U.S. Appl. No. 12/896,510, Mar. 1, 2012 Response to Restriction Requirement.
U.S. Appl. No. 12/896,510, Dec. 1, 2011 Restriction Requirement Filed.
"CCAAT displacement protein/cut homolog recruits G9a histone lysine methyltransferase to repress transcription," Nishio & Walsh, PNAS 101(31):11257-11262 (Aug. 3, 2004).
Ard et al., "Transcriptional Regulation of the mdm2 Oncogene by p53 Requires TRRAP Acetyltransferase Complexes," *Molecular and Cellular Biology*, 22(16):5650-5661 (2002).
De Santa et al., "Histone H3 Lysine-27 Demethylase Jmjd3 Links Inflammation to Inhibition of Polycomb-Mediated Gene Silencing," Cell 130:1083-1094 (2007).
Imamura et al., "Cellular Localization of the Signaling Components of *Arabidopsis* His-to-Asp Phosphorelay," Biosci Biotechnol Biochem 65(9):2113-2117 (2001).
International Search Report and Written Opinion for PCT/US2009/039187, dated Oct. 22, 2009.
Li et al., "Analysis of 74 kb of DNA Located at the Right End of the 330-kb Chlorella Virus PBCV-1 Genome," Virology 237:360-377 (1997).
Manzur et al., "A dimeric viral SET domain methyltransferase specific to Lys27 of histone H3," Nature Structural Biology 10(3):187-196 (Mar. 2003).
Marzio et al., "HIV-1 Tat Transactivator Recruits p300 and CREB-Binding Protein Histone Acetyltransferases to the Viral Promoter," *PNAS*, 95(23):13519-13524 (1998).
Orian et al., "Genomic Binding by the *Drosophila* Nyc, Max, Mad/Mnt Transcription Factor Network," *Genes & Development*, 17(9): 1101-1114 (2003).
Peinado et al., "Transcriptional Regulation of Cadherins During Development and Carcinogenesis," *The International Journal of Developmental Biology*, 48:365-375 (2004).

(Continued)

*Primary Examiner* — Catherine S Hibbert
(74) *Attorney, Agent, or Firm* — Baker Botts L.L.P.

(57) ABSTRACT

The present invention relates to methods of suppressing the transcriptional expression of one or more genes by methylating the chromatin histone proteins of the one or more genes. Specifically, a viral SET domain histone lysine mehtyltransferase (vSET or vSET-like protein) methylates lysine 27 of a gene's histone protein 3 (H3-K27) thereby suppressing the transcription of the gene.

17 Claims, 32 Drawing Sheets
Specification includes a Sequence Listing.

(56) References Cited

OTHER PUBLICATIONS

Qian et al., "SET domain protein lysine methyltransferase: Structure, Specificity and Catalysis," Cell Mol Life Sci pp. 1-9 (2006).
Yamamoto et al., "Histone H3 Phosphorylation by IKK-α is Critical for Cytokine-Induced Gene Expression," *Nature*, 423(6940):655-659 (2003).

|  | 4 | 9 | 27 | 36 | | |
|---|---|---|---|---|---|---|
| Chlorella NC64A (1-70) | ARTKQTARKS | TGGKAPRKQL | ATKAARKSAP | ATGGVKKPHR | YRPGTVALRE | IRKYQKSTEL LIRKLPFQRL |
| H. sapien | ARTKQTARKS | TGGKAPRKQL | ATKAARKSAP | ATGGVKKPHR | YRPGTVALRE | IRRYQKSTEL LIRKLPFQRL |
| M. musculus | ARTKQTARKS | TGGKAPRKQL | ATKAARKSAP | ATGGVKKPHR | YRPGTVALRE | IRRYQKSTEL LIRKLPFQRL |
| X. laevis | ARTKQTARKS | TGGKAPRKQL | ATKAARKSAP | ATGGVKKPHR | YRPGTVALRE | IRRYQKSTEL LIRKLPFQRL |
| C. elegans | ARTKQTARKS | TGGKAPRKQL | ATKAARKSAP | ASGGVKKPHR | YRPCTVALRE | IRRYQKSTEL LIRRAPFQRL |
| C. reinhardtii | ARTKQTARKS | TGGKAPRKQL | ATKAARKT-P | ATGGVKKPHR | YRPGTVALRE | IRKYQKSTEL LIRKLPFQRL |

|  |  |  |  |  |  |  |
|---|---|---|---|---|---|---|
| Chlorella NC64A (71-135) | VREIAQDFKT | DLRFQSSAVL | ALQEAEAYL | VGLFEDTNLC | AIHAKRVTIM | PKDIQLARRI RGERA (SEQ ID NO:10) |
| H. sapien | VREIAQDFKT | DLRFQSSAVM | ALQEACEAYL | VGLFEDTNLC | AIHAKRVTIM | PKDIQLARRI RGERA (SEQ ID NO:11) |
| M. musculus | VREIAQDFKT | DLRFQSSAVM | ALQEACEAYL | VGLFEDTNLC | AIHAKRVTIM | PKDIQLARRI RGERA (SEQ ID NO:12) |
| X. laevis | VREIAQDFKT | DLRFQSSAVM | ALQEASEAYL | VGLFEDTNLC | GIHAKRVTIM | PKDIQLARRI RGERA (SEQ ID NO:13) |
| C. elegans | VREIAQDFKT | DLRFQSSAVM | ALQEAEAYL | VGLFEDTNLC | AIHAKRVTIM | PKDIQLARRI RGERA (SEQ ID NO:14) |
| C. reinhardtii | VREIAQDFKT | DLRFQSQAVV | ALQEAEAYL | VGLFEDTNLC | AITAKRVTIM | PKDIQLARRI RGERA (SEQ ID NO:15) |

FIG. 2a

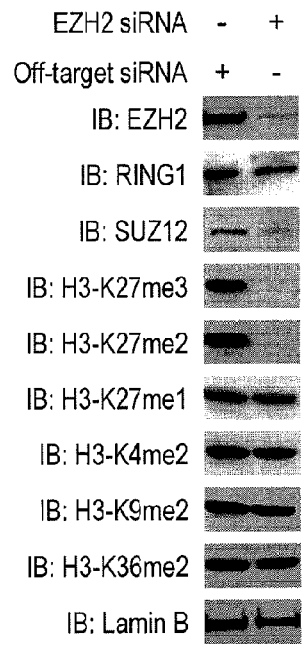
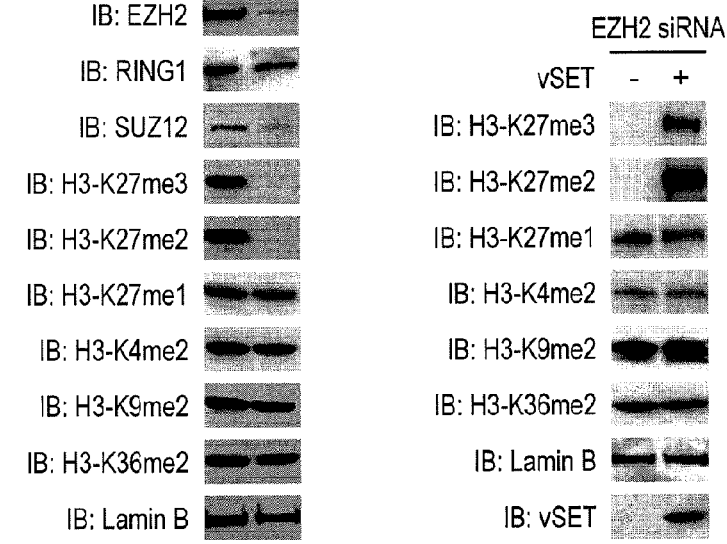
FIG.3b    FIG.3c
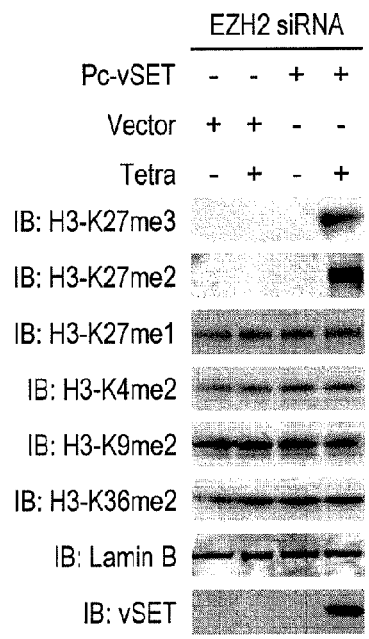
FIG.3d

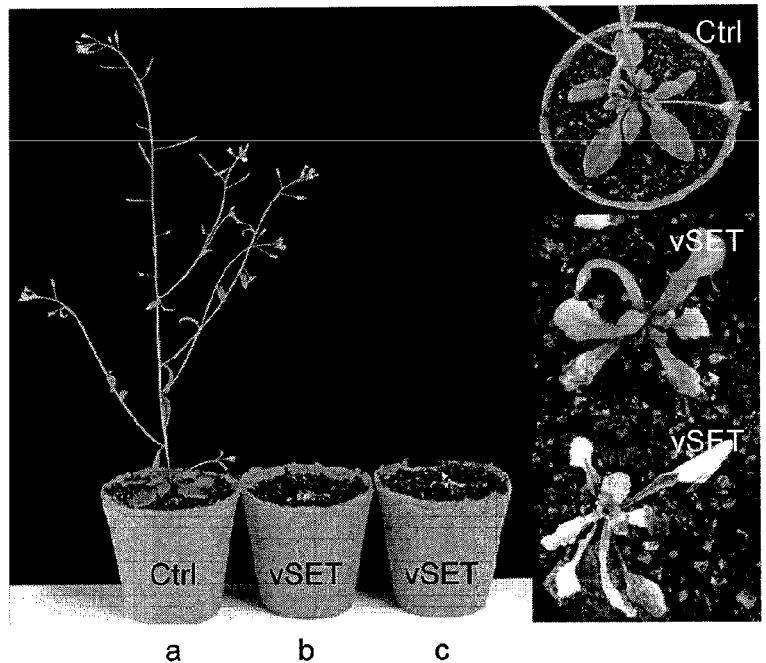

FIG.8

Nucleotides 293003-293362 of GenBank Accession number NC_000852 (SEQ ID NO:1)

TTAATTTTGTGTTAATCTAGGTCTAGACAACCAGTAGTCATCGCCATAACTTATCGTT
ATTTCTTCACCGATGGCTATTGGTTTTATGGTGAATATCCGCATGCGCTTGAGACCTG
CTGTCAGTTCATGTCTAGCGTTAGGGTCTTTGCTATGGTTAAAAATTGCACCAAAAC
CAAGAGCCATTGCAGACATATTCTTTCTCGAAAACAAATAATCTTCAAGGGCGGTCC
CCCAATCATCATTATGGCGCACTATACACAAACATTCTTCAACAAGTTCTCCCTTCTC
GAAAGATTTTCTCGCAAATACACCATATCCACCCAATGGGGATTTTTTTCACGATGAC
TCTGTCATTAAACAT

FIG.9

GenBank accession number AAC96946 (SEQ ID NO:2)

MFNDRVIVKKSPLGGYGVFARKSFEKGELVEECLCIVRHNDDWGTALEDY
LFSRKNMSAMALGFGAIFNHSKDPNARHELTAGLKRMRIFTIKPIAIGEE
ITISYGDDYWLSRPRLTQN

FIG.10

Table S1. Antibodies used in the study

| Antibody | Company Name | Catalogue # | IB(Conc) | Dot Blot | Lot# | ChIP (conc.) | Lot# | Dot Blot |
|---|---|---|---|---|---|---|---|---|
| H3 | Upstate/ABCAM | 05-499 / ab1791 | 0.5 µg/ml | | 31560 | 2 µg/tube | 295428 | |
| H3K27me1 | Upstate | 07-448 | 0.1 µg/ml | 0.5 µg/ml | JBC1361682 | 5 µg/tube | JBC1361682 | |
| H3K27me2 | Upstate/ABCAM | 07-452 / ab24684 | 0.2 µg/ml | 1.0 µg/ml | 32539 | 5 µg/tube | 383109 | 1.0 µg/ml |
| H3K27me3 | Upstate/ABCAM | 07-449 / ab6002 | 0.4 µg/ml | 2.0 µg/ml | 701050758 | 5 µg/tube | 367420 | 2.0 µg/ml |
| H3K4me2 | Upstate | 05-790 | 0.4 µg/ml | | 26855 | | | |
| H3K9me2 | Upstate | 06-768 | 0.4 µg/ml | | 32324 | | | |
| H3K36me2 | Upstate | 07-274 | 0.4 µg/ml | | 31553 | | | |
| H3K27ac | Upstate | 07-360 | 0.4 µg/ml | | | | | |
| H3S28p | Upstate | 07-145 | 0.4 µg/ml | | | | | |
| Acetyl-Histone H3* | Upstate | 06-599b | 0.5 µg/ml | | JBC136109* | 5 µg/tube | | |
| Pan-Lysine Methylated | ABCAM | AB7315 and AB23366 | | | | | | |
| Rabbit IgG* | Upstate | PP64b | | | JBC136109* | 5 µg/tube | | |
| Lamin B | Santa Cruz | Sc-6216 | 1.0 µg/ml | | L0506 | | | |
| EZH2 | Cell Signalling | 4095 | 2.0 µg/ml | | 3 | | | |
| CBX4 | Aviva System Biology | ARP30002_P050 | 0.5 µg/ml | | QC1928 | 5 µg/tube | QC1928 | |
| CBX7 | ABCAM | ab21873 | 0.5 µg/ml | | 376629 | 5 µg/tube | 376629 | |
| CBX8 | Aviva System Biology | ARP34600_P050 | 0.5 µg/ml | | QC3996 | 5 µg/tube | QC3996 | |
| SUZ12 | ABCAM | ab12073 | 0.5 µg/ml | | 223004 | 5 µg/tube | 223004 | |
| BMI1 | ABCAM | ab14389 | 0.5 µg/ml | | 422822 | 5 µg/tube | 422822 | |
| Flag | Sigma | F-3165 | 10 µg/ml | | 086K5012 | | | |
| GFP | Clontech | 8371-1 | 1.0 µg/ml | | | | | |

FIG. 15

Table S2. Amino Acid Sequences of Histone H3 Peptides (aa 1-57) used in Figure.2C

| Name | H3 Sequences (aa 1-57) |
|---|---|
| Wild Type | ARTKQTARKSTGGKAPRKQLATKAARKSAPSTGGVKKPHRYRPGTVALREIRRYQKS (SEQ ID NO:23) |
| 5R | ARTRQTARRSTGGKAPRKQLATKAARRSAPSTGGVRRKPHRYRPGTVALREIRRYQKS (SEQ ID NO:24) |
| K27/K4R/K9R | ARTRQTARRSTGGKAPRKQLATKAARKSAPSTGGVKKPHRYRPGTVALREIRRYQKS (SEQ ID NO:25) |
| K27/4R | ARTRQTARRSTGGKAPRKQLATKAARRSAPSTGGVRRPHRYRPGTVALREIRRYQKS (SEQ ID NO:26) |
| K36/4R | ARTRQTARRSTGGKAPRKQLATKAARKSAPSTGGVRRKPHRYRPGTVALREIRRYQKS (SEQ ID NO:27) |
| K37/4R | ARTRQTARRSTGGKAPRKQLATKAARRSAPSTGGVRKPHRYRPGTVALREIRRYQKS (SEQ ID NO:28) |
| K27R/K36R | ARTKQTARKSTGGKAPRKQLATKAARRSAPSTGGVRKPHRYRPGTVALREIRRYQKS (SEQ ID NO:29) |
| K36/K37/3R | ARTRQTARRSTGGKAPRKQLATKAARKSAPSTGGVRRKPHRYRPGTVALREIRRYQKS (SEQ ID NO:30) |
| K27/K37/3R | ARTRQTARRSTGGKAPRKQLATKAARRSAPSTGGVRKPHRYRPGTVALREIRRYQKS (SEQ ID NO:31) |
| K27R | ARTKQTARKSTGGKAPRKQLATKAARRSAPSTGGVKKPHRYRPGTVALREIRRYQKS (SEQ ID NO:32) |

Note: Lysine to arginine mutation sites are indicated by a • beneath the arginine.

FIG. 16

Table S3. Sequences of siRNAs used for Human EZH2 Knockdown

| No. | Sense Strand | Anti-Sense Strand |
|---|---|---|
| 1 | GAGGACGGAUUCCCAAUAAUU (SEQ ID NO:33) | 5' – P.UUAUUGGGAAGCCGUCCUCUU (SEQ ID NO:37) |
| 2 | GCUGAAGCCUCAAUGUUUAUU (SEQ ID NO:34) | 5' – P.UAAACAUUGAGGCUUCAGCUU (SEQ ID NO:38) |
| 3 | UAACGGUGAUCACAGGAUAUU (SEQ ID NO:35) | 5' – P.UAUCCUGUGAUCACCGUUAUU (SEQ ID NO:39) |
| 4 | GCAAUUCUCGGUGUCAAAUU (SEQ ID NO:36) | 5' – P.UUUGACACCGAGAAUUGCUU (SEQ ID NO:40) |

FIG. 16 (Cont'd)

Table S4. List of RTPCR[1] and ChIP[2] Primers used in this study

| | Gene | Sense strand | | TM (°C) | Antisense strand | | TM (°C) | Size |
|---|---|---|---|---|---|---|---|---|
| 1 | HOXA7 | CAAAATGCCCAGCCCACTTT | (SEQ ID NO:41) | 54.6 | TAGCCCGCACGCAAAGGG | (SEQ ID NO:42) | 55.8 | 146 |
| 2 | HOXA9 | CAGCCAACTGGCTTCATGGG | (SEQ ID NO:43) | 59.5 | CACTCGTCTTTGCTCGGTC | (SEQ ID NO:44) | 57.5 | 229 |
| 3 | HOXB9 | AACTGCTGCACGCTCGGT | (SEQ ID NO:45) | 59 | TCACATTACTCTTTGCCCTG | (SEQ ID NO:46) | 53.4 | 227 |
| 4 | HOXD8 | CGATACGATAACTTACAGAGAC | (SEQ ID NO:47) | 54 | TAGAGTTTGGAAGCGACTGT | (SEQ ID NO:48) | 53.4 | 219 |
| 5 | GAPDH | TGCAACACCAACTGCTTACC | (SEQ ID NO:49) | 55.4 | GGCATGGCACTGTGGTCATGAC | (SEQ ID NO:50) | 59.7 | 87 |
| 6 | HEY1 | 5'-GAGCCGGGCCGCTGTAGTTA-3' | (SEQ ID NO:51) | 56 | 5'-GGGGTGCGCGTCAAAGTA-3' | (SEQ ID NO:52) | 56 | 340 |

References:
1. Chen, K.N., et al., Expression of 11 HOX genes is deregulated in esophageal squamous cell carcinoma. *Clin Cancer Res*, 11, 1044–9 (2005).
2. De Santa, F., et al, The histone H3 lysine-27 demethylase Jmjd3 links inflammation to inhibition of polycomb-mediated gene silencing. *Cell*, 130, 1083–94 (2007).

FIG. 16 (Cont'd)

METHOD OF SUPPRESSING GENE TRANSCRIPTION THROUGH HISTONE LYSINE METHYLATION

CROSS-REFERENCE TO RELATED APPLICATIONS

The present application is a divisional of, and claims priority to, U.S. patent application Ser. No. 12/896,510, filed Oct. 1, 2010, which is a continuation of International Application No. PCT/US2009/039187, filed Apr. 1, 2009, which claims the benefit of priority to U.S. Provisional Application No. 61/041,563, filed Apr. 1, 2008, priority to each of which is claimed, and the contents of each of which are hereby incorporated by reference in their entireties.

GRANT INFORMATION

The invention was made with government support under grant numbers GM073207 and CA087658 awarded by the National Institutes of Health. The government has certain rights in the invention.

FIELD OF THE INVENTION

The present invention relates to methods of suppressing the transcriptional expression of one or more genes by methylating chromatin histone proteins. Specifically, a viral SET domain histone lysine methyltransferase (vSET or vSET-like protein) methylates lysine 27 of a gene's histone protein 3 (H3-K27), thereby suppressing the transcription of a gene or genes.

SEQUENCE LISTING

The specification further incorporates by reference the Sequence Listing submitted herewith via EFS on Jan. 13, 2017. Pursuant to 37 C.F.R. § 1.52(e)(5), the Sequence Listing text file, identified as Sequence_Listing.txt, is 26,135 bytes and was created on Jan. 13, 2017. The Sequence Listing, electronically filed herewith, does not extend beyond the scope of the specification and thus does not contain new matter.

BACKGROUND

Position-specific modifications of histones provide epigenetic control of gene expression and silencing in eukaryotes (Nightingale et al., Curr Opin Genet Dev 16, 125-36 (2006); Fischle et al., Curr Opin Cell Biol 15, 172-83 (2003)). Such modifications include acetylation, methylation, phosphorylation and ubiquitination (Id.). Viruses recruit chromatin-associated transcriptional proteins for their genome maintenance and replication. For instance, the papillomavirus E2 protein binds Brd4 to tether the viral genome to mitotic chromosomes to ensure persistence of viral episomes in viral infected cells (You et al., Cell 117, 349-60 (2004); Wu et al., Genes Dev 20, 2383-96 (2006)). The adenovirus E1A protein interacts with the retinoblastoma protein p130 to disrupt a network of protein interactions required for silencing of E2F-responsive genes in quiescent cells (Ghosh et al., Mol Cell 12, 255-60 (2003)). Moreover, the trans-activator Tat from human immunodeficiency virus recruits the histone acetyltransferases p300/CBP (CREB binding protein) and PCAF (p300/CBP associated factor) for lysine acetylation of a nucleosome, a remodeling step required for transcriptional activation and replication of the integrated provirus (Mujtaba et al., Mol Cell 9, 575-86 (2002); Don et al., EMBO J 21, 2715-23 (2002)). Despite the indirect virus/host protein recruitment mechanisms to reconfigure chromatin structure for viral transcription, no viral enzymes have been reported that directly modify histones and modulate host gene transcription. Histone lysine methylation, except for H3-K79, is catalyzed by a family of SET domain proteins first identified in *Drosophila* proteins: Suppressor of variegation, Enhancer of zeste (E(z)) and Trithorax. (Bannister et al., Cell 109, 801-6 (2002); Lachner et al., J Cell Sci 116, 2117-24 (2003)). Position- and state-specific histone lysine methylation by SET domain proteins in a specific biological context specifies unique functional consequences (Bannister et al. and Lachner et al.). For instance, during cell proliferation, H3-K4 di-methylation by Set1 correlates with basal transcription, whereas H3-K4 tri-methylation occurs at fully activated promoters (Sims et al., Genes Dev 20, 2779-86 (2006); Wysocka et al., Nature 442, 86-90 (2006); Bernstein et al., Proc Natl Acad Sci USA 99, 8695-700 (2002)). Regional H3-K9 tri-methylation by Suv39h at transcriptionally inert chromatin domains is a hallmark of constitutive hetero-chromatin (Peters et al., Nat Genet 30, 77-80 (2002)). During cell differentiation, extended H3-K27 di- and tri-methylation by the *Drosophila* Polycomb group (PcG) Esc-E(z) complex or the mammalian counterpart Eed-Ezh2 complex are linked to Hox gene silencing, X-chromosome inactivation, germline development and stem cell pluripotency, as well as cancer (Czermin, B. et al. Cell 111, 185-196 (2002); Muller, J. et al., Cell 111, 197-208 (2002); Cao et al. Science 298, 1039-1043 (2002); Kuzmichev et al., Genes Dev 16, 2893-905 (2002); Plath et al. Science 300, 131-5 (2003); Boggs et al., Nat Genet 30, 73-6 (2002); Bernstein et al. Cell 125, 315-26 (2006); Boyer et al., Nature 441, 349-53 (2006); Lee et al. Cell 125, 301-13 (2006); Cao & Zhang, Curr Opin Genet Dev 14, 155-64 (2004)).

The high degree of modification complexity and coding potential of histone lysine methylation in epigenetic control may explain the existence of an unusually large family of SET domain proteins with more than 700 members (Schultz et al., Proc. Natl. Acad. Sci. U.S.A. 95, 5857-5864 (1998)). Notably, within this extensive family is a small subclass of SET domain proteins encoded by viruses and bacteria of which little is known about their cellular functions. One of these viral proteins is the SET domain protein (vSET) encoded by *Paramecium bursaria chlorella* virus 1 (PBCV-1) which specifically methylates Lys27 in histone 3, a modification implicated in gene silencing (Manzur et al., Nat Struct Biol., 10:187-196). PBCV-1 is the prototype of a family of large, icosahedral, double-stranded DNA—containing viruses that are known to replicate in certain unicellular, eukaryotic *chlorella*-like green algae, particularly zoochlorellae (Van Etten et al., Annu. Rev. Microbiol. 53, 447-494 (1999)). DNA sequence analysis of PBCV-1 reveals that this giant virus contains a large 330 kb genome of 376 protein-encoding genes (Li et al. Virology 237, 360-377 (1997)). The SET domain-containing PBCV-1 protein consists of 119 amino acids and represents the smallest known SET domain—containing protein in the SET domain family, although vSET lacks the cysteine-rich pre-SET and post-SET motifs flanking the conserved core SET domain. These pre-SET and post-SET motifs are required for histone methyltransferase activity in various SET domain proteins including human SUV39H1 (Rea et al. Nature 406, 593-599 (2000)). The presence of SET domain-like proteins in viruses raises questions about whether such proteins have histone modifying activities, and if so, what are the cellular consequences when these proteins are expressed in vivo (Qian & Zhou, Cell Mol Life Sci 63, 2755-63 (2006); Manzur et al., FEBS Lett 579, 3859-65 (2005); Alvarez-Venegas et al., Mol Biol Evol 24, 482-97 (2007)).

SUMMARY OF THE INVENTION

The present invention provides a method for selective or general suppression or inhibition of gene expression. Specifically, the present invention provides a method of suppressing the transcriptional expression of a targeted gene in a cell by introducing into the cell a protein that methylates a chromatin histone protein of the targeted gene.

In non-limiting embodiments, the chromatin histone protein is the histone 3 protein (H3). In a specific non-limiting embodiment, lysine 27 of H3 is methylated (H3-K27).

In non-limiting embodiments, the introduced protein comprises a lysine methyltransferase.

In particular non-limiting embodiments, the lysine methyltransferase is a histone lysine methyltransferase.

In particular non-limiting embodiments, the lysine methyltransferase is a viral histone lysine methyltransferase.

In preferred specific non-limiting embodiments, the lysine methyltransferase comprises a *Chlorella* virus SET domain of a viral histone lysine methyltransferase protein.

In particular non-limiting embodiments, the present invention provides a method for suppressing/inhibiting expression of a specific targeted gene in a cell by introducing, into the cell, an effective amount of an isolated protein that methylates the targeted gene's H3-K27.

In a further non-limiting embodiment, when a specific gene is targeted for expression suppression, introduction of the protein into the cell expressing the specific targeted gene does not suppress the expression of other genes expressed by the cell.

In one embodiment, H3-K27 is mono-methylated.
In another embodiment, H3-K27 is di-methylated.
In another embodiment, H3-K27 is tri-methylated.

In one embodiment the targeted gene is a cytokine, for example, TNF-α, TGF-β, IFN-γ, IL-2 or IL-10.

In another embodiment, the targeted gene is an oncogenic gene, for example, MDM2, Src, a Ras kinase, a receptor tyrosine kinase, EFGR, PDGFR or VEGFR. In another embodiment, the targeted gene is a homeodomain gene, for example, HOXA2, HOXA5, HOXA7, HOXA9, HOXB9, HOXC6, HOXC8, HOXD8, or Hey1.

In another embodiment, the targeted gene is a transcription factor, for example, myc or NF-κB.

In another embodiment, the targeted gene codes for a receptor, for example, an Androgen Receptor, Retinoic Acid receptor (RAR), or Retinoic Acid X receptor (RXR).

In another embodiment, the targeted gene is a regulatory gene which suppresses the expression of a second gene. Targeting the regulatory gene, according to the present invention, reduces the suppression of the second gene, therefore increasing the second gene's expression. In one embodiment, the second gene is a transmembrane protein which functions, for example, in cell adhesion, or tumor suppression. Such proteins include, for example, E cadherin or M50/Beta-catenin, respectively In another embodiment, the targeted gene is a regulatory gene which promotes the expression of a second gene. Targeting the regulatory gene according to the present invention, reduces the expression of the second gene.

In another embodiment, the targeted gene codes for a protein which function, for example, in regulating cell proliferation. Such proteins include, for example, cyclins such as Cyclin D.

In another embodiment, the targeted gene encodes an HIV transcriptional activator protein tat.

In one embodiment, the transcriptional expression of a gene is inhibited in cells of a multicellular organism.

In another embodiment, the transcriptional expression of a gene is inhibited in a host cell, for example, but not limited to, a cell of a eukaryotic cell line, for example, a breast cancer cell line (e.g. an MCF7 breast cancer cell line or an MCF10A breast cancer cell line), a prostate cancer cell line (e.g. a PC3 prostate cancer cell line or an RWPE prostate cancer cell line), or a leukemic cell line (e.g. a K562 leukemic cell line, an HL-60 leukemic cell line, or a U937 leukemic cell line).

In another embodiment, the introduced protein further comprises a nuclear localization signal, for example, the amino acid sequence Lys-Arg-Met-Arg (KRMR) (SEQ ID NO:3).

In another non-limiting embodiment, the introduced protein further comprises a histone demethylase inhibitor.

In another non-limiting embodiment, the introduced protein is isolated from a *chlorella* virus, for example, the *chlorella* viruses PBCV-1, NY-2A, NY-2B or MA-1D.

In another non-limiting embodiment, the introduced protein is a viral SET (vSET) histone lysine methyltransferase domain encoded by a vset gene isolated from *Paramecium bursar Chlorella* Virus-1 (PBCV-1).

In another non-limiting embodiment, the introduced protein is a vSET-like protein encoded by a vset-like gene isolated from a *chlorella* virus.

The invention also provides for expression vectors that encode the introduced protein (e.g., a recombinant viral histone lysine methyltransferase, vSET or vSET-like protein), for example, a lentivirus (e.g. *lenti*-virus vector pLVET-tTRKRAB) or an adenovirus (e.g. adeno virus vector VQpacAd5CMVK-NpA) expression vector, which act as vehicles for introduction of the protein into the cell. In further embodiments, the expression vector comprises a cationic lipid, polymer, or liposome complex.

The invention also provides for pharmaceutical compositions for human administration comprising a purified lysine methyltransferase, histone lysine methyltransferase, viral histone lysine methyltransferase, protein comprising a *Chlorella* virus SET domain of a viral histone lysine methyltransferase, vSET or vSET-like protein in a pharmaceutically acceptable carrier.

The invention also provides for methods of treating a disease or disorder in which suppression of gene expression can provide a therapeutic benefit. Such diseases or disorders include, but are not limited to, blood disorders (for example, but not limited to, acute lymphoid leukemia and lymphoma), developmental disorders (for example, but not limited to, mental retardation, epilepsy or movement disorders), inflammatory disorders, cancer (for example, but not limited to, gastric cancer, breast cancer, colorectal cancer, thyroid cancer, ovarian cancer, prostate cancer and leukemia), and diseases of the central and peripheral nervous systems wherein over expression of one or more genes contributes to pathology of the disease or disorder. Alternatively, the invention also provides for methods of treating a disease or disorder wherein reducing the expression of one or more genes can provide a therapeutic benefit even if the disorder is not caused by the over expression of one or more genes.

The invention also provides methods of treating an individual having a disorder requiring gene therapy, comprising administering to the individual a composition which comprises a therapeutic vector encoding a protein of the present application, for example, a protein comprising a *Chlorella* virus SET domain of a viral histone lysine methyltransferase.

In one non-limiting embodiment, expression of the protein carried by the vector results in suppression of a targeted gene or genes whose expression contributes to a pathological condition in the individual, for example, but not limited to, cancer. The invention also provides for nucleic acid constructs and expression vectors encoding a protein of the present invention (for example, a protein comprising a *Chlorella* virus SET domain of a viral histone lysine methyltransferase) and a second DNA targeting protein, wherein the DNA targeting protein enables methylation and transcriptional suppression of a specific target gene.

The invention also provides for fusion proteins a protein of the present invention (for example, a protein comprising a *Chlorella* virus SET domain of a viral histone lysine methyltransferase) and a DNA targeting protein, wherein the DNA targeting protein enables methylation and transcriptional suppression of a specific target gene.

The invention also provides for methods of introducing a protein of the present invention (for example, a protein comprising a *Chlorella* virus SET domain of a viral histone lysine methyltransferase) or an expression vector that encodes a recombinant protein of the present application into a cell.

The invention also provides for methods of inhibiting the growth cycle of a cell by introducing a protein of the present invention (for example, a protein comprising a *Chlorella* virus SET domain of a viral histone lysine methyltransferase) or an expression vector that encodes a recombinant a protein of the present invention (for example, a protein comprising a *Chlorella* virus SET domain of a viral histone lysine methyltransferase) into a cell.

BRIEF DESCRIPTION OF THE DRAWINGS

FIGS. 2a-2i show the methylation of *Chlorella* histone H3-K27 by vSET. a, Sequence alignment of H3 from *Chlorella* NC64A, *Homo sapien, Mus musculus, Xenopus laevis, Caenorabditis elegans* and *Chlamydomonas reinhardtii*. Residues different in H3 are shown in blue. b, vSET methylates H3 in nucleosomes. Native histone H3 was used as a control (right lane). c, HKMTase activity of vSET targets H3-K27, as illustrated by methyl transfer from $^{14}$C-methyl-SAM to GST-fusion H3 peptides (residues 1-57). Fluorescent values relative to wild-type enzyme activity are indicated under the lower panel. Relative amounts of GST-H3 in the assays are shown in SDS-PAGE (upper panel). d, Western blot analysis of vSET-treated GST, GST-H3 wild-type and K27R mutant peptides using anti-H3-K27me1/2/3, anti-H3-K4me2, anti-H3-K9me2 and anti-H3-K36me2 antibodies. e, Western blot analyses of *Chlorella* H3 before and after PBCV-1 infection at specified time points using antibodies against histone H3 with different modifications. f, vSET is localized in the nucleus of PBCV-1 infected *Chlorella* cells collected 60 minutes after infection, as illustrated by immuno-fluorescence. Uninfected and 60 min post-infected *Chlorella* cells were probed with anti-vSET (upper and middle panels, respectively) or anti-H3 antibodies (lower panel). g, vSET and host *Chlorella* H3-K27me2 co-localize in the nucleus 60 minutes post PBCV-1 infection, as shown by confocal fluorescence imaging. *Chlorella* cells were probed with anti-vSET and anti-H3-K27me2 antibodies and visualized by immunofluorescence using Alexa488 and Alexa594 dyes, respectively. h-i show the enzyme kinetics of H3-K27 methylation by vSET, as determined using a H3 peptide (aa 13-33) substrate and mass spectrometry analysis: h, K27 methylation of a H3 peptide from unmodified state to mono-, di- and tri-methylation states catalyzed by vSET as illustrated by mass spectrometry analysis at specified time points during the reaction; i, The entire time course of the H3-K27 methylation of the H3 peptide by vSET as analyzed by mass spectrometry.

FIGS. 3a-3d show the nuclear localization and H3-K27 methylation of H3-K27 by vSET. a, Nuclear localization of GFP-vSET in transiently transfected NIH-3T3 cells. Fluorescence images show that wild-type vSET is located in the nucleus, whereas a triple mutant, KR(M)R(SEQ ID NO:3)/AA(M)A (SEQ ID NO:4) (residues 85-88) is in the cytoplasm. Cells were counterstained with DAPI to highlight nuclei. b, Western blot analysis of Hela cells showing effects of treatment of EZH2-specific and mock siRNAs on protein expression of EZH2, RING1, SUZ12 and histone H3 with different modifications. Lamin B was used as a control. c, Western blot analysis of the nuclear extract of Hela cells treated with EZH2 siRNA and subject to in vitro methylation by vSET. d, Western blot analysis showing di and tri-methylation of H3-K27 upon tetracycline induction of stably transfected vSET in Hela cells 72 hours after EZH2 knock-down by siRNA.

FIG. 8 shows that expression of vSET in *Arabidopsis* leads to apoptosis. Transgenic plants that contain a beta-estradiol inducible vector expressing vSET. a. *Arabidopsis* before induction of vSET expression. b,c. Two *Arabidopsis* plants 10 days after beta-estradiol induced expression of vSET.

FIG. 9 shows the nucleic acid sequence of the PBCV-1 gene A612L that encodes the vSET protein.

FIG. 10 shows the amino acid sequence of the vSET polypeptide encoded by the PBCV-1 gene A612L.

FIG. 15 shows a table of the antibodies in the experiments described in the application.

FIG. 16 shows tables describing the amino acid sequences of histone H3 Peptides (aa 1-57) used in FIG. 2C; the sequences of siRNAs used for Human EZH2 Knockdown experiments; and a list of RTPCR and ChIP Primers used in the experiments described in the application.

DETAILED DESCRIPTION

Figure 1A:
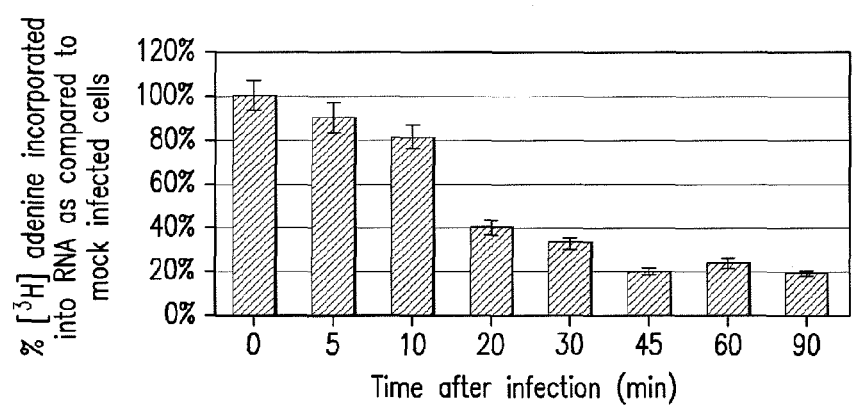
FIGS. 1a-1e show the presence of vSET in PBCV-1 virions. a, Host transcription shutoff by virus infection. Incorporation of $^3$H-adenine into RNA in PBCV-1 infected *Chlorella* NC64A cells as compared to mock-infected cells. b, Detection of vSET in PBCV-1 virions and virus infected *Chlorella* cells by immunoprecipitation (IP) and then immunoblotting (IB) with anti-vSET antibodies. c, The presence of vSET in PBCV-1 virions is not due to external contamination, as demonstrated by trypsin pre-treatment of purified PBCV-1 virus particles. d, Northern blot analysis establishes that vset is expressed as an ~1.8 kDa transcript in PBCV-1 infected *Chlorella* NC64A cells beginning at 60 minutes after infection. e, Histone H3K27 methylation activity of vSET in the lysate of PBCV-1 virions as demonstrated using western blot analysis with anti-H3-K27me2 antibodies.

The present invention provides for selective or general suppression or inhibition of gene expression. Suppression of gene expression is a powerful tool for treating a number of disease states associated with inappropriate gene expression, particularly cancer. While a number of approaches are in development, including interfering RNA (RNAi), antisense, histone deacetylase inhibitors, and the use of intercalating agents, and pseudo-expression blockers that actually target the expressed protein, the present invention represents a new approach.

The invention is based, in part, on the discovery that viruses can directly modify host chromatin to interfere with host gene transcription. Particularly, it was discovered that *Paramecium bursaria chlorella* virus 1 (PBCV-1) encodes a functional SET domain histone lysine methyltransferase (termed vSET) that is directly linked to rapid inhibition of host transcription after virus infection. Additionally, it was discovered that vSET is packaged in the PBCV-1 virion and comprises a nuclear localization signal. vSET causes host transcriptional repression by selective methylation of histone H3 at lysine 27, a post-translational modification that is well established to trigger long-term gene silencing in eukaryotes. Further, vSET induces cell accumulation at the G2/M phase of the cell cycle by recruiting the Polycomb repressive complex 1 (PRC1) wherein the PRC1 component protein CBX8 binds to the methylated H3-K27 in mammalian cells. Finally, it was discovered that vSET-like proteins exhibiting H3-K27 methylation activity are conserved in the *chlorella* virus family.

Certain experimental results underlie the present invention: transfection of human embryonic kidney 293T cells with wild type vSET suppressed gene transcription, resulting in about 60-90% transcription repression in the host cell.

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "gene expression" refers to the transcription of RNA from a genomic DNA (gDNA) template. The RNA can be messenger RNA (mRNA), which is subsequently translated on ribosomes to produce protein; ribosomal RNA (rRNA); or transfer RNA (tRNA). The latter two forms of RNA are involved in the synthesis of all cellular proteins. "Gene expression" may also refer to synthesis of a protein.

As used herein, "suppression" or "inhibition" of gene expression refers to a reduction in the normal level of expression.

The cell in which target gene expression is suppressed/inhibited may be any eukaryotic cell. In specific embodiments, the cell may be an animal cell, a plant cell, a mammalian cell, a human cell, a murine cell, a racine cell, a canine cell, a feline cell, an equine cell, a bovine cell, an ovine cell, a porcine cell, etc.

A "multicellular organism" can be any animal or plant. In specific embodiments, the multicellular organism is a mammal, including but not limited to the human, canine, feline, equine, bovine, ovine, porcine, murine, racine, etc.

The term "therapeutically effective amount" refers to the amount of the introduced protein that is sufficient to result in a therapeutic response. A therapeutic response may be any response that a user (e.g., a clinician) will recognize as an effective response to the therapy, including symptoms and surrogate clinical markers described herein. Thus, a therapeutic response will generally be an amelioration of one or more symptoms or signs of a disease or disorder, or an increased survival, for example, but not limited to, a decrease in the transcriptional expression of an oncogenic gene, an inflammatory gene such as a cytokine, a transcription factor gene, a developmental gene, or a viral replication gene.

The term "effective amount" refers to an amount of introduced protein that is either a therapeutically effective amount or an amount that is sufficient to suppress or inhibit expression of a targeted gene.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

The term "chromatin histone protein" has its ordinary meaning, e.g., as set forth in Jenuwein et al., Science, 293:1074-1080 (2001); Cheung et al., Cell, 103: 263-271 (2000); Turner et al., Cell, 111:285-291, (2002); Kouzarides et al., Curr. Opin. Genet. Dev., 12: 198-209 (2002); and Lachner et al., Curr. Opin. Cell Biol., 14:286298 (2002)

Lysine Methyltransferase

In one non-limiting embodiment of the invention, the protein introduced according to the present invention is a lysine methyltransferase. The term "lysine methyltransferase" refers to a polypeptide which exhibits methyltransferase activity. The polypeptide can transfer one, two, or three or more methyl groups from a methyl donor to a lysine residue within the intracellular environment of a cell. Alternatively, the lysine methyltransferase can transfer one, two, or three or more methyl groups from a methyl donor to a lysine residue in an extracellular environment, for example, in an in vitro cell-free translation systems. Methyltransferases are described generally in, for example, Nightingale et al., Curr Opin Genet Dev 16, 125-36 (2006); Fischle et al., Curr Opin Cell Biol 15, 172-83 (2003); Bannister et al., Cell 109, 801-6 (2002); Lachner et al., J Cell Sci 116, 2117-24 (2003); Sims et al., Genes Dev 20, 2779-86 (2006); Wysocka et al., Nature 442, 86-90 (2006); and Bernstein et al., Proc Natl Acad Sci USA 99, 8695-700 (2002), which are hereby incorporated by reference in their entireties.

In accordance with the present invention, the lysine methyltransferase has the properties of a histone lysine methyltransferase. In a specific embodiment, the protein is a histone lysine methyltransferase. In one embodiment, the histone lysine methyltransferase is an enzyme that is functional when present as a dimer, wherein the protein can function to transfer one, two, or three or more methyl groups from a methyl donor to a lysine residue comprised in a histone protein.

The methyl donor may be any agent which comprises one or more methyl groups, such as, for example but not limited to, S-adenosyl-L-methionine. The methyl donor may be endogenous to the cell or organism to which the lysine methyltransferase is introduced. Alternatively, the methyl donor is introduced onto the cell or organism before, at the same time, or after the lysine methyltransferase is introduced.

In a specific embodiment of the invention, lysine methyltransferase is a viral histone lysine methyltransferase that can transfer a methyl group from a methyl donor to a lysine residue of a chromatin histone protein. In a further embodiment, the viral histone lysine methyltransferase transfers a methyl group to Lysine 27 of the chromatin histone 3 protein (H3-K27). The H3-K27 may be mono-, di-, or tri-methylated by the histone lysine methyltransferase. In a further embodiment, the viral histone lysine methyltransferase comprises an SET domain.

In a preferred embodiment of the invention, the lysine methyltransferase of the present invention is a protein comprising a *Chlorella* virus SET domain of a viral histone lysine methyltransferase.

In one embodiment exemplified below, the lysine methyltransferase of the present invention is a viral histone lysine methyltransferase comprising an SET domain from *Para-* mecium bursaria chlorella virus 1 (vSET). The viral histone lysine mehtyltransferase is preferably encoded by the *Paramecium bursaria chlorella* virus 1 (PBCV-1) gene A612L, a nucleic acid which encodes the PBCV-1 vSET histone lysine methyltransferase (Nucleotides 293003-293362 of GenBank accession number NC_000852) (SEQ ID NO:1).

In another non-limiting embodiment, the viral histone lysine mehtyltransferase can be encoded for by a vset-like gene, a nucleic acid isolated from any *chlorella* virus which encodes a vSET-like protein that can function as a methyltransferase, specifically, a protein that can methylate H3-K27. Alternatively, the viral histone lysine methyltransferase can be encoded by any nucleic acid molecule exhibiting at least 50%, at least 60%, at least 70%, at least 80%, at least 90%, at least 95%, or up to 100% homology to the A612L gene (where homology may be determined by standard software such as BLAST or FASTA), and any sequences which hybridize under standard conditions to these sequences.

In another non-limiting embodiment, the viral histone lysine methyltransferase may be any other protein or may be encoded by any other nucleic acid sequence that encodes a viral histone lysine methyltransferase (having the same functional properties as the aforementioned polypeptide sequences) that have the ability to transfer one, two, or three or more methyl groups from a methyl donor to the histone, e.g., H3-K27.

In a specific embodiment exemplified below, a vSET histone lysine methyltransferase also refers to an amino acid sequence depicted in SEQ ID NO:2 (GenBank accession number AAC96946), and any other amino acid sequence that encodes a viral histone lysine mehtyltransferase polypeptide having the same methyltransferase function of SEQ ID NO:2 and which may have at least about 80%, at least 90%, at least 95%, or up to 100% homology thereto.

In one embodiment the viral histone lysine methyltransferase is a vSET polypeptide that is purified from *Paramecium bursar chlorella* virus 1. Alternatively, the viral histone lysine methyltransferase is a vSET-like polypeptide purified from any other virus of the *chlorella* virus family including, for example, but not limited to, *chlorella* viruses NE-8D, NYb-1, CA-4B, AL-1A, NY-2C, NC-1D, NC-1C, CA-1A, CA-2A, IL-2A, IL-2B, IL-3A, IL-3D, SC-1A, SC-1B, NC-1A, NE-8A, AL-2C, MA-1E, NY-2F, CA-1D, NC-1B, NY-s1, IL-5-2s1, AL-2A, MA-1D, NY-2B, CA-4A, NY-2A, XZ-3A, SH-6A, BJ-2C, XZ-6E, XZ-4C, XZ-5C, and XZ-4A.

Alternatively, the viral histone lysine methyltransferase is a recombinant vSET polypeptide encoded by a recombinant nucleic acid, for example, a recombinant DNA molecule. The nucleic acid can encode any of the specific vSET or vSET-like proteins identified above.

In one non-limiting embodiment, the lysine methyltransferase comprises a nuclear localization signal. As used herein, "nuclear localization signal" refers to a molecule or polypeptide that facilitates the movement of the lysine methyltransferase to the nucleus of the cell to which the lysine methyltransferase is introduced. The nuclear localization signal can be any agent or compound that facilitates the movement of the lysine methyltransferase to the nucleus of a cell where the enzyme transfers one or more methyl groups from a methyl donor to a target gene. Examples of nuclear localization signals include, but are not limited to, polypeptides such as, for example, the amino acid sequences Lys-Arg-Met-Arg (KRMR) (SEQ ID NO:3), Pro-Arg-Ile-Val (PRIV) (SEQ ID NO:5), Lys-Arg-Pro-Arg (KRPR) (SEQ ID NO:6), and Arg-Arg-Pro-Arg (RRPR) (SEQ ID NO:7).

Targeted Methyl Transferases

In another, non-limiting embodiment, the lysine methyltransferase further comprises a targeting protein, such as a DNA binding protein, which increases the specificity of methylation relative to the targeted gene or protein associated therewith. The lysine methyltransferase may be fused to the targeting protein in the form of a fusion protein, or, alternatively, an expression vector may encode a lysine methyltransferase fused to a targeting protein. As used herein, "DNA binding protein" means a protein that contains a polypeptide sequence that specifically interacts with DNA regulatory sequences associated with a gene or class of genes. For purposes of this invention, the whole protein or just the DNA binding domain of the protein can be a "DNA binding protein." Such DNA binding proteins include transcription factors, enhancer proteins, suppressor proteins, and the like. Non-limiting examples of DNA binding protein are NF-kB and DNA binding domains from the polycomb target genes HOXC6 and HOXC8.

The DNA binding protein is effective to target the lysine methyltransferase to one or more specific "targeted genes," thus the targeted gene is methylated while non-targeted genes remain substantially unaffected by the lysine methyltransferase. Therefore only the targeted genes experience transcriptional expression suppression. The methods of the present invention contemplate the targeting of any gene for transcription suppression.

In one non-limiting embodiment, genes that are targeted for transcription suppression are genes involved in oncogenesis and/or tumorigenesis. As used herein, the term "oncogenesis" refers to the progression of cytological, genetic, and/or cellular changes that culminate in a malignant tumor. As used herein, the term "tumorigenesis" refers to the abnormal growth of tissue resulting in a swelling or mass of tissue. For example, targeted genes include inhibitors of tumor suppressors, such as murine double minute 2 (MDM2); oncogenic proteins, such as Src tyrosine kinases, Ras kinases, receptor tyrosine kinases, epidermal growth factor receptor (EGFR), platelet-derived growth factor receptors (PDGFR), and vascular endothelial growth factor receptors (VEGFR); transcription factors such as myc or NF-kB; inflammatory factors and cytokines such as tumor necrosis factor-alpha (TNF-α) OR NF-kB, transforming growth factor-beta (TGF-β), interferon-gamma (IFN-γ), interleukin-2 (IL-2) and interleukin-10 (IL-10); homeodomain genes such as HOXA2, HOXA5, HOXA7, HOXA9, HOXB9, HOXC6, HOXC8, HOXD8, and Hey1; receptors such as Androgen Receptor, Retinoic Acid receptor (RAR), or Retinoic Acid X receptor (RXR); cell cycle regulating proteins (e.g., proteins that regulate cell division) such as Cyclin D; and viral replication factors such as human immunodeficiency virus type 1 transactivator protein (tat).

Targeted gene expression suppression according to the instant invention therefore provides for methods of treating a disease or disorder in which suppression of gene expression can provide a therapeutic benefit. Such diseases or disorders include, but are not limited to, prostate cancer (androgen receptor and/or HOXC8), developmental disorders (HOXA2), breast cancer (HOXA5 and/or E Cadherin), Ovarian cancer (HOXA7 and/or E Cadherin), blood disorders (HOXA9), Leukemia (Retinoic Acid receptor (RAR)), cancer (Retinoic Acid X receptor (RXR), and/or M50/Beta Catenin, and/or Cyclin D), basal cell carcinoma (M50/Beta Catenin), and inflammatory disorders (NF-κB).

In another non-limiting embodiment, the genes that are targeted for transcription suppression are regulatory genes which function to suppress the expression of a second gene or genes. Targeting the regulatory genes, according to the present invention, reduces the suppression of the second gene, thus, increasing the second gene's expression.

In one embodiment, the second gene is, for example, but not by way of limitation, a transmembrane protein which functions, for example, in cell adhesion and/or tumor suppression. Such proteins include, for example, E cadherin or M50/Beta-catenin. Increasing the expression of a second gene as described above provides for methods of treating a disease or disorder in which transcriptional activation of gene expression can provide a therapeutic benefit. Such diseases or disorders include, but are not limited to, cancers. For example, loss of function or reduced expression of E-cadherin, a tumor suppressor gene, is thought to contribute to progression of cancer (such as, but not limited to, gastric, breast, colorectal, thyroid and ovarian cancer), by increasing proliferation, invasion, and/or metastasis. Therefore, transcription activation of E-cadherin by vSET, through a reduction in expression of an E-cadherin suppressor, can provide a therapeutic benefit.

In another non-limiting example, the expression of Beta-catenin is increased via a vSET mediated reduction in expression of a Beta-catenin suppressor. Beta-catenin plays an important role in Wnt signaling pathway, for example, in various aspects of liver biology including liver development (both embryonic and postnatal), and liver regeneration following partial hepatectomy (Thompson et al., Hepatology 45(5):1298-305 (2007)).

In another non-limiting example, the expression of Retinoic Acid X receptor (RXR) is increased via a vSET mediated reduction in expression of an RXR suppressor. Increased expression of RXR can have beneficial effects on vision, immune function, bone metabolism, skin health, and reducing risk of heart disease.

In another embodiment, the targeted gene is a regulatory gene which promotes the expression of a second gene. Targeting the regulatory gene according to the present invention reduces the expression of the second gene.

Suppression or Inhibition of Gene Expression

A lysine methyltransferase can be introduced into a cell of a multicellular organism through a variety of techniques. It can be introduced as a protein or through an expression vector that produces the protein in the cell in situ.

When introduced into a cell, unmodified lysine methyltransferase exhibits non-specific methylation of a cell's genes, thus suppressing the transcriptional expression of at least one, two, three, four or up to all of the genes in the cell. Targeted lysine methyltrasnferase exhibits specific methylation at the target gene (or genes sharing the same target characteristics), thus suppressing that gene (or genes).

In one non-limiting embodiment of the invention, methylation of a target gene's chromatin H3-K27 by a lysine methyltransferase suppresses the transcription of the gene or genes. The transcription suppression of the gene or genes can be between about 5% and 100%, more preferably between about 20% and 95%, more preferably between about 40% and 85%, and most preferably between about 60% and 90% suppression of target gene transcription as compared to a wild-type target gene that is not methylated at H3-K27. Where multiple genes are targeted, not every gene will necessarily be suppressed to the same degree.

In one embodiment, the lysine methyltransferase may be administered with a histone demethylase inhibitor. The histone demethylase inhibitor may be administered at the same time as, before, or after administration of the lysine methyltransferase.

In one embodiment, the transcription suppression can occur from about 1 to about 120 minutes, more preferably from about 5 to about 60 minutes, more preferably from about 10 to about 50 minutes, and most preferably from about 20 to about 40 minutes following introduction of the lysine methyltransferase into a cell containing the target gene.

In a further non-limiting embodiment, when the methylation of a target gene's chromatin H3-K27 by the lysine methyltransferase occurs in a cell, the methylation results in arrest of the cell cycle. Methylation can result in accumulation of cells at the cell cycle phase in which arrest occurs. For example, NIH-3T3 or HeLa cells transiently transfected with vSET results in arrest of the cell cycle at the G2/M transition, and accumulation of cells at the G2/M cell cycle phase.

Methylation of H3-K27 by vSET can result in long term gene transcription suppression that can persist for up to 1 hour, 1 day, or longer. Alternatively, the gene transcription suppression can be permanent, for example, suppression of gene transcription in a cell can persist as long as the cell is alive. Long term gene transcription suppression can be achieved through recruitment of proteins to the methylated H3-K27 site. For example, following methylation by a viral histone lysine methyltransferase, H3-K27 can become associated with PcG PRC1 or Ezh2/PRC2 complexes that lead to long-term gene silencing. In one specific, non-limiting embodiment, the PcG PRC1 protein CBX8 becomes associated with di-methylated and tri-methylated H3-K27, resulting in long term gene silencing.

In another non-limiting embodiment of the invention, the lysine methyltransferase is administered to a cell with a histone demethylase inhibitor. Such inhibitors include, for example, phenelzine, tranylcypromine, nialamide, clorgyline, deprenyl, and pargyline.

Delivery of Proteins

According to the invention, the methylating protein may be introduced either as a protein or as a nucleic acid encoding the protein. Where the methylating protein is provided as a protein, numerous methods can be employed to achieve uptake and targeting of the lysine methyltransferase by the cells. According to the invention, the lysine mehtyltransferase delivered to a cell or administered to an organism can be a protein isolated from a cell culture, for example, a eukaryotic cell line, in which the cell culture has been infected with a chorella virus (e.g., PBCV-1). Alternatively, the lysine methyltransferase can be a recombinant protein. Peptide sequences have been identified that mediate membrane transport, and accordingly provide for delivery of polypeptides to the cytoplasm. For example, such peptides can be derived from the Antennapedia homeodomain helix 3 to generate membrane transport vectors, such as penetratin (see PCT Publication WO 00/29427; see also Fischer et al., J. Pept. Res. 55:163-72 (2000); DeRossi et al., Trends in Cell Biol. 8:84-7 (1998); Brugidou et al., Biochem. Biophys. Res. Comm. 214:685-93 (1995)), the VP22 protein from herpes simplex virus (Phelan et al., Nat. Biotechnol. 16:440-3 (1998)), and the HIV TAT transcriptional activator.

Protein transduction domains, including the Antennapedia domain and the HIV TAT domain (see Vives et al., J. Biol. Chem. 272:16010-17 (1997)), possess a characteristic positive charge, which led to the development of cationic 12-mer peptides that can be used to transfer therapeutic proteins and DNA into cells (Mi et al., Mol. Therapy 2:339-47 (2000)). The above-mentioned protein transduction domains are covalently linked to the target protein, either by chemical covalent cross-linking or generation as a fusion protein. Further, a non-covalent, synthetic protein transduction domain has been developed by Active Motif Inc. (Carlsbad, Calif.). This domain associates with the target protein through hydrophobic interactions, and advantageously dissociates from the protein once inside the cell (Morris et al., Nat. Biotechnol. 19:1173-6 (2001)). In addition, lipid carriers have recently been shown to deliver proteins into cells in addition to an established use for delivering naked DNA (Zelphati et al., J. Biol. Chem. 276:35103-10 (2001)). For an overview of protein translocation techniques see Bonetta, The Scientist 2002; 16(7):38.

Gene Therapy

The term "gene therapy" refers to a method of changing the expression of an endogenous gene by exogenous administration of a second gene. As used herein, gene therapy also refers to the replacement of defective gene encoding a defective protein, or replacement of a missing gene, by introducing a functional gene corresponding to the defective or missing gene into somatic or stem cells of an individual in need.

The gene to be administered for the methods of the present invention can be isolated and purified using ordinary molecular biology, microbiology, and recombinant DNA techniques within the skill of the art. For example, nucleic acids encoding the target protein can be isolated using recombinant DNA expression as previously described, and as described in the literature. See, e.g., Sambrook et al. (2001) Molecular Cloning: A Laboratory Manual. 3rd Ed. Cold Spring Harbor Laboratory Press: Cold Spring Harbor, N.Y., which is incorporated herein by reference in its entirety. The nucleic acid encoding the protein may be full-length or truncated, so long as the gene encodes a biologically active protein.

The identified and isolated gene can then be inserted into an appropriate cloning vector. Vectors suitable for gene therapy include viruses, such as adenoviruses, adeno-associated virus (AAV), vaccinia, herpesviruses, baculoviruses and retroviruses, parvovirus, lentivirus, bacteriophages, cosmids, plasmids, fungal vectors and other recombination vehicles typically used in the art which have been described for expression in a variety of eukaryotic and prokaryotic hosts, and may be used for gene therapy as well as for simple protein expression.

In a preferred embodiment, the vector is a viral vector. Viral vectors, especially adenoviral vectors can be complexed with a cationic amphiphile, such as a cationic lipid, polyL-lysine (PLL), and diethylaminoethyldextran (DE-LAE-dextran), which provide increased efficiency of viral infection of target cells (See, e.g., U.S. Pat. No. 5,962,429, incorporated herein by reference).

The coding sequences of the gene to be delivered are operably linked to expression control sequences, e.g., a promoter that directs expression of the gene. As used herein, the phrase "operatively linked" refers to the functional relationship of a polynucleotide/gene with regulatory and effector sequences of nucleotides, such as promoters, enhancers, transcriptional and translational stop sites, and other signal sequences. For example, operative linkage of a nucleic acid to a promoter refers to the physical and functional relationship between the polynucleotide and the promoter such that transcription of DNA is initiated from the promoter by an RNA polymerase that specifically recognizes and binds to the promoter, and wherein the promoter directs the transcription of RNA from the polynucleotide. Furthermore, the expression vector can comprise inducible promoters, for example, a beta-estradiol inducible expression vector. Inducible expression vectors are well known in the art. In one non-limiting example, the expression vector is a viral vector, for example, *lenti*-virus vector pLVET-tTRKRAB or adeno virus vector, VQpacAd5CMVK-NpA (Viral Quest).

In one specific embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, Proc. Natl. Acad. Sci. USA, 86:8932-8935 (1989); Zijlstra et al., Nature, 342:435-438 (1989); U.S. Pat. No. 6,244,113 to Zarling et al.; and U.S. Pat. No. 6,200,812 to Pati et al.), each of which are hereby incorporated by reference in their entirety.

Delivery of Gene Therapy Vectors

Where the methylating protein is introduced via a nucleic acid, said nucleic acid may be comprised in a gene therapy vector. Delivery of a gene therapy vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

Direct Transfer.

In a specific embodiment, the vector is directly administered in vivo, where it enters the cells of the organism and mediates expression of the gene. This can be accomplished by any of numerous methods known in the art, e.g., by constructing it as part of an appropriate expression vector and administering it so that it becomes intracellular, e.g., by infection using a defective or attenuated retroviral or other viral vector, or by direct injection of naked DNA, or by use of microparticle bombardment; or coating with lipids or cell-surface receptors or transfecting agents, encapsulation in polymers or biopolymers, encapsulation in liposomes, microparticles, or microcapsules, by administering it in linkage to a peptide or other ligand known to enter the nucleus; or by administering it in linkage to a ligand subject to receptor-mediated endocytosis, etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., Mol. Therapy 2:339-47 (2000)). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188). Additionally, a technique referred to as magnetofection can be used to deliver vectors to mammals. This technique associates the vectors with superparamagnetic nanoparticles for delivery under the influence of magnetic fields. This application reduces the delivery time and enhances vector efficacy (Scherer et al., Gene Therapy 9:102-9 (2002)).

In a specific embodiment, the nucleic acid can be administered using a lipid carrier. Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 1989; 337:387). Intravenous injection of cationic lipid-plasmid complexes into mice has been shown to result in expression of the DNA in lung (Brigham et al., Am. J. Med. Sci. 1989; 298:278). Representative cationic lipids include those disclosed, for example, in U.S. Pat. No. 5,283,185; and e.g., U.S. Pat. No. 5,767,099, the disclosures of which are incorporated herein by reference.

Preferably, for in vivo administration of viral vectors, an appropriate immunosuppressive treatment is employed in conjunction with the viral vector, e.g., adenovirus or lentivirus vector, to avoid immuno-deactivation of the viral vector and transfected cells. For example, immunosuppressors such as anti-CD4 antibody, can be administered to block humoral or cellular immune responses to the viral vectors. In that regard, it is advantageous to employ a viral vector that is engineered to express a minimal number of antigens.

Indirect Transfer.

Somatic cells may be engineered ex vivo with a construct encoding a protein, for example, a lysine methyltransferase, and re-implanted into an individual. This method is described generally in WO 93/09222 to Selden et al., which is hereby incorporated by reference in its entirety. In addition, this technology is used in Cell Based Delivery's proprietary ImPACT technology, described in Payumo et al., Clin. Orthopaed. and Related Res. 403S: S228-S242 (2002). In such a gene therapy system, somatic cells (e.g., fibroblasts, hepatocytes, or endothelial cells) are removed from the patient, cultured in vitro, transfected with the gene(s) of therapeutic interest, characterized, and reintroduced into the patient. Both primary cells (derived from an individual or tissue and engineered prior to passaging), and secondary cells (passaged in vitro prior to introduction in vivo) can be used, as well as immortalized cell lines known in the art. Somatic cells useful for the methods of the present invention include but are not limited to somatic cells, such as fibroblasts, keratinocytes, epithelial cells, endothelial cells, glial cells, neural cells, formed elements of the blood, muscle cells, other somatic cells that can be cultured, and somatic cell precursors. In a preferred embodiment, the cells are fibroblasts or mesenchymal stem cells.

Nucleic acid constructs, which include the exogenous gene and, optionally, nucleic acids encoding a selectable marker, along with additional sequences necessary for expression of the exogenous gene in recipient primary or secondary cells, are used to transfect primary or secondary cells in which the encoded product is to be produced. Such constructs include but are not limited to infectious vectors, such as retroviral, herpes, adenovirus, lentivirus, adenovirus-associated, mumps and poliovirus vectors, can be used for this purpose.

Transdermal delivery is especially suited for indirect transfer using cell types of the epidermis including keratinocytes, melanocytes, and dendritic cells (see, e.g., Pfutzner et al., Expert Opin. Investig. Drugs 9:2069-83 (2000), which is hereby incorporated by reference in its entirety).

Mesenchymal stem cells (MSCs) are non-blood-producing stem cells produced in the bone marrow. MSCs can be made to differentiate and proliferate into specialized non-blood tissues. Stem cells transfected with retroviruses are good candidates for the therapy due to their capacity for self-renewal. This ability precludes repetitive administration of the gene therapy vector. Another advantage is that if the injected stem cells reach the target organ and then differentiate, they can replace the damaged or malformed cells at the organ Control of Gene Expression for Disease Therapy In one embodiment, the present invention provides for methods of suppressing the transcriptional expression of one or more genes in a call by introducing an effective amount of a methylating protein into the cell.

In one non-limiting embodiment, a lysine methyltransferase according to the present invention, for example, vSET or a recombinantly produced vSET, can target a specific gene. In one non-limiting example, vSET can be fused to a DNA binding protein domain that recognizes specifically the promoter sequence of a given target gene, or to a histone binding protein domain that interacts with a core histone H3 or H4 carrying a distinct post-translational amino acid modification at the target gene site. In further non-limiting embodiments, vSET can be engineered to possess regulatory capacity via mutagenesis of amino acid residues at the enzyme active site or methyl donor (S-adenosyl-methionine) co-factor binding site, in which a small-molecule chemical compound can be developed to control the enzymatic activity of vSET in a spatial and temporal manner.

In Vivo Control of Gene Expression:

The present invention provides for methods of controlling the in vivo expression of a gene in an organism or subject, for example, to treat a condition associated with increased gene expression, or a condition that would benefit by a decrease in transcriptional expression of one or more genes, by administering to a subject in need of such treatment a lysine methyltransferase, more preferably, a viral histone lysine methyltransferase, more preferably, a protein comprising a *Chlorella* virus SET domain of a viral histone lysine methyltransferase, and most preferably, a vSET or vSET-like viral histone lysine methyltransferase. "Decreasing or inhibiting the transcriptional expression of a target gene in the subject" encompasses decreasing the level of transcription of a target gene in at least some, but not necessarily all cells, tissues, and/or fluids of the subject. The subject to be treated can be a subject who does not exhibit a mutation in the gene targeted for transcriptional expression inhibition, but who would benefit from decreased transcriptional expression of the gene. The subject to be treated can also have a mutation in the gene targeted for transcriptional expression inhibition, wherein the subject exhibits increased transcription and protein levels relative to cells that normally express the wild-type gene product of that gene. In one embodiment, the subject is homozygous for the wild-type gene targeted for transcriptional expression suppression. In another embodiment, the subject is heterozygous for the wild-type gene and has a mutant genotype, for example, a null genotype, for the other allele of the gene targeted for transcriptional expression inhibition.

In Vitro Control of Host Cell Gene Expression:

In another embodiment, the present invention provides for methods of controlling the in vitro expression of a gene in a host cell, for example, by inhibiting cell proliferation and/or promoting apoptosis of a cell population, comprising administering to the cell population, a lysine methyltransferase which decreases the transcriptional expression of a target gene in the host cell. Inhibiting cell proliferation and/or promoting apoptosis means decreasing the number of cells in a population over a time interval, relative to a control population in which the transcriptional expression of a target gene has not been decreased.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. In one non-limiting embodiment, the host cell includes plant or mammalian host cells. Suitable cells include, but are not limited to, PC12 cells, CHO cells, HeLa cells, HEK-293 (also known as 293 cells) and 293T (human kidney cells), COS cells (e.g. COS-7 cells), mouse primary myoblasts, NIH 3T3 cells.

In a preferred embodiment, the host cell is a cell of a eukaryotic cell line, for example, but not limited to HeLa cell lines; breast cell lines; breast cancer cell lines such as MCF7 and MCF10A cell lines; prostate cancer cell lines such as PC3 and RWPE cell lines; leukemic cell lines such as K562, HL-60 and U937 cell lines; HEK-293T and COS cells.

Cancer Treatment:

In related embodiments, the present invention provides for methods of treating cancer, for example, by inhibiting tumor growth in a subject by inhibiting the expression of an oncogenic or tumorigenic gene, which comprises administering to the subject an effective amount of a lysine methyltransferase which decreases the level of transcriptional expression of a target gene in the subject. Examples of malignancies which may be treated according to the present invention include, but are not limited to, melanoma, glioblastoma multiforme, neuroblastoma, astrocytoma, osteosarcoma, breast cancer, cervical cancer, colon cancer, lung cancer, pancreatic cancer, Kaposi's sarcoma, hairy cell leukemia, nasopharynx cancer, ovarian cancer, and prostate cancer.

Treatment of Neurological Disorders:

The present invention also provides for methods of treating conditions such as degenerative disorders of the central nervous system (CNS), and peripheral nervous system (PNS), wherein the selective inhibition of a targeted gene or genes would be beneficial to a subject in need of treatment. For example, a disease that is associated with neuronal or glial cell defects including, but not limited to, neuronal loss, neuronal degeneration, neuronal demyelination, gliosis (i.e., astrogliosis), or neuronal or extraneuronal accumulation of aberrant proteins or toxins (e.g., β-amyloid, or α-synuclein). The neurological disorder can be chronic or acute. Exemplary neurological disorders include, but are not limited to, Gaucher's disease, Parkinson's disease, Alzheimer's disease, amyotrophic lateral sclerosis (ALS), multiple sclerosis (MS), Huntington's disease, Fredrich's ataxia, Mild Cognitive Impairment, Cerebral Amyloid Angiopathy, Parkinsonism Disease, Lewy Body Disease, Multiple System Atrophy (MSA), Progressive Supranuclear Palsy, and movement disorders (including ataxia, cerebral palsy, choreoathetosis, dystonia, Tourette's syndrome, kernicterus) and tremor disorders, and leukodystrophies (including adrenoleukodystrophy, metachromatic leukodystrophy, Canavan disease, Alexander disease, Pelizaeus-Merzbacher disease), neuronal ceroid lipofucsinoses, ataxia telangectasia and Rett Syndrome.

The present invention is not limited in scope to the treatment of a particular disease, or to the inhibition of a particular gene or class of genes associated with a disease state. The invention contemplates the treatment of any disease or disorder characterized by an increase in gene expression as compared to a non-disease state, or a condition that would benefit from the inhibition of one or more genes' expression. Such conditions may also include, but are not limited to, inflammatory disorders, auto-immune disorders, or arthritic disorders.

Molecular Biology Definitions

In accordance with the present invention there may be employed conventional molecular biology, microbiology, and recombinant DNA techniques within the skill of the art. These techniques are generally useful for the production of recombinant cells expressing lysine methyltransferase proteins. Such techniques are explained fully in the literature. (See, e.g., Sambrook, Fritsch & Maniatis, 2001, Molecular Cloning: A Laboratory Manual, Third Edition, Cold Spring Harbor Laboratory Press, Cold Spring Harbor, N.Y.; Glover, ed., 1985, DNA Cloning: A Practical Approach, Volumes I and II, Second Edition; Gait, M. J., ed., 1984, Oligonucleotide Synthesis: A practical approach; Hames, B. D. & Higgins, S. J. eds., 1985, Nucleic Acid Hybridization; Hames, B. D. & Higgins, S. J., eds., 1984, Transcription And Translation; Freshney, R. I., 2000, Culture of Animal Cells: A Manual of Basic Technique; Woodward, J., 1986, Immobilized Cells And Enzymes: A practical approach, IRL Press; Perbal, B. E., 1984, A Practical Guide To Molecular Cloning).

Recombinant Lysine Methyltransferase

The lysine methyltransferase useful for the methods of the present invention can be isolated and purified using molecular biology, microbiology, and recombinant DNA techniques known to those of ordinary skill in the art. For example, nucleic acids encoding the viral lysine methyltransferase can be isolated using recombinant DNA techniques known in the art. The nucleic acid encoding the lysine methyltransferase may be full-length or truncated, as long as the gene encodes a biologically active protein.

The identified and isolated gene encoding the viral lysine methyltransferase can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, E. coli, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Production of the recombinant protein can be maximized by genetic manipulations such as including a signal peptide at the N terminus to facilitate secretion or a 3' untranslated sequence containing a polyadenylation site.

In a preferred embodiment, the constructs used to transduce host cells are viral-derived vectors, including but not limited to adenoviruses, adeno-associated viruses, lentivirus, herpes virus, mumps virus, poliovirus, retroviruses, Sindbis virus and vaccinia viruses.

Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired.

Potential host-vector systems include, but are not limited to, eukaryotic cell systems, for example, mammalian cell systems infected with virus (e.g., vaccinia virus, adenovirus, lentivirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed, such as glycosylation, sialyation and phosphorylation. For example, expression in a bacterial system can be used to produce a nonglycosylated core protein product. Expression in eukaryotic cells can increase the likelihood of "native" protein. Moreover, expression in mammalian cells can provide a tool for reconstituting, or constituting, protein. Furthermore, different vector/host expression systems may affect processing reactions, such as proteolytic cleavages, to a different extent.

Purification of a recombinantly expressed protein can be achieved using methods known in the art such as by ammonium sulfate precipitation, column chromatography containing hydrophobic interaction resins, cation exchange resins, anion exchange resins, and chromatofocusing resins. Alternatively, immunoaffinity chromatography can be used to purify the recombinant protein using an appropriate polyclonal or monoclonal antibody that binds specifically to the protein, or to a tag that is fused to the recombinant protein. In a preferred embodiment, the purity of the recombinant protein used for the method of the present invention with be at least 95%, preferably 97% and most preferably, greater than 98%.

Formulations

A lysine methyltransferase, more preferably a viral histone lysine methyltransferase, more preferably a protein comprising a *Chlorella* virus SET domain of a viral histone lysine methyltransferase, and most preferably a vSET or vSET-like histone lysine methyltransferase, as described above, is advantageously formulated in a pharmaceutical composition together with a pharmaceutically acceptable carrier. The lysine methyltransferase may be designated as an active ingredient or therapeutic agent for the treatment of a disease or disorder that would benefit from a decrease in transcriptional expression of one or more genes.

The concentration of the active ingredient (lysine methyltransferase, more preferably a viral histone lysine methyltransferase, more preferably a protein comprising a *Chlorella* virus SET domain of a viral histone lysine methyltransferase, and most preferably a vSET or vSET-like histone lysine methyltransferase) depends on the desired dosage and administration regimen. An artisan of ordinary skill can determine the appropriate dosage using techniques that are routine in the art.

In one embodiment, the lysine methyltransferase may comprise a pharmaceutical formulation that is preferably suitable for parenteral administration, including intravenous, subcutaneous, intra-arteriolar, intramuscular, intradermal, intraventricular, intrathecal, intracranial and intraperitoneal injection, however, formulations suitable for other routes of administration such as oral, intranasal, or transdermal are also contemplated.

The pharmaceutical formulations suitable for injectable use include sterile aqueous solutions (where water soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like. In many cases, it will be preferable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating the purified lysine methyltransferase in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation contains an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation also preferably contains a non-ionic detergent. Preferred non-ionic detergents include Polysorbate 20, Polysorbate 80, Triton X-100, Triton X-114, Nonidet P-40, Octyl .alpha.-glucoside, Octyl .beta.-glucoside, Brij 35, Pluronic, and Tween 20.

The lysine methyltransferase formulation may be subject to lyophilization. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

Formulations for inhalation administration may contain lactose or other excipients, or may be aqueous solutions which may contain polyoxyethylene-9-lauryl ether, glycocholate or deoxycocholate. A preferred inhalation aerosol is characterized by having particles of small mass density and large size. Particles with mass densities less than 0.4 gram per cubic centimeter and mean diameters exceeding 5 μm efficiently deliver inhaled therapeutics into the systemic circulation. Such particles are inspired deep into the lungs and escape the lungs' natural clearance mechanisms until the inhaled particles deliver their therapeutic payload. (Edwards et al., Science 1997; 276: 1868-1872). Protein preparations of the present invention can be administered in aerosolized form, for example by using methods of preparation and formulations as described in, U.S. Pat. Nos. 5,654,007, 5,780,014, and 5,814,607, each incorporated herein by reference. Formulation for intranasal administration may include oily solutions for administration in the form of nasal drops, or as a gel to be applied intranasally.

Formulations for topical administration to the skin surface may be prepared by dispersing the composition with a dermatological acceptable carrier such as a lotion, cream, ointment, or soap. Particularly useful are carriers capable of forming a film or layer over the skin to localize application and inhibit removal. For topical administration to internal tissue surfaces, the composition may be dispersed in a liquid tissue adhesive or other substance known to enhance adsorption to a tissue surface. Alternatively, tissue-coating solutions, such as pectin-containing formulations may be used.

In preferred embodiments, the formulations of the invention are supplied in either liquid or powdered formulations in devices which conveniently administer a predetermined dose of the preparation; examples of such devices include a needle-less injector for either subcutaneous or intramuscular injection, and a metered aerosol delivery device. In other instances, the preparation may be supplied in a form suitable for sustained release, such as in a patch or dressing to be applied to the skin for transdermal administration, or via erodable devices for transmucosal administration.

Administration of the above-described parenteral formulations may be by periodic injections of a bolus of the preparation, or may be administered by intravenous or intraperitoneal administration from a reservoir which is external (e.g., an i.v. bag) or internal (e.g., a bioerodable implant, a bioartificial organ, or a population of implanted cells that produce the replacement protein). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered in these methods.

In a specific embodiment, the protein or vector therapeutic composition is delivered directly to the target tissue, e.g., a tumor, particularly for an unmodified lysine methyltransferase therapeutic product. This ensures that the effect is greatest where it is needed, and limits systemic side effects that might be undesirable.

EXAMPLES

The present invention is further described by means of the examples, presented below. The use of such examples are illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1 vSET and vSET-Like Proteins from
Chlorella Viruses Suppress Gene Transcription
Through Methylation of H3-K27

Methods
Growth of Virus and Preparation of Chlorella Cell Extracts
Growth of Chlorella NC64A on MBBM medium, the plaque assay, the production of the viruses, and the isolation of virus DNAs were carried out as described previously (Schuster, A. M. et al. Characterization of viruses infecting a eukaryotic chlorella-like green alga. Virology 150, 170-7 (1986)). Actively growing Chlorella NC64A cells ($3 \times 10^{10}$ cells in 150 ml) were mock infected or infected with virus PBCV-1 at a multiplicity of infection of 5 for various times. Purified PBCV-1 virus particles (200 μl of 6 mg/ml total virus) were treated with 200 U/ml sequencing grade modified trypsin (Promega) prior to further purification. This treatment has not effect on virus infectivity.
RNA Level Analysis of Infected Chlorella
Actively growing Chlorella NC64A cells ($1-2 \times 10^7$ per ml) were incubated with 5 μl/ml [$^3$H]-adenine (37 MBq/ml) for 10 minutes, centrifuged and cells were re-suspended in 50 mM Tris-HCl, pH 7.8, ($5 \times 10^7$ cells per ml) plus PBCV-1 at a multiplicity of infection of 10. One ml samples were collected at appropriate times and mixed with an equal volume of ice cold 10% trichloroacetic acid (TCA). Cells were collected on glass filters, washed three times with 5% TCA, one time with 80% ethanol and dried. RNA was hydrolyzed by placing the filters in 5 ml of 0.5 M NaOH overnight at 37° C., collected by filtering through a fresh filter, neutralized with TCA, and analyzed by scintillation counting. Total RNA was isolated from PBCV-1 infected Chlorella cells at various times post viral infection using the Trizol reagent (Invitrogen). Total RNA was electrophoresed and hybridized with a $^{32}$P-labeled gene probe using a Random-Primer DNA Labeling Kit (Invitrogen). Viral DNAs used for dot blots were denatured, applied to nylon membranes, fixed by UV cross-linking, and hybridized with a gene probe used for the Northern analysis.

DNA Cloning, Protein Purification, and Histone Methyltransferase Assay

Full-length histone H3 DNA from *Chlorella* NC64A was cloned by designing degenerate primers based on H3 from *Chlamydomonas reindardtii*. The SET gene was isolated from *chlorella* viruses MA-1D, NY-2A and NY-2B using an established protoco. (Kang, M. et al. Genetic diversity in *chlorella* viruses flanking kcv, a gene that encodes a potassium ion channel protein. Virology 326, 150-9 (2004)) The DNA bands that hybridized weakly with the PBCV-1 vSET probe were excised from the gel, recovered with a QIAEX II Gel Extraction Kit (Qiagen) and cloned into pGEM-7Zf (+). Primers were designed according to the vSET homologs identified from these hybridized DNA fragments. The vSET homologs from these three viruses were amplified by PCR and subcloned into pET-15b (Novagen). All DNA constructs and vSET mutants prepared using the QuikChange mutagenesis kit (Stratagene) were confirmed by DNA sequencing. Recombinant proteins were expressed in *E. coli* strain BL21. The in vitro histone methyltransferase reaction was performed by following methyl transfer from S-adenosyl-[$^{14}$C-methyl]-L-methionine (Amersham) to histone peptide or nucleosome substrates, or by mass spectroscopy analysis of the histone peptide substrates (Qian, C. et al. Structural insights of the specificity and catalysis of a viral histone H3 lysine 27 methyltransferase. J Mol Biol 359, 86-96 (2006)). Upstream and downstream primer sequences used for histine H3 are 5'-ATGGCCCGCACCAAG (SEQ ID NO:8) and 5'-TTAGGCGCGCTCGCC (SEQ ID NO:9), respectively.

Western Blot and Histone Immunoprecipitation Analyses

PBCV-1 infected *Chlorella* cells were harvested at different times post infection. Western blot analysis of the immunoprecipitated protein was done using anti-vSET antibodies, generated in rabbits against recombinant vSET (Covance). Histone immuno-precipitation was performed on *Chlorella* cells collected at 0-300 minutes post PBCV-1 infection. The assay was carried out by using anti-histone H3, H3-K27me1, H3-K27me2, H3-K27me3, H3-K27ac and H3-S28p antibodies (Millipore) with cells cross-linked with paraform-aldehyde and sheared by sonication. To assess the PcG proteins at H3-K27, HeLa cells stably transfected with vSET and treated with or without tetracycline, were subject to crosslinking and immunoprectipation using antibodies against EZH2 and Polycomb complex proteins, RING1, SUZ12, Ezh2/PRC2, Bmi/PRC1, CBX4, CBX7 and CBX8, and followed by Western blots using anti-H3 antibodies.

Nuclear Localization and Co-Localization vSET nuclear localization was analyzed in NIH-3T3 cells transiently transfected with a pEGFP-N1 vector (Clontech) that encodes a C-terminal GFP fusion vSET. The analysis includes fixation, permeablization and immunofluorescence. Typically, the exponentially growing cells were collected and suspended in 2% paraformaldehyde in PBS buffer of pH 7.4 at 4° C. for 6 hours. The fixed cells were pelleted by centrifugation, re-suspended in 5 ml chilled methanol, washed with PBS, and spotted onto a slide and air-dried. Cells adhered to the slides were incubated for 15 minutes at 4° C. in DMSO (0.5% vol/vol in PBS). For fluorescence analysis, cells were blocked with 0.5% bovine serum album in PBS and incubated with anti-vSET and anti-histone antibodies (Abcam) for 1 hour at 25° C. Cells were washed with PBS, and incubated with secondary fluorescein labeled antibody (Alexa 488), mounted with a cover slip and analyzed using a Zeiss Axioplan2 microscope. For the co-localization assay, staining was done with rabbit polyclonal anti-vSET and anti-rat monoclonal H3-K27me2 antibodies. The respective immune complexes were detected using Alexa488 and 594 (Molecular Probes).

Transcription Reporter Assay

A luciferase reporter gene transcription assay was performed as described previously (Nishio & Walsh, Proc Natl Acad Sci USA 101, 11257-62 (2004)). Briefly, 293T cells were co-transfected with 2 µg of pcDNA3-Ga14-DBD-vSET (or the mutants) and 1 µg of HSV-tk-promoter plus Gal4 binding sitre and luciferase gene constructs (e.g., pGL2-Ga14-E1b-Luc constructs). A luciferase assay on HOX7A promoter was also performed upon co-transfection with *Renilla* luciferase in Hela cells with and without EZH2 knockdown by siRNA, as described below. vSET repression of Tat-mediated transcription of a HIV LTR-luciferase gene was also evaluated. For this study, vSET and HIV Tat were transfected into HeLa (TZM-bl) cells that contain an integrated HIV LTR-luciferase reporter gene, or 293T cells with a HIV LTR-luciferase gene and HIV Tat with or without vSET (Derdeyn et al., J Virol 74, 8358-67 (2000); Mujtaba, S. et al., supra). After 48 hours, cells were lysed and assayed for luciferase activity using the Bright-Glo luciferase assay system (Promega). Each assay was done in duplicate and repeated five times. Chromatin immunoprecipitation (ChIP) analysis was also performed using EZ-ChIP kit (Millipore) to evaluate vSET repression of Tat-dependent HIV LTR-luciferase reporter gene transcription in Hela cells at the HIV promoter located in the nucleosome Nuc2 by using various antibodies for histone H3 of different modifications.

Cell Cycle Analysis

The vSET effect on the cell cycle was analyzed in NIH-3T3 cells transiently transfected with vSET in a pCMV-tag2B vector (Stratagene) and a Us9-GFP encoding plasmid, or HeLa cells stably co-transfected with vSET in a tetracycline-controlled vector pcDNA4/TO (Invitrogen) and the Us9-GFP plasmid. Post-transfection cells were treated with 1 µg of tetracycline (1 µg ml$^{-1}$), harvested after 24 hours by trypsinization, washed with PBS and fixed in chilled 70% ethanol in PBS. One hour before acquiring the data, cells were washed again with PBS and stained with propidium iodide (PI). Cell cycle analysis was performed with a Calibur flow cytometer (Becton Dickinson) after GFP and PI staining.

EZH2 RNAi Knockdown, CHIP, and Quantitative RT-PCR Analyses

RNAi knockdown of EZH2 was performed in Hela cells with target-specific and smart-pool siRNAs from Dharmacon. Cell transfection with siRNAs was done according to manufacturer's instructions. EZH2 RNAi knockdown was evaluated 72 hours after transfection by Western blot analysis using anti-EZH2 antibody (Cell Signaling). Methylation states of K4, K9, K27 and K36 on histone H3 were evaluated by using various antibodies obtained from Millpore and Abcam. Chromatin immunoprecipitation (ChIP) analysis was performed using EZ-ChIP kit (Millipore) to evaluate vSET repression of Tat-mediated transcription of the HIV LTR-luciferase reporter gene in Hela cells on the HIV promoter sequence in Nuc2 using various antibodies for histone H3 of different modifications. For RT-PCR analysis, RNA was extracted using RNAeasy kit (Qiagen) from Hela cells that were transfected with EZH2 siRNA and/or vSET. The primers for target genes of choice for analysis were designed based on the published sequences (Svingen et al.). cDNA was generated by RT-PCR using the affinity script from Stratagene. Reactions were determined usng the SYBR Green I detection chemistry system (Applied Biosystems) with an ABI Prism 7300 Sequence Detection System. Chromatin immuno-precipitation (ChIP) analysis was performed for the HOXA7 gene using the EZ-ChIP kit (Millipore) following the manufacturer's instruction as previously described (De Santa et al., Cell 130:1083-1094 (2007)).

Dot Blot for Antibody Specificity

Dot blot assay was performed on 0.2 μm nitrocellulose paper (GE Healthcare; catalog #RPN3032D). Histone peptides (500 μM each) were spotted on the nitrocellulose paper and dried for 1 hour at room temperatures. Subsequently, the membrane was blocked for 1 hour at room temperature with 2% non-fat milk in TBS buffer. After blocking, the membrane was washed with TBS, and treated with respective antibodies for 2 hours at room temperature. After antibody exposure, the membrane was washed three times for 5 minutes each with TBS containing 0.05% Tween-20. Finally, the membrane was treated with secondary antibody (GE Healthcare; catalog #NA9340V) for 1 hour at room temperature. After washing three times for 5 minutes each with the TBS Tween-20 buffer the membrane was exposed to ECL reagent (GE Healthcare; catalog #RPN2106) (Huang et al., Nature 449:105-108 (2007); Erhardt et al., Development 130:4235-4248 (2003); and Rougeulle et al., Mol Cell Biol. 24:5475-5484 (2004)).

Histine as the Major Target of vSET

Heat inactivated cell extracts from EZH2-knockdown HeLa and *chlorella* cells were subjected to vSET enzyme assay, and subsequently analyzed with western blot by using anti-H3, H3K27me2, H3K9me2, H3K4me2, and Pan-methylated lysine (Pan-Kme) antibodies. After antibody exposure, the membrane was washed three times for 5 minutes each with TBS buffer containing 0.05% Tween-20. The membrane was treated with secondary antibody (GE Healthcare; catalog #NA9340V) for one hour at room temperature. Finally, after washing three times for 5 minutes each with the TBS buffer the membrane was exposed to ECL reagent (GE Healthcare; catalog #RPN2106).

Luciferase Reporter Gene Assay

Figures 4A, 4B:
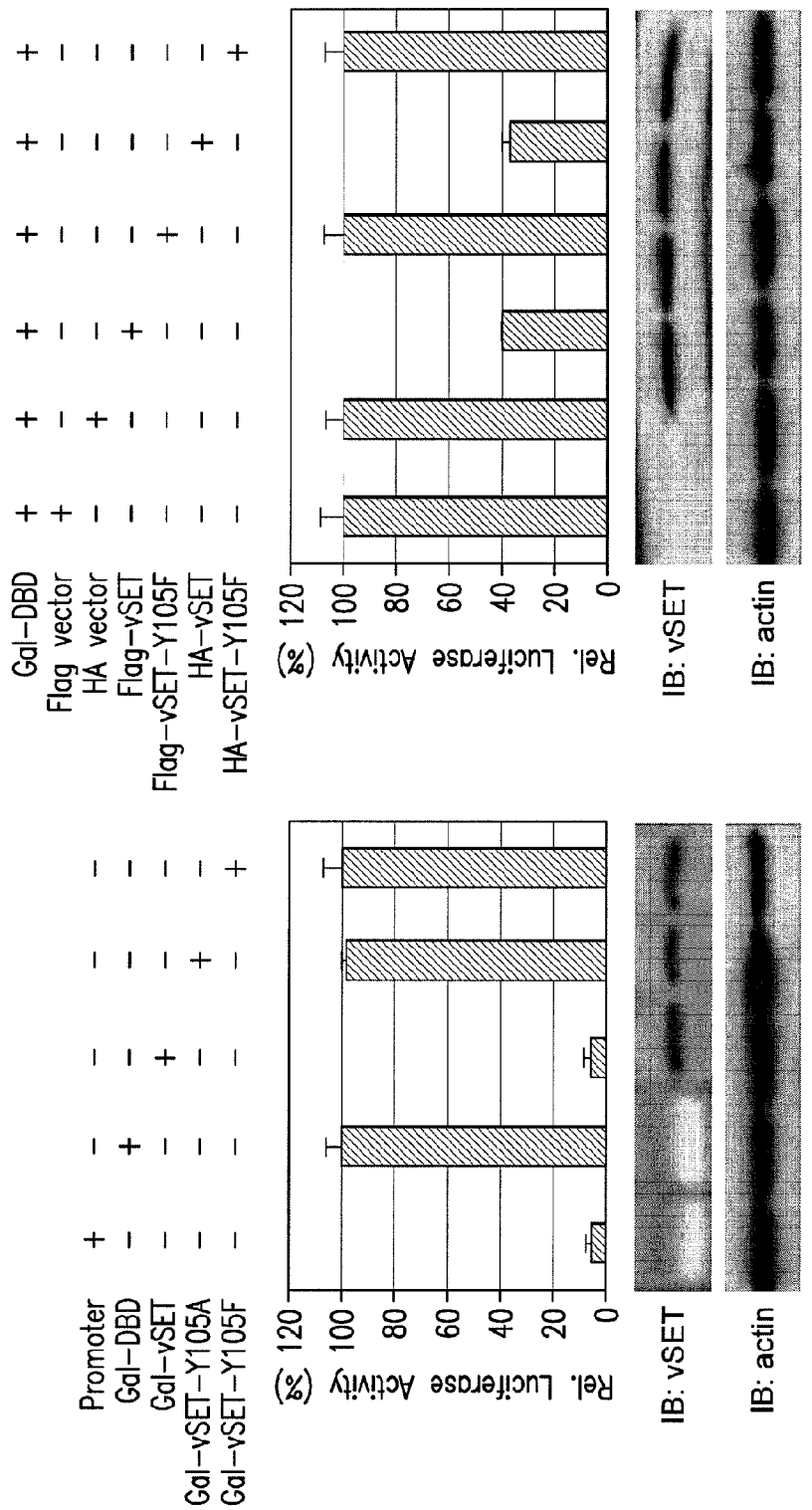
FIGS. 4a-4j show targeted and global gene transcription repression by vSET via its histone H3-K27 methylation activity. a, Transcription repression of a reporter luciferase gene by vSET and its active site mutant in transiently transfected 293T cells, in which vSET was fused to the Gal4-DNA binding domain. The error bars represent the standard deviation of triplicate assays. b, Transcription repression of the reporter luciferase gene by Flag- or HA-tagged vSET and its active site mutant in transiently transfected 293T cells. This assay shows the global effect of the luciferase repression by vSET H3-K27 methylation activity, as vSET is not fused Gal-DBD as in a. c, vSET repression of Tat-mediated transcription of a HIV LTR-luciferase reporter gene in transfected HeLa cells. d, CHIP analysis of vSET repression of Tat-mediated transcription of the HIV LTR-luciferase reporter gene in transfected Hela cells on the HIV promoter sequence in Nuc2 using various antibodies against histone H3 with different modifications. GADPH and IgG were used as control. e, Western blot analyses of association of the Polycomb group repression complexes 1 and 2 (PRC1 and PRC2) proteins with H3-K27 of different modifications upon induction of stably transfected vSET in HeLa cells with EZH2 knock-down by siRNA. The inactive vSET-Y105F mutant was used as control. f, Quantitative RT-PCR measurements showing relative mRNA levels of five Polycomb target genes of Hey1, HOXA9, HOXD8, HOXB9, and HOXA7, and three house keeping genes of GAPDH, RPS, and Tubulin in normal HeLa cells, and EZH2 knocked-down HeLa cells with or without induction of the transiently transfected vSET, as well as HeLa cells transfected with vSET. g, vSET induces G2/M phase cell accumulation in NIH-3T3 cells transiently co-transfected with a vSET-encoding pCMV-tag2B vector and a marker Us9-GFP-encoding plasmid. Western blots showing relative equal expression of vSET and its mutants. h, vSET expression induces G2/M arrest in stably transfected HeLa cells with tetracycline control. The DNA content of the gated GFP-positive cells was determined by PI staining and FACS analysis. Average values of the DNA content of cell cycle phases represent at least three independent transfection experiments. i, Repression of HOXA7 activation in the HeLa cells with or without EZH2 knockdown by tetracycline induced vSET in a luciferase assay. j, ChIP analysis at the HOXA7 promotor upon induction of vSET in the HeLa cells with and without EZH2 siRNA treatment.

Gene repression activity by vSET was measured in transient transfection luciferase reporter gene assay in 293T cells. The constructs used in the study presented in FIG. 4a are Gal4-DBD (aa 1-147), Gal4-DBD-vSET, Gal4-DBD-vSET-Y105A and Y105F, Gal4-tk-luciferase and *renilla* luciferase, and in FIG. 4b are Gal4-DBD (1-147), Flag-vSET and Flag vSET-Y105F, and HAvSET and HA-vSET-Y105F. The results are presented as relative luciferase expression in the presence of GA4-DBD-vSET as compared to that with GAL4-DBD alone. The reporter luciferase gene is linked to a Gal4-tk-luciferase promoter construct. Luciferase activity levels were determined using the dual luciferase kit (Promega) and data were normalized to the activity of a co-transfected *renilla* luciferase plasmid (Promega). HOXA7 luciferase was performed by co-transfecting HeLa cells with HOXA7 promoter and *renilla* luciferase in the presence or absence of EZH2. HOXA7 promoter was a gift from Drs. R. Slaney and K. Kamps. Both GAL4 and HOXA7 luciferase assays were performed on three different days. The error bars represent the standard deviation of luciferase levels measured in three different data sets.

Results vSET is a Structural Protein of PBCV-1 Virions

*Paramecium bursaria chlorella* virus 1 (PBCV-1) is a large dsDNA virus that replicates in the unicellular, eukaryotic, green alga *Chlorella* strain NC64A; *Chlorella* species are one of the most widely distributed and frequently encountered groups of algae on earth (Van Etten, Annu Rev Genet 37, 153-95 (2003)). The 330-kb PBCV-1 genome has 366 non-overlapping protein-encoding genes and 11 tRNA genes that have a mosaic of prokaryotic- and eukaryotic-like proteins (Van Etten, 2003.). Despite its large genome, the virus lacks a recognizable RNA polymerase gene, suggesting that it is dependent on host enzyme(s) for transcription. Notably, PBCV-1 infection results in a rapid decrease in total RNA synthesis reaching 60-80% inhibition 20-40 minutes post infection (FIG. 1a). Rapid transition from host to virus transcription occurs as PBCV-1 transcripts can be detected 5-10 minutes post infection (Van Etten, 2003). These results lead to the postulation that a factor(s) packaged in the virion might be responsible for the rapid inhibition of host RNA synthesis. vSET is a good candidate for such a factor, because vSET methylates H3-K27 (see below), which has been linked in eukaryotes to the PcG complex-mediated Hox gene silencing (Czermin et al., Muller, J. et al., Cao et al., Kuzmichev et al., Plath, K. et al., Boggs, B. A. et al., Bernstein, B. E. et al., Boyer, L. A. et al., Lee, T. I. et al. Cao & Zhang; supra).

Figure 1B:
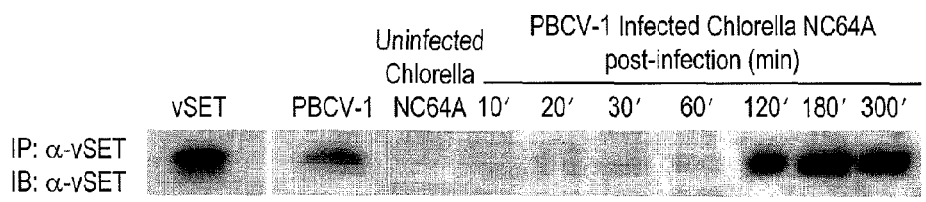
Figure 1C:
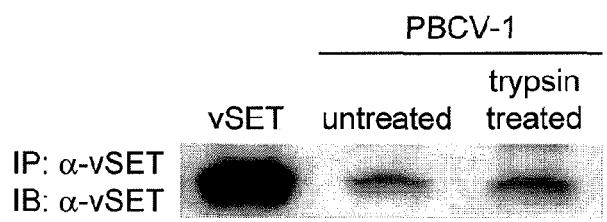
Figure 1D:
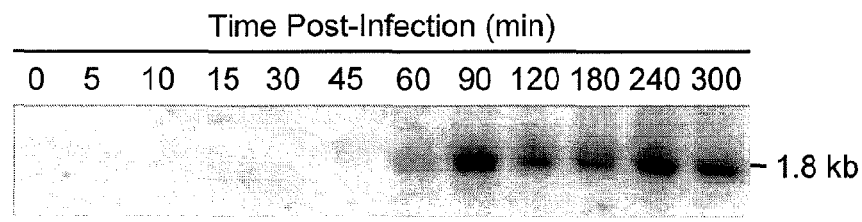
Figure 1E:
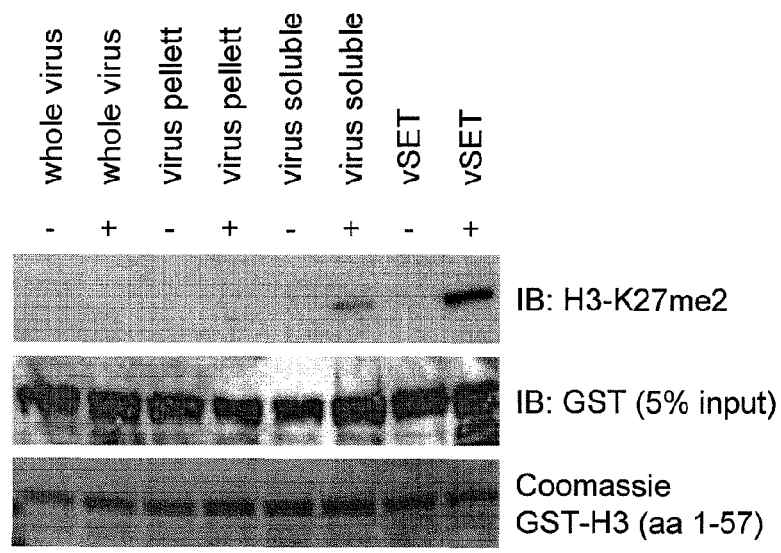

To investigate the role of vSET in PBCV-1 infection, an anti-vSET antibody was produced and used to immunoprecipitate vSET from viral infected *Chlorella* cell extracts. As shown in FIG. 1b, vSET is present in mature virions and a small amount is detected in virus infected *Chlorella* cells as early as 10 minutes post infection; vSET appears in large quantities by 120 minutes after virus infection. Trypsin treatment of intact PBCV-1 particles eliminated the possibility that vSET is a contaminant on the virion surface (FIG. 1c). The presence of vSET in PBCV-1 virion particles was also confirmed by Q-TOF mass spectrometry (Dunigan, Cerny and Van Etten, unpublished results). Comparing western blots from a known number of virus particles with blots containing different concentrations of vSET led to abn estimation that four vSET molecules are packaged per virion (data not shown). Furthermore, vSET in the disrupted virions shows histone H3-K27 methylation activity (FIG. 1e). Therefore functional vSET is packaged in the virions.

To determine when vset is transcribed during PBCV-1 replication, RNA from infected *Chlorella* cells was probed with the vset gene. The probe hybridized to an RNA of ~1.8 kb beginning at ~60 minutes post infection (FIG. 1d). This transcript is larger than expected for a 119-residue protein and may be a bicistronic transcript encoding the co-linear genes a609l (~1.2 kb) and a6121 (~0.4 kb). The latter gene encodes vSET. This Northern result is consistent with vSET expression occurring ~120 minutes after virus infection (FIG. 1b). The observation that vset is expressed as a late gene agrees with the finding that vSET is present in mature PBCV-1 virions because virion associated proteins are usually late gene products (Van Etten, 2003).

Figure 2C:
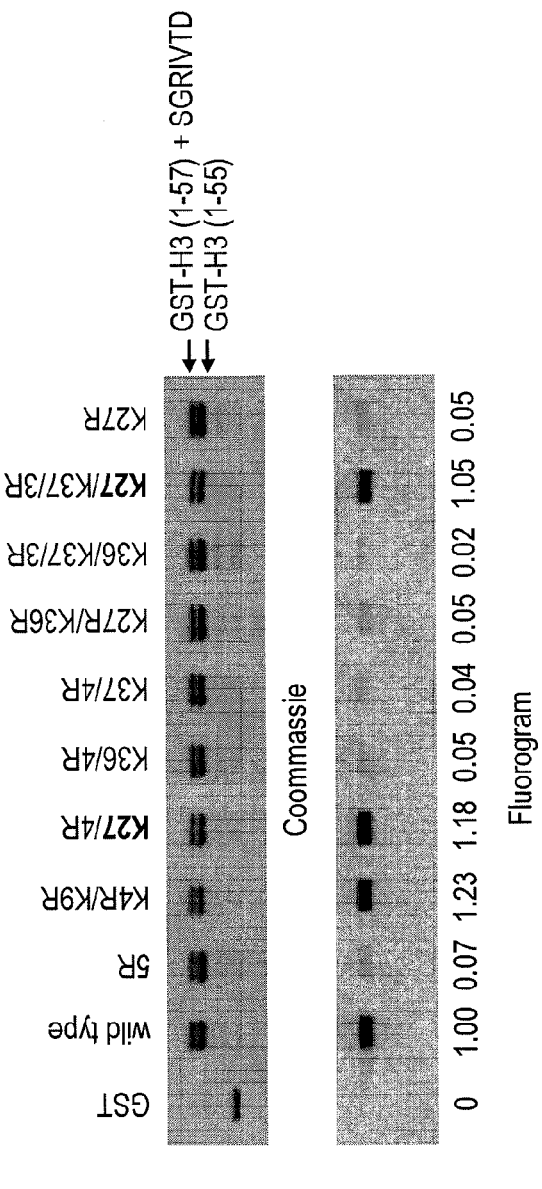
Figure 2B:
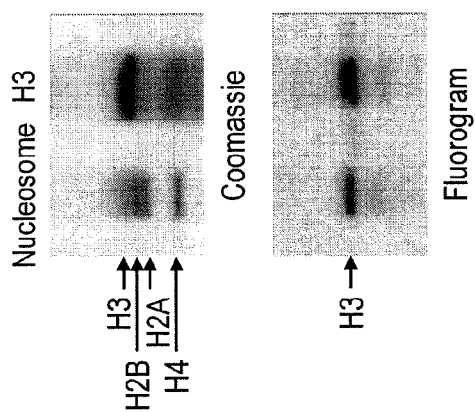
Figures 2D, 2E:
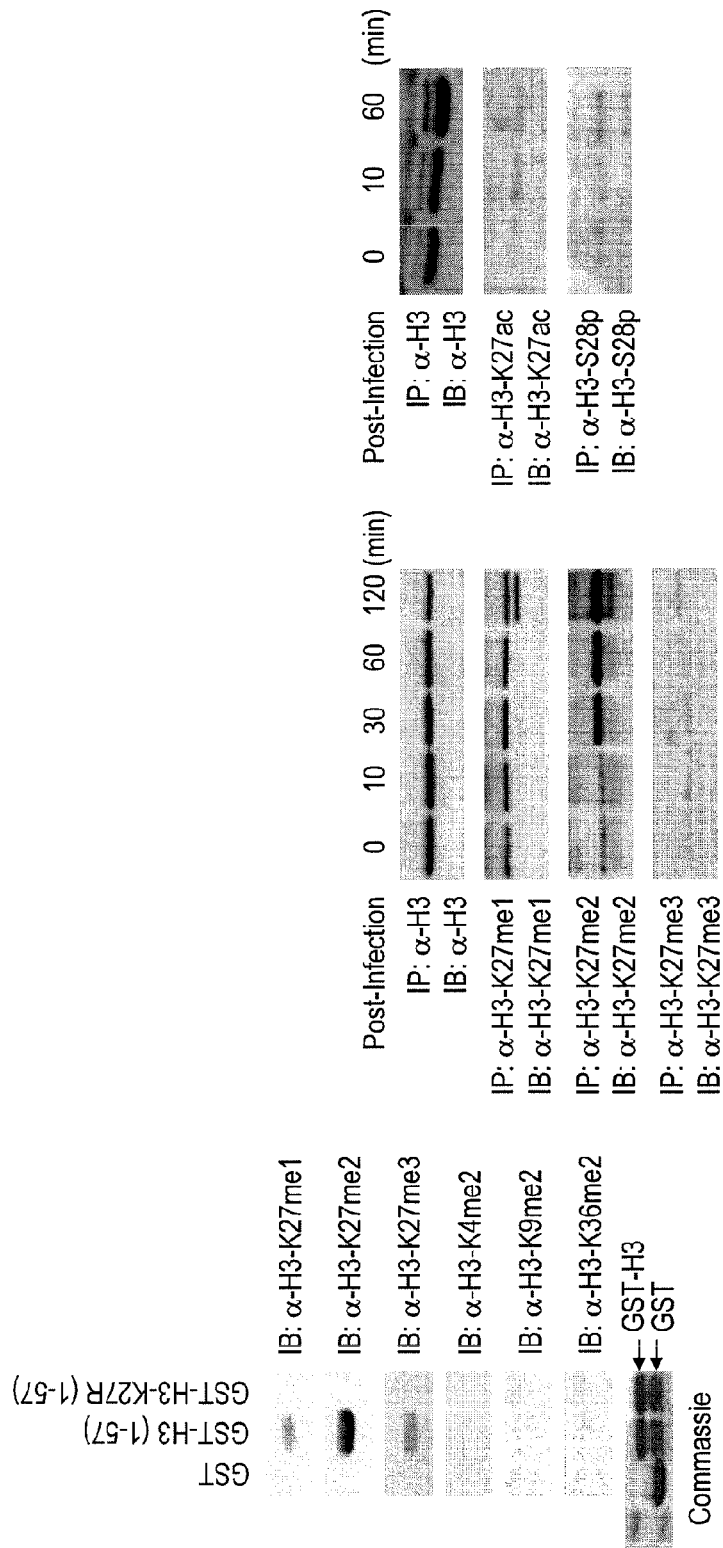
Figure 2F:
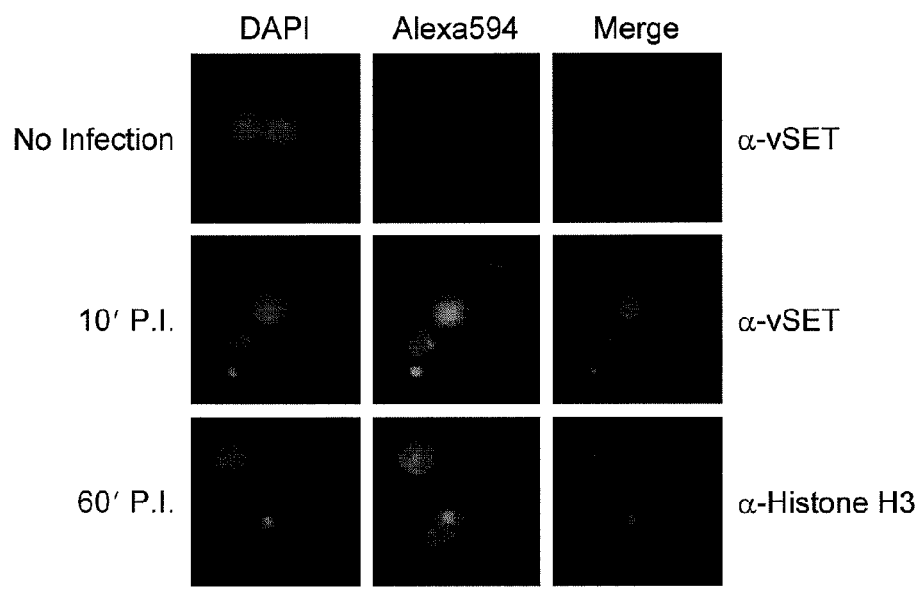
Figure 2G:
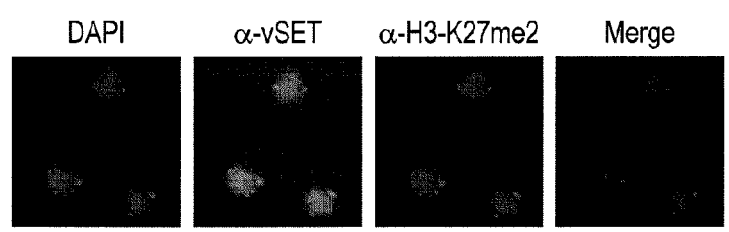
Figure 2H:
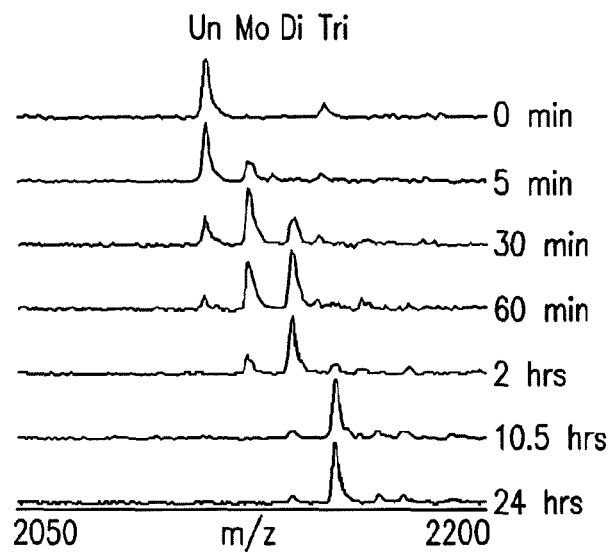
Figure 2I:
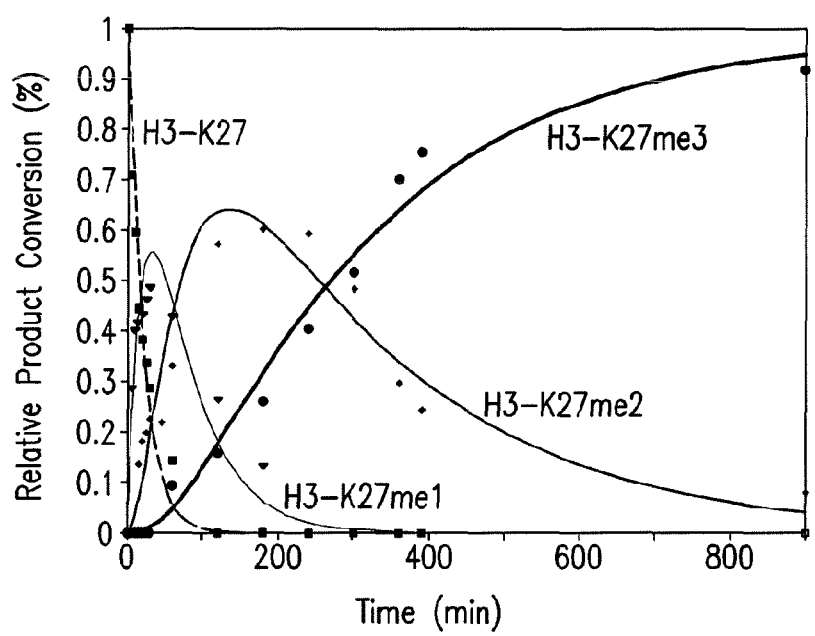

PBCV-1 vSET is a Bona Fide HKMTase vSET adopts a core beta-barrel structure, a fold that is conserved in eukaryotic SET domain HKMTases (Manzur et al., Qian et al., Qian & Zhou, supra). To test whether vSET is a bona fide HKMTase of the host *chlorella*, histone H3 from *Chlorella* NC64A was cloned and sequenced. The *Chlorella* H3 has high sequence identity to H3 from human, mouse, *Caenorhabditis elegans* as well as the green alga *Chlamydomonas reinhardtii* (FIG. 2a). vSET methylation activity was measured using both the nucleosome and individual core histones, confirming its activity for full-length free H3 and H3 within the nucleosome, but not other core histones (FIG. 2b). To identify vSET methylation site(s) in H3, a series of GST-H3 peptides were prepared (residues 1-57) with arginine substitutions at lysine methylation sites, K4, K9, K27, K36 and K37. The purified GST-H3 peptides produced two bands when electrophoresed on SDS-PAGE that corresponded to an intact H3 peptide of residues 1-57 (plus SGRIVTD (SEQ ID NO:53) from the expression vector) and a truncated H3 of residues 1-55, as confirmed by MALDI-TOF mass spectrometry (FIG. 2c). The methylation assay showed that vSET was only active when H3 contained K27 (FIG. 2c). Using antibodies against site- and state-specific lysine methylated histone H3, it was confirmed that vSET can predominately catalyze di-methylation at H3-K27 and to a much less extent mono- and tri-methylation, and not methylation at K4, K9 or K36 in H3 (FIG. 2d). The former is consistent with the enzyme kinetics analysis of vSET methylation of H3-K27 peptide, showing that mono-methylation and mono- to di-methylation are very rapid whereas di- to tr-methylation is ~10 times slower than mono- to di-methylation (FIGS. 2H and 2I). Collectively, these results clearly show that vSET is H3-K27 specific di-methylase.

Possible changes in H3-K27 in *Chlorella* NC64A cells after PBCV-1 infection were examined. As revealed by Western blot analysis using antibodies specific for histone H3 with different modifications (FIG. 6a-e), host H3-K27me1 was largely unchanged after viral infection, whereas H3-K27me2 was increased markedly as early as 30 minutes after viral infection, and H3-K27me3 was enhanced slightly (FIG. 2e). This observation correlates well with in vitro vSET state-specific methylation activity at H3-K27 (FIG. 2d). As illustrated by immunofluorescence, vSET was present in the nucleus of the host *Chlorella* cells after PBCV-1 infection (FIG. 2f), and vSET co-localized with the host H3 that became di-methylated at K27 (FIG. 2g).

vSET Contains a Nuclear Localization Signal

Due to the technical difficulties of manipulating the PBCV-1 genome and genetic transformation of the host *chlorella* cells, it is not possible currently to conduct a cellular study of vSET in its native host. However, because of the highly conserved H3 sequence and H3-K27 methylation in eukaryotes, it was reasoned that mammalian cells could serve as a suitable model system to study the biological function of vSET, which as similar enzymatic activity as EZH2 (Cao et al, supra.).

Figure 3A:
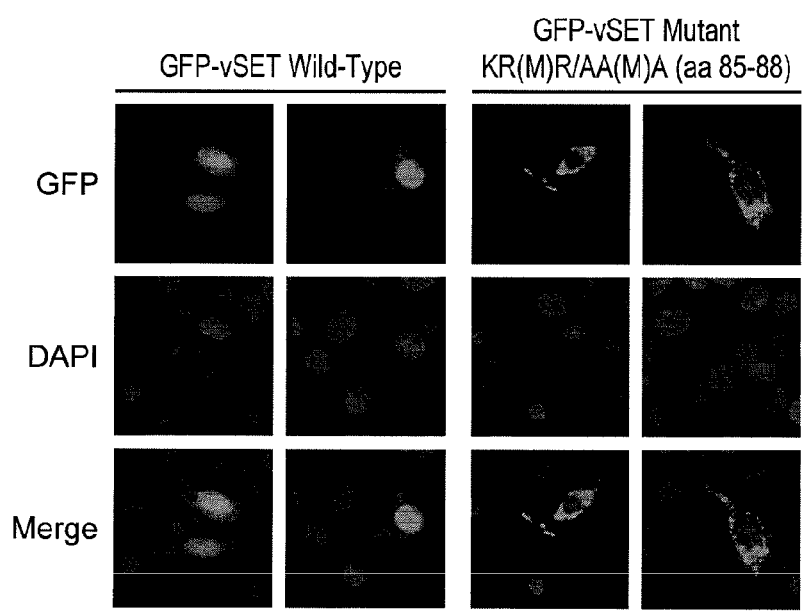
Figure 7A:
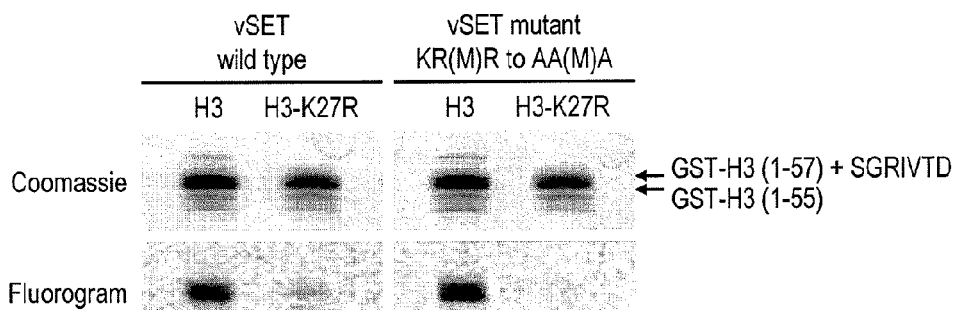
FIGS. 7a-7c show that a triple mutation in vSET, KR(M)R (SEQ ID NO:3) -to-AA(M)A (SEQ ID NO:4) (aa 85-88), does not disrupt the overall fold of the protein or its HKMTase activity. a, GST-fusion H3 (residues 1-57), wild-type and the K27R mutant, were used as substrates in an in vitro HKMTase assay and the relative amounts of GST-H3 used in the assay are shown in an SDS-PAGE gel (upper panel). Signals in the fluorogram indicate that similar to wild-type vSET, the triple mutant, methylated wild-type GST-H3 (aa 1-57) but not the K27R mutant. This indicates that the triple mutation in vSET did not affect the enzyme activity and specificity of vSET for H3-K27. b & c, Gel filtration chromatography verified that the triple mutation of vSET did not affect the overall fold of the protein. Hexahistidine tagged vSET, wild-type and mutant, eluted as about 30 kDa proteins, which is the approximate value of a hexahistidine tagged vSET dimer, MW of 31.6 kDa. The protein standards used were ribonuclease A (14 kDa), chymotrypsin (25 kDa) and ovalbumin (43 kDa).
Figure 7B:
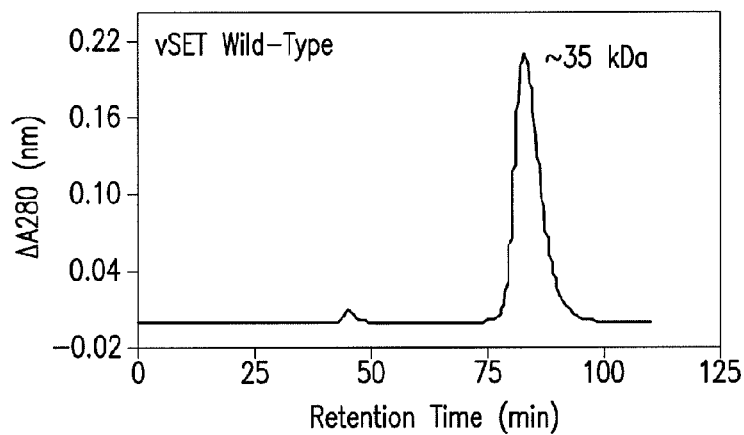
Figure 7C:
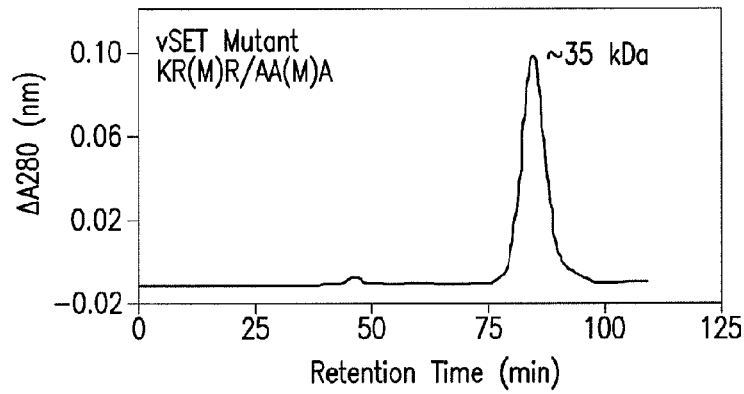
Figure 11:
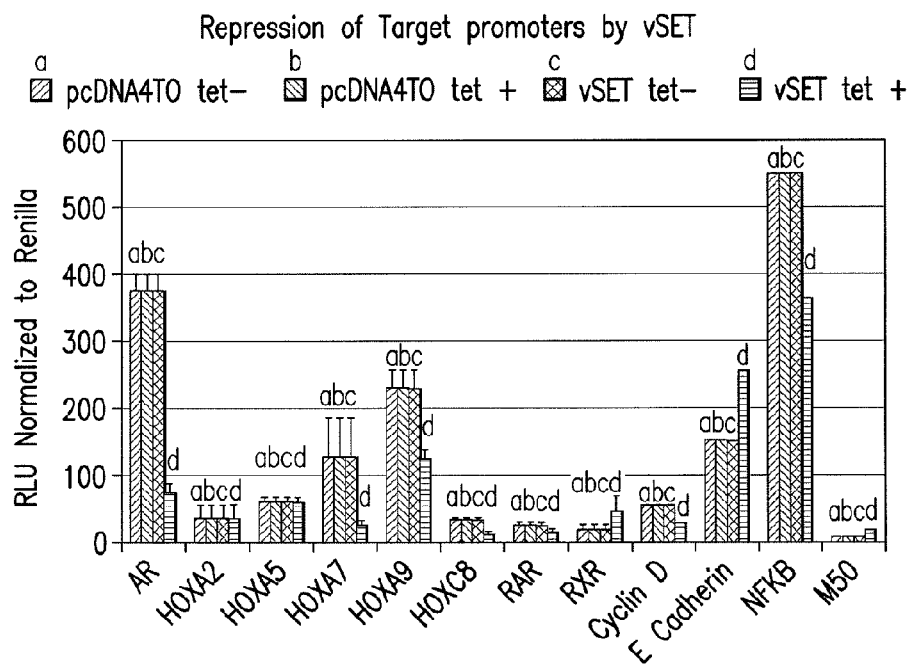
FIG. 11 shows the transcriptional silencing of disease related genes by vSET.
Figure 12:
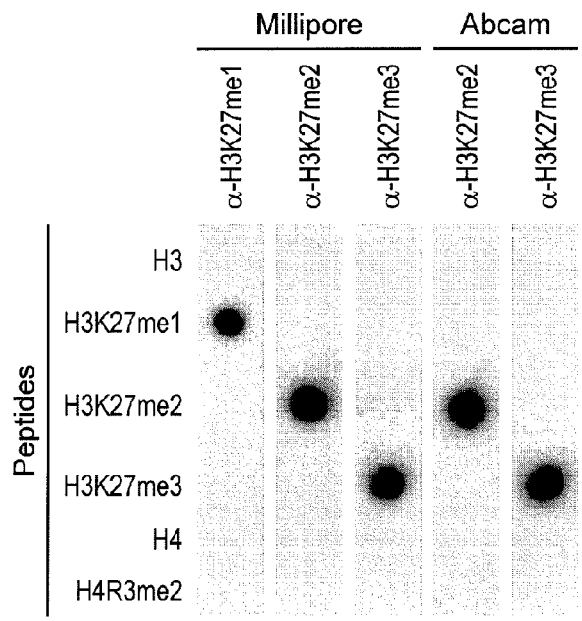
FIG. 12 shows histone H3K27 methylation by vSET. Western blot analyses of H3 modification-specific antibodies using synthesized histone peptides containing specific modified amino acids as stated.
Figure 13A:
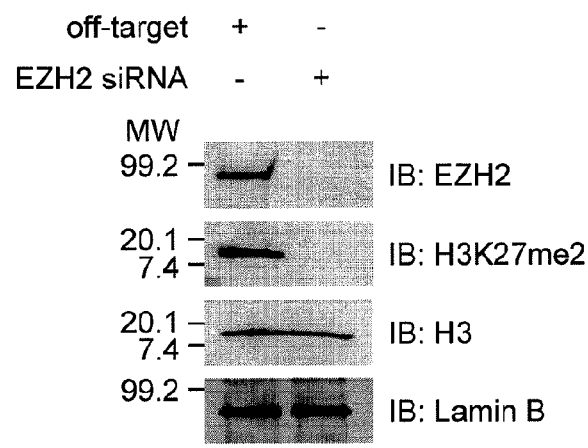
FIGS. 13a-13d show Histone H3K27 as the major substrate by vSET. a, EZH2 knockdown in HeLa cells by RNAi and loss of dimethylation at histone H3K27. b, Strategy for the EZH2 RNAi experiment. c, SDS-PAGE and western blot analysis of cellular extracts of EZH2-knockdown HeLa cells and *chlorella* cells using H3, H3K27me2, H3K9me2, and H3K4me, and Pan-Kme antibodies. d, Broad methylated-lysine specific recognition by the Pan-Kme antibody.
Figure 13B:
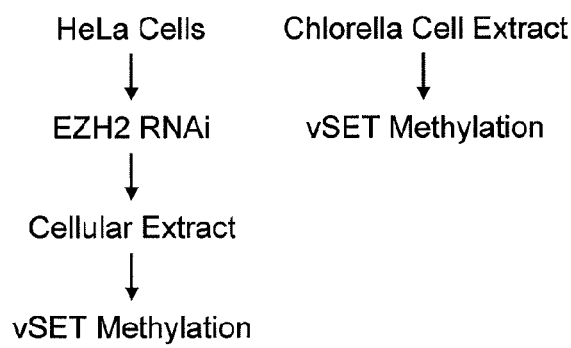
Figure 13C:
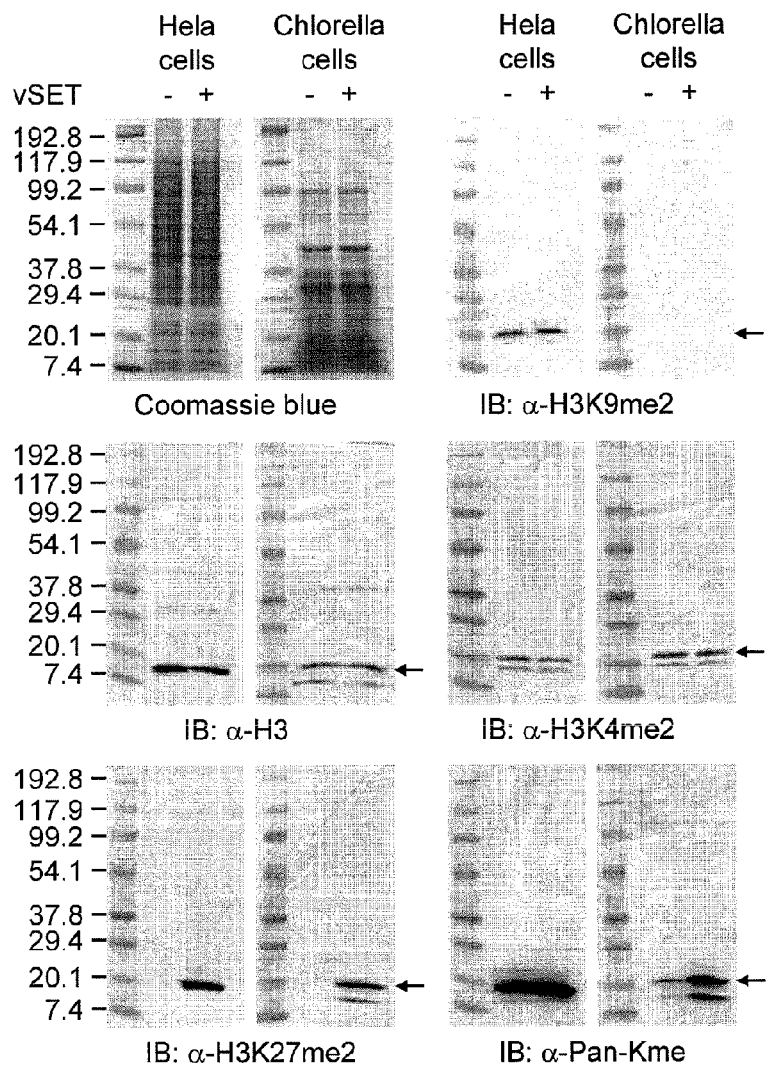
Figure 13D:
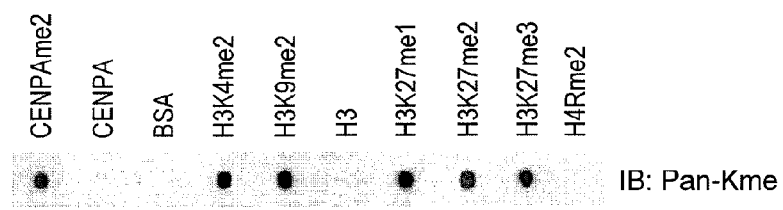
Figure 14A:
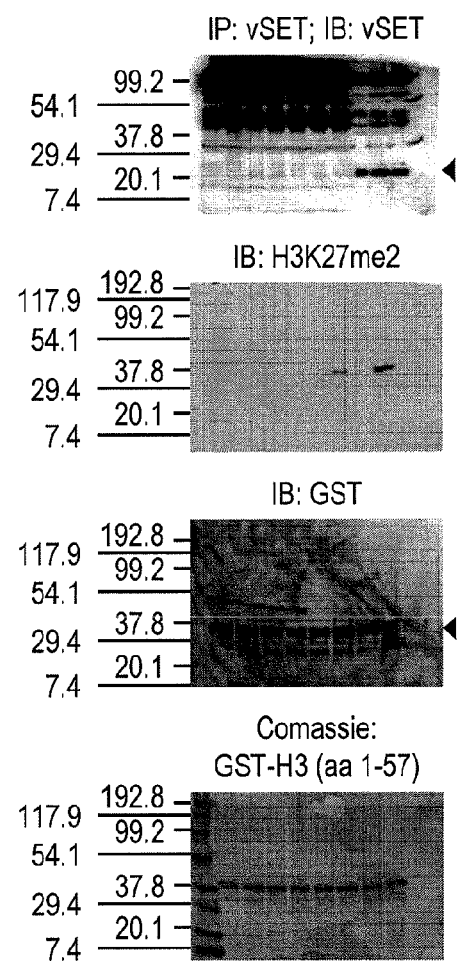
FIGS. 14a-14d show full scans of key western blots of FIGS. 1B, 2D, 2E, 3D, 4A, 4B and 4E. Arrowheads show specific bands in cropped images.
Figures 14B, 14C:
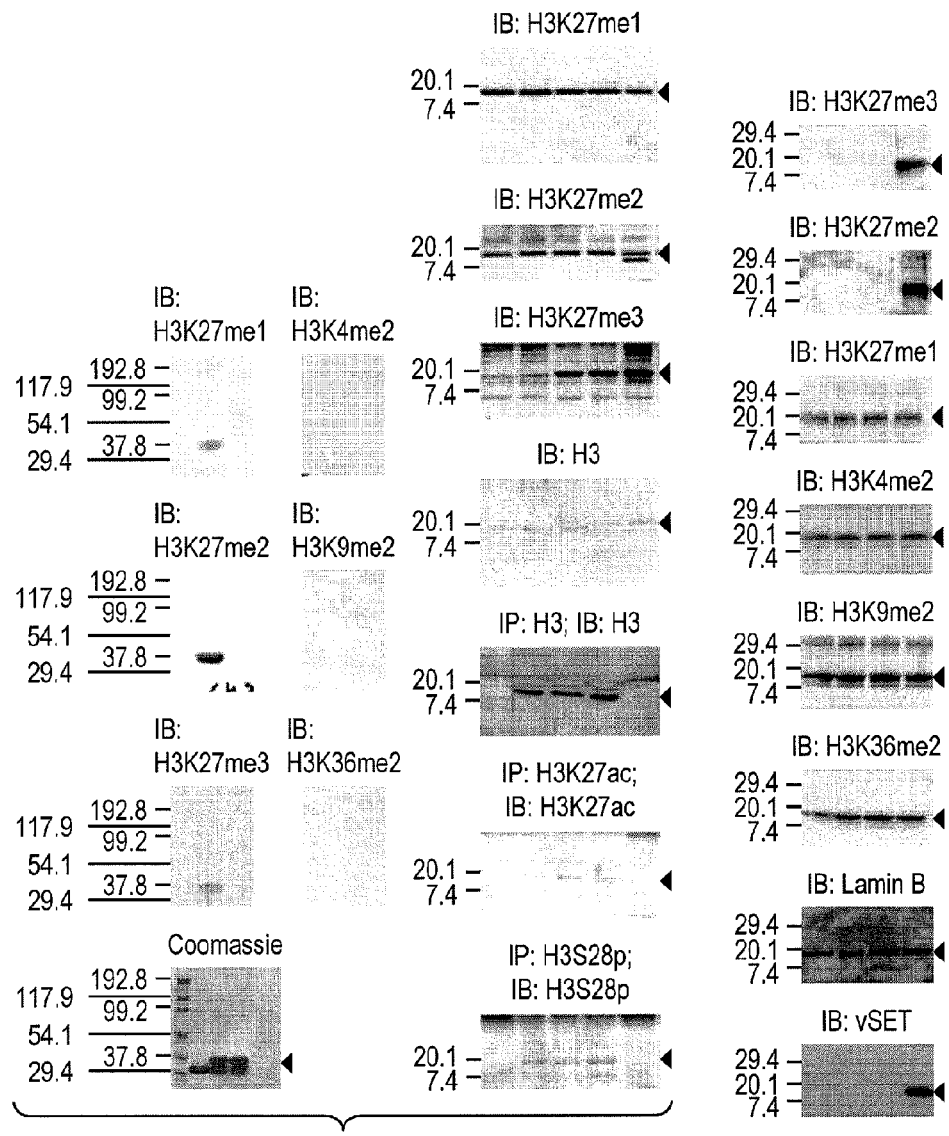
Figure 14D:
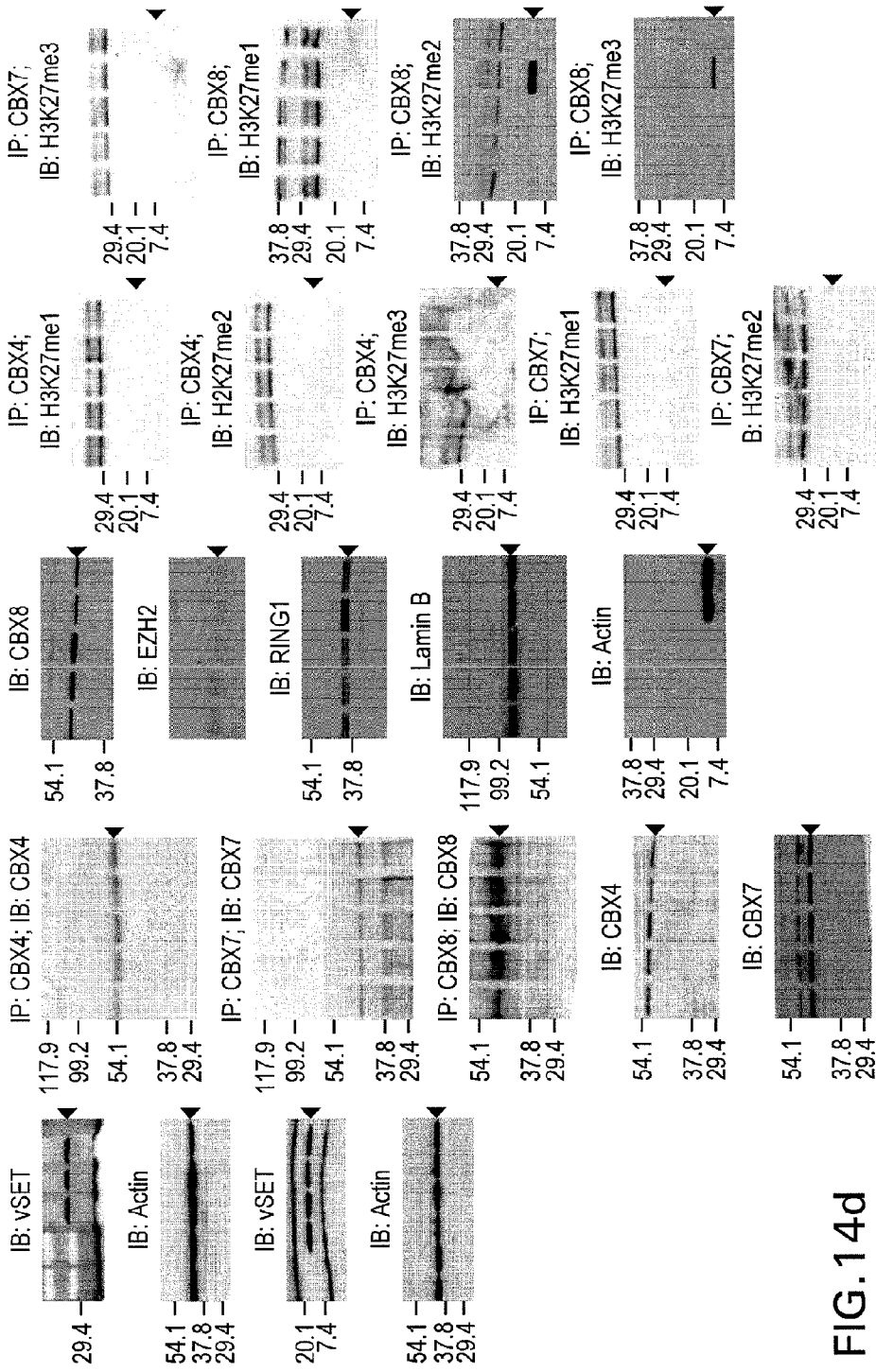
Figure 17:
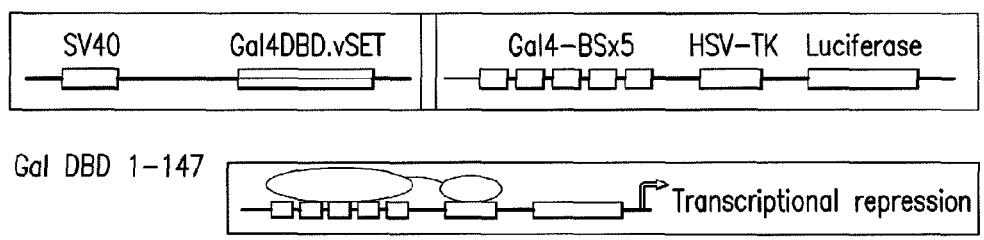
FIG. 17 shows a schematic representation of the luciferase reporter gene constructs used in the experiments of the application as described in FIGS. 4a and 4b.

For vSET to participate in early suppression of host transcription, it must move to the host nucleus immediately after viral infection. To assess whether a solvent-exposed KRMR (SEQ ID NO:3) motif in vSET (residues 85-88, FIG. 5b) functions as a nuclear localization signal (NLS), NIH-3T3 cells were transfected with either a GFP-fusion vSET or a triple mutant where KR(M)R (SEQ ID NO:3) was changed to AA(M)A(SEQ ID NO:4). Immunofluorescence showed that wild-type GFP-vSET was localized to the nucleus, whereas the triple mutant was in the cytoplasm (FIG. 3a), confirming that the KR(M)R (SEQ ID NO:3) motif is an NLS in vSET. It was established that H3-K27 methylation activity and vSET protein conformation was not compromised in this mutant (FIG. 7a-c). Note that a classical NLS sequence is absent in most eukaryotic SET domains, except for yeast SET1 that has a RRIV (SEQ ID NO:54) motif located at a site analogous to the KRMR (SEQ ID NO:3) motif in vSET. Viral proteins such as human adenovirus-5 E1A protein and bovine herpesvirus-1 VP8 protein contain basic KRPR (SEQ ID NO:6) and RRPR (SEQ ID NO:7) patches, respectively, indicating that putative NLS signals are encoded in virus proteins (Douglas, J. L. & Quinlan, M. P. Structural limitations of the Ad5 E1A 12S nuclear localization signal. Virology 220, 339-49 (1996); Zheng et al., Characterization of nuclear localization and export signals of the major tegument protein VP8 of bovine herpesvirus-1. Virology 324, 327-39 (2004)).

vSET Mimics Mammalian EZH2 for H3-K27 Methylation

To investigate whether vSET can methylate H3-K27 in mammalian cells, RNAi knockdown of EZH2 was performed. As shown in FIG. 3b, EZH2 expression was reduced by greater than 90% in Hela cells after treated with EZH2-specific siRNA as compared to control. EZH2 knockdown also resulted in a marked reduction of SUZ12, a component of the PRC1 complex, as well as a nearly complete loss of H3-K27me2 and K27me3 and a little effect on H3-K27me1. No significant change was observed with H3-K4, H3-K9 and H3-K36 di-methylation. These results confirm that EZH2 is responsible for H3-K27 di- and tri-methylation in Hela cells. vSET treatment of the nuclear extract of the EZH2 knocked-down Hela cells restore H3-K27me2 and K27me3, and results in a slight reduction of H3-K27me1, possibly due to its conversion to H3-K27me2 and K27me3 by vSET (FIG. 3c). There was no change in the level of H3-K4, K9 and K36 methylation. These results are similar to effects of tetracycline-induced vSET expression in the EZH2 knocked-down Hela cells (FIG. 3d). Taken together, the results strongly demonstrate that vSET can mimic EZH2 of the PRC2 complex for methylating H3-K27 in mammalian cells.

vSET Induces Gene Silencing

The effect of vSET methylation activity on host transcription was examined using a luciferase reporter assay in human embryonic kidney 293T cells. The study was first carried out with the 293T cells transfected with vSET fused to a Gal4 DNA-binding domain (DBD) and a luciferase reporter gene encoding HSV-tk promoter (plus Gal4 DNA-binding sites). As shown in FIG. 4a, wild-type vSET caused ~95% repression of the luciferase gene expression, whereas its inactive mutant Y105A or Y105F completely lost vSET gene silencing ability. Moreover, expression of a Flag- or HA-tagged vSET in the 293T cells exhibited ~60% repression as compared to the vectors containing only Flag- or HA-tag, or inactive mutant Y105F (FIG. 4a). The less profound Flag- or HA-tagged vSET repressive activity (a global effect) on host transcription as compared to that of vSET fused directly to Gal4-DBD (a targeted effect) may be in part due to the existence of H3-K27 acetylation and/or H3-S28 phosphorylation in host cells that would preclude H3-K27 methylation by vSET. Finally, it was observed that expression of a Flag-tagged vSET co-transfected with HIV Tat in 293T cells (FIG. 6d) or HeLa cells (FIG. 6e) causes transcription repression of a Tat-mediated HIV LTR-luciferase gene in a dose-dependent manner, thus confirming that vSET methylation activity represses chromatin-mediated gene transcription. (Mujtaba, S. et al., Dorr, A. et al., supra).

vSET Promotes PRC1 CBX8 Recruitment to 113-K27me Site

Figure 4C:
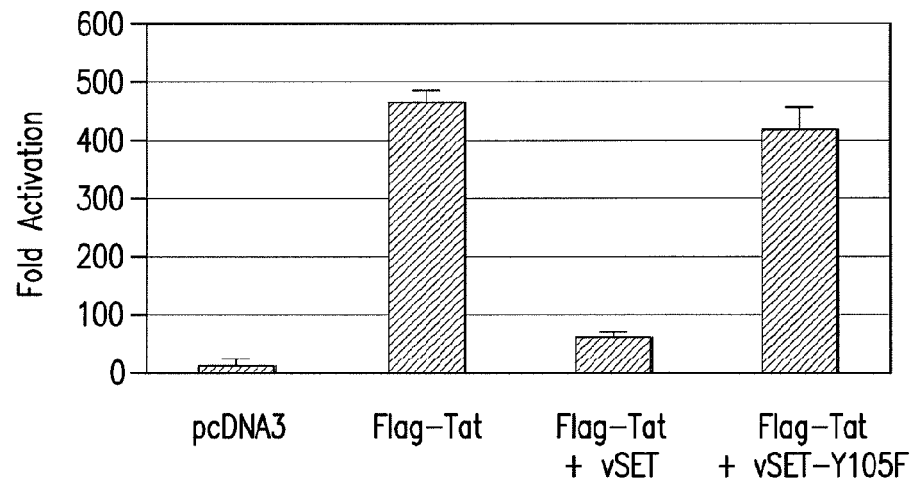
Figure 4D:
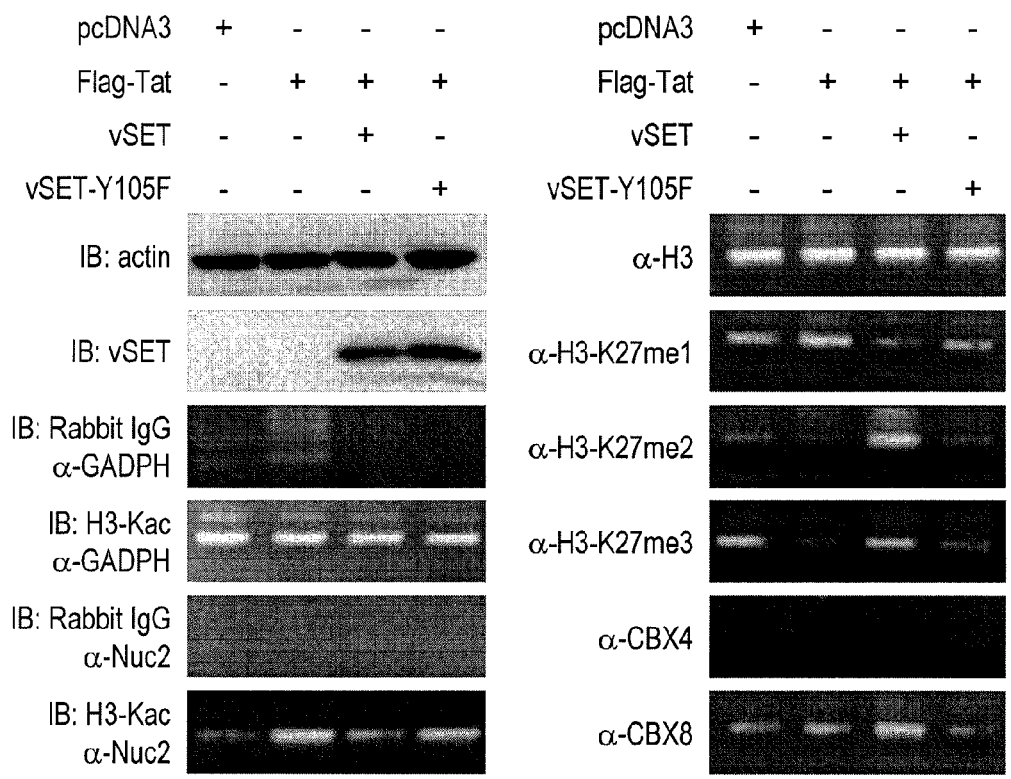

Histone H3-K27 methylation is catalyzed by the EZH2/PRC2 complex and recruits the PRC1 complex in eukaryotes leading to gene silencing (Cao and Zhang; Czermin et al.; Muller et al.; Cao et al.; Kuzmichev et al.). To determine whether vSET gene transcription repression is due to its H3-K27 methylation activity, Tat-mediated HIV LTR-luciferase activation and chromatin immunoprecipitation (ChIP) analyses were performed on the HIV LTR promoter in Hela TZM cells transfected with Flag-tagged Tat and vSET. As shown in FIG. 4c, Tat-mediated LTR activation was reduced by more than 90% upon expression of vSET but not its inactive mutant Y105F. An enhanced acetylation on H3 was observed at Nuc2 where the LTR promoter is localized but not at housekeeping gene GAPDH site when cells are transfected only with HIV Tat. These effects by vSET coincide with a marked increase of H3-K27me2 and to a lesser extent H3-K27me3 (FIG. 4d). Conversely, H3-K27me1 was somewhat decreased upon vSET expression, which is consistent with the observation of vSET treatment of the EZH2 knocked-down Hela cells (FIG. 3b-d).

Figure 4E:
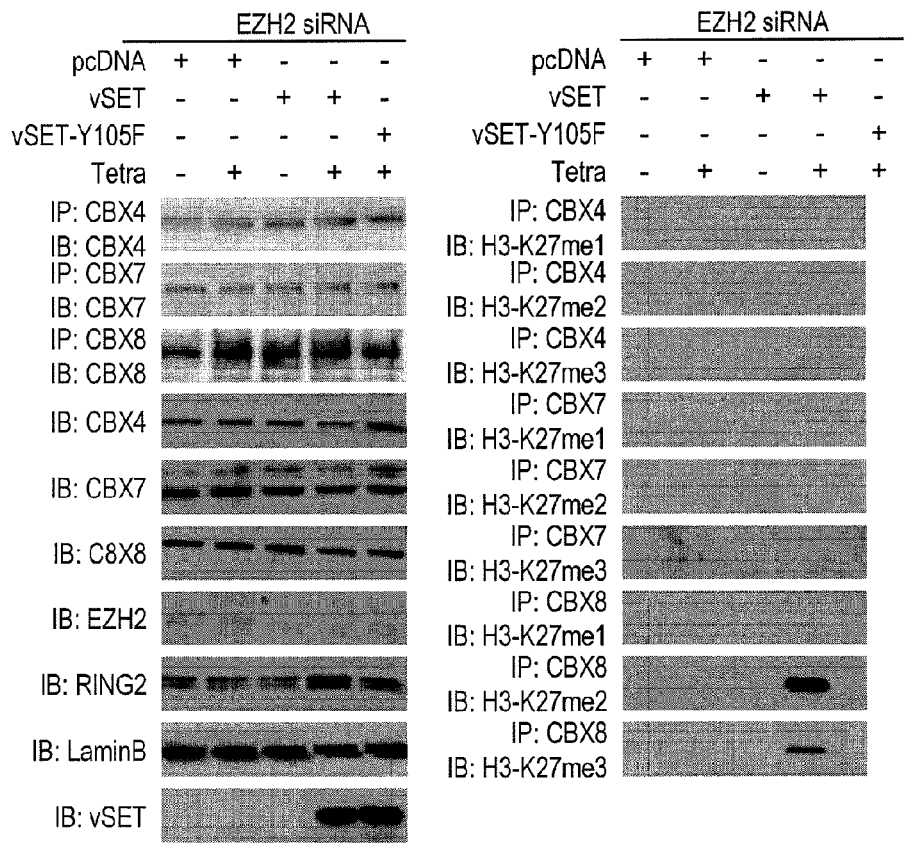
Figures 6A, 6B:
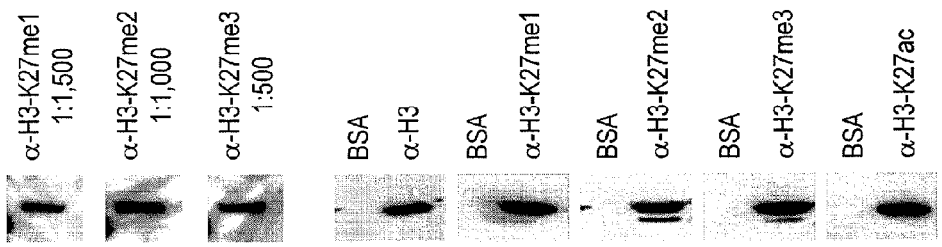
FIGS. 6a-6f show effects of vSET histone H3-K27 methylation on transcription repression. a, Optimization of concentration of histone H3-K27 mono-, and di- and tri-methylation specific antibodies to be used in Western blot analysis. b, Western blot analyses of various H3 modification-specific antibodies using native H3 isolated from calf thymus (Roche). c, Western blot analyses of association of the Polycomb group repression complexes 1 and 2 (PRC1 and PRC2) proteins with histone H3-K27 of different modifications upon induction of stably transfected vSET in HeLa cells. Lamin B was used as control. d, e, vSET repression of Tat-mediated transcription of a HIV LTR-luciferase reporter gene in transfected 293T cells, or HeLa cells, respectively, in a dose dependent manner. The error bars represent the standard deviation of triplicate assays. f, tetracycline induction of vSET in the HeLa cells with and without EZH2 knockdown by siRNA.
Figure 6C:
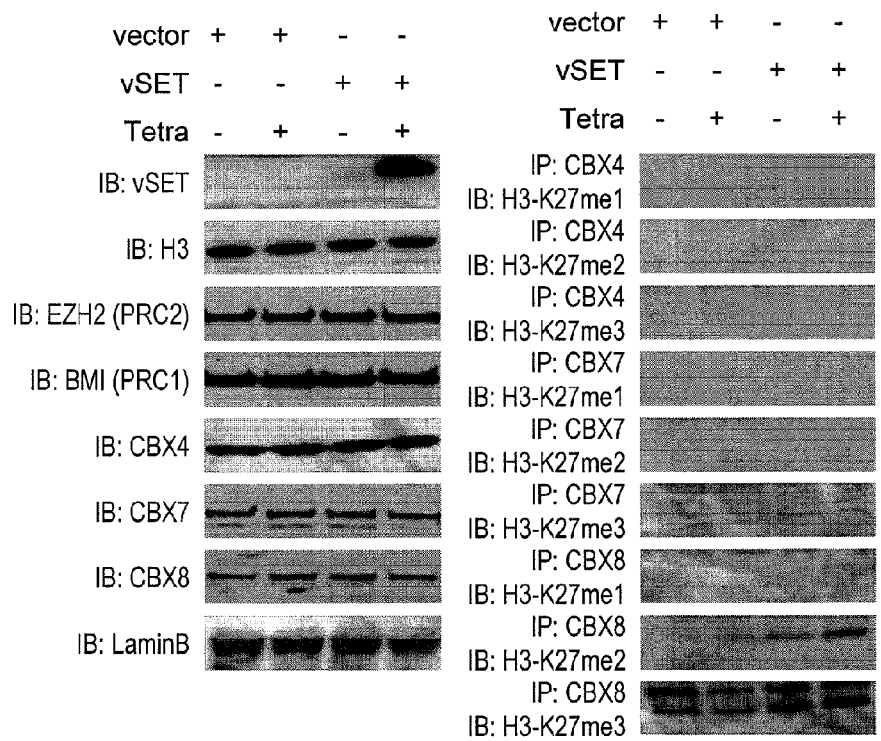
Figure 6D:
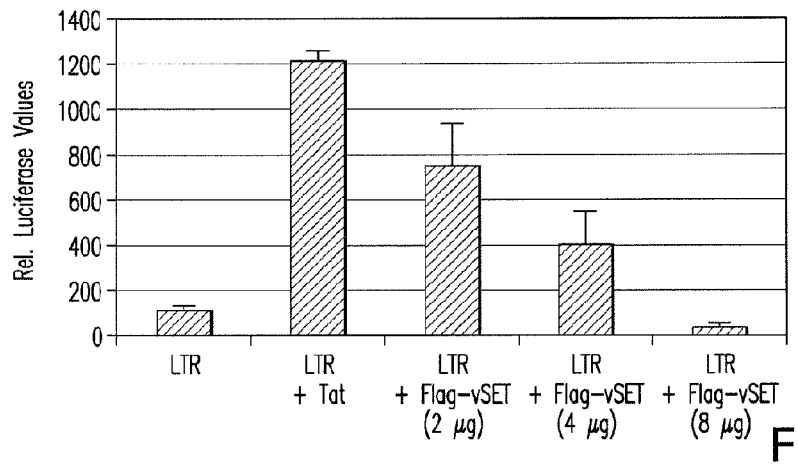
Figure 6E:
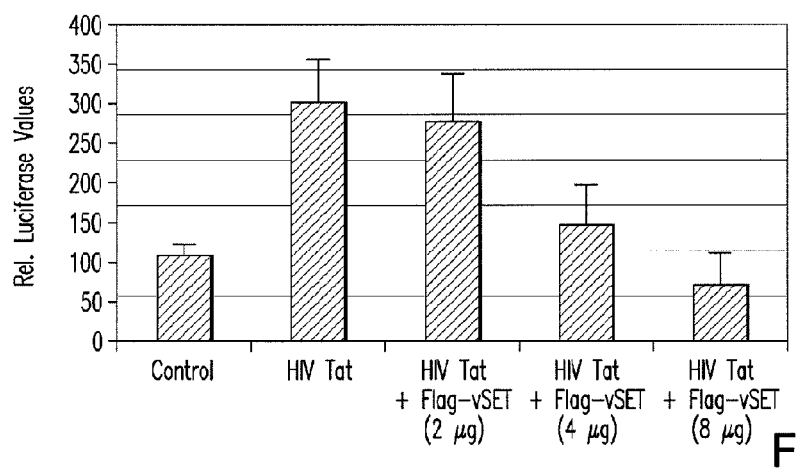

To determine the biological consequence of H3-K27 methylation by vSET, Polycomb group protein occupation at the H3-K27 site was examined upon tetracycline-induction of vSET in the EZH2 knocked-down Hela cells. It was observed that while their protein levels are not altered, vSET induction enhanced occupation of the PRC1 complex protein CBX8, but not CBX4 and CBX7, or the PRC2 RING2 at H3-K27me2 and H3-K27me3 sites (FIG. 4e). This methylation-dependent CBX8/H3-K27me2 association is likely facilitated by the methyl-lysine binding chromodomain of CBX8 (Min et al., Genes Dev 17:1823-1828 (2003)). This vSET-induced CBX8/H3-K27me2 association was also seen in ChIP on Nuc2 of the HIV LTR promoter (FIG. 4d), as well as in the regular Hela cells transfected with vSET (FIG. 6c). Taken together, these results confirm that vSET induces gene silencing via its H3-K27 methylation activity, and facilitates the consequent PRC1 complex CBX8 recruitment to chromatin site of H3-K27 methylation enhanced by vSET.

vSET Modulates Polycomb Target Genes

Figure 4F:
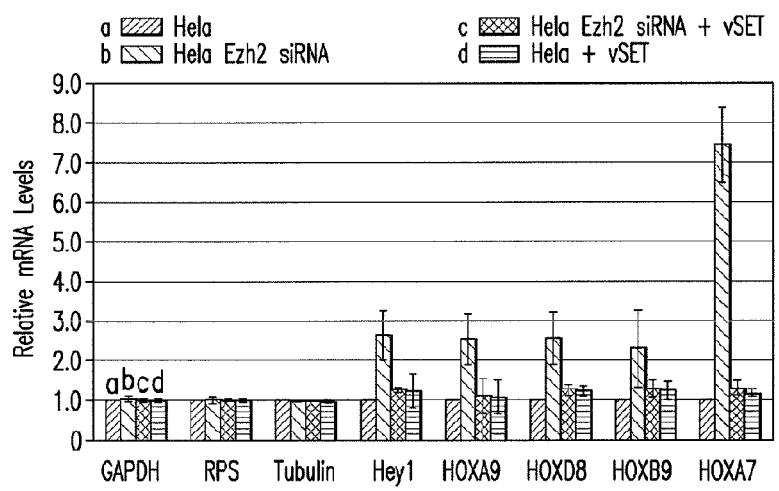
Figure 4G:
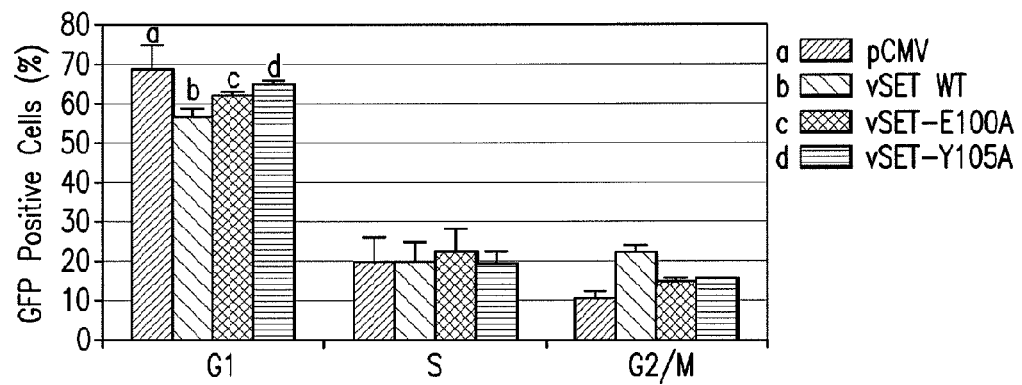
Figure 4H:
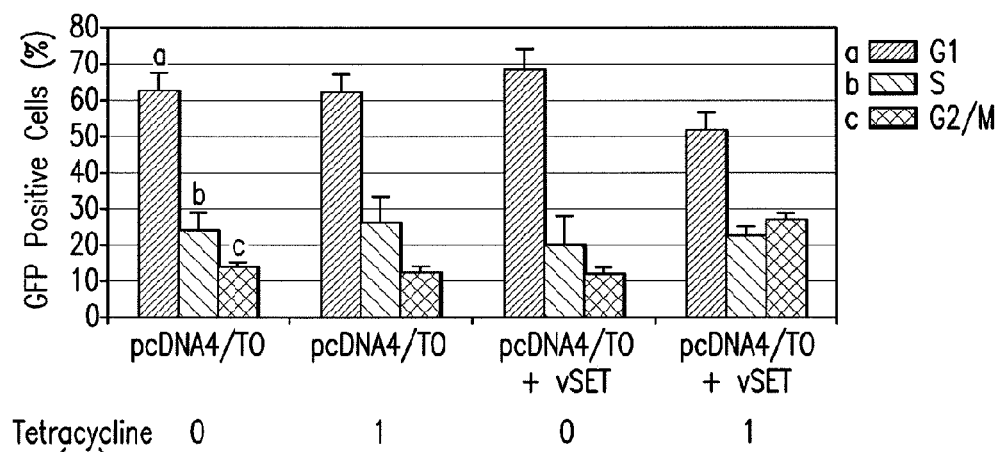
Figure 4I:
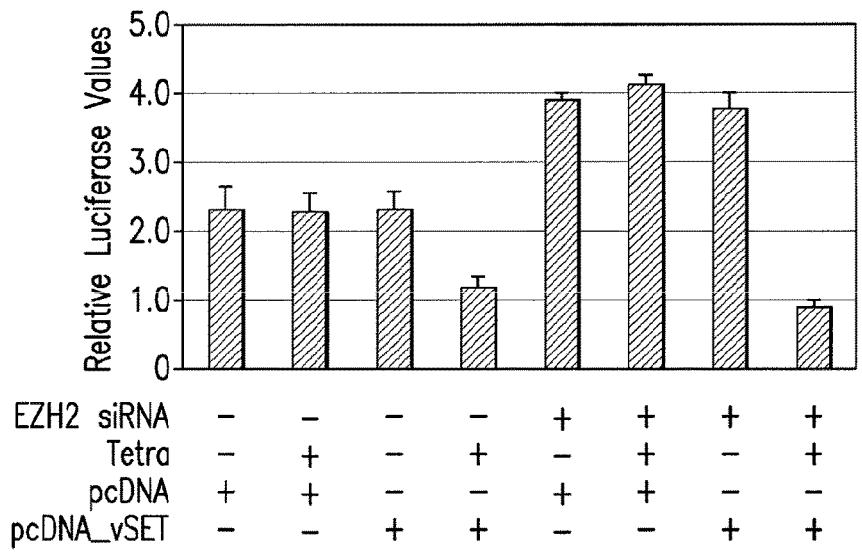
Figure 4J:
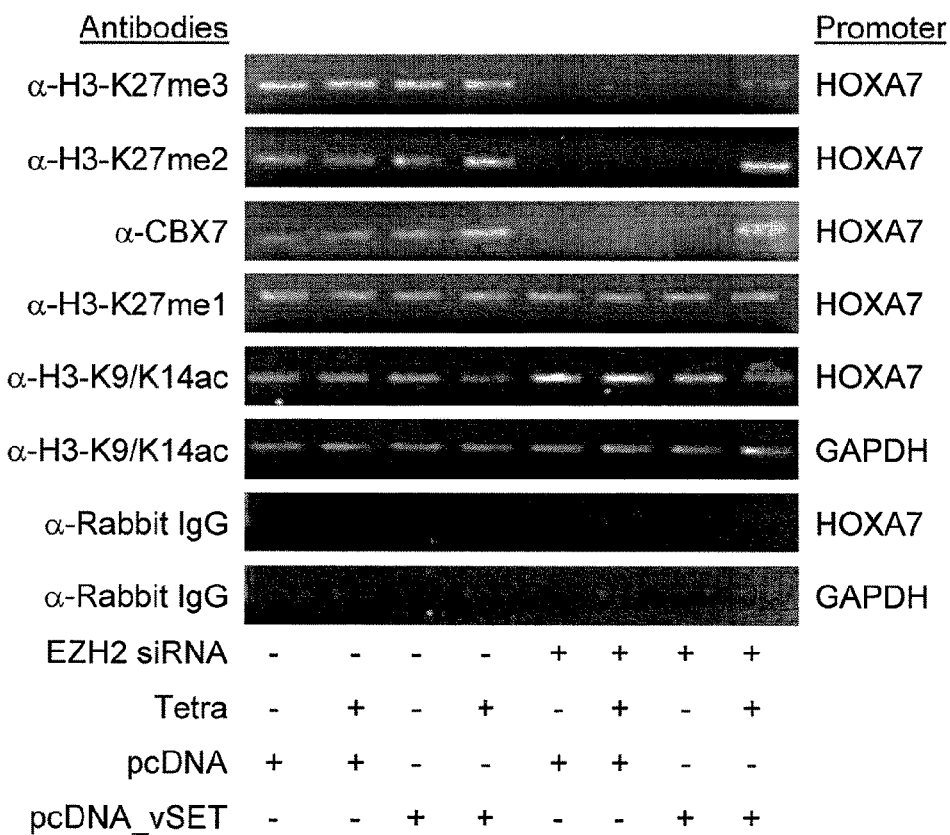
Figure 6F:
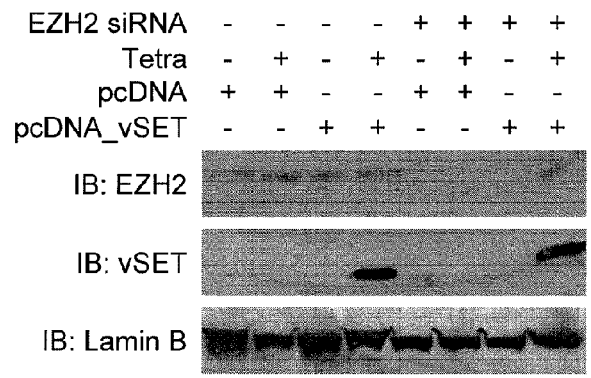

Whether vSET methylation activity can modulate Polycomb target genes was determined using a quantitative RT-PCR assay (Bracken et al.). The analysis was performed in Hela cells on five representative Polycomb target genes HOXA7, HOXA9, HOXB9, HOXD8, and Hey1; and three general housekeeping genes GAPDH, RPS, and tubulin. While the effect on the three housekeeping genes was negligible, EZH2 knockdown by siRNA resulted in a ~2.5-fold increase in transcription of HOXA9, HOXB9, HOXD8 and Hey1, and a striking 7.5-fold increase in HOXA7 expression (FIG. 4f). The enhancement of the Polycomb target genes' expression was reversed upon tetracycline-induced expression of vSET to a level at or slightly higher than that of the control cells. Moreover, vSET induction in the regular Hela cells does not cause any significant change in the expression level of all five HOX genes as compared to the controls.

vSET transcription repression was characterized on the HOXA7 promoter in luciferase gene expression and chromatin immunoprecipitation (ChIP) assays. Upon induction vSET effectively represses the luciferase expression at the HOXA7 promoter in both EZH2 siRNA treated and regular Hela cells (FIG. 4i, and FIG. 6F). the ChIP analysis confirmed that vSET specifically di- and tri-methylates H3-K27 at the HOXA7 promoter, which recruits CBX8 of the PRC1 resulting in gene repression (FIG. 4j). Similar results were obtained in the characterization of vSET transcription repression of Tat-dependent HIV LTR-luciferase reporter gene at the nucleosome Nuc2 where the HIV LTR promoter is localized in the Hela TZM cells transfected with Tat and vSET (see FIGS. 4c and 4d). These results establish that vSET can modulate transcription of Polycomb target genes through its H3-K27 methylation activity.

vSET Causes Cell Accumulation at G2/M Phase

The effect of vSET expression on the normal cell cycle was examined. Flow cytometric analysis indicated that vSET caused cell accumulation at the G2/M phase in transiently transfected NIH-3T3 cells, whereas active-site mutants E100A and Y105A had less or nearly no effect (FIG. 4g). The vSET effect on G2/M cell cycle arrest was confirmed in the study using the HeLa cells that were stably co-transfected with vSET in a tetracycline-controlled pcDNA4/TO expression vector and an Us9-GFP encoding plasmid (FIG. 4h). Collectively, the data indicate that vSET H3-K27 methylation activity results in the recruitment of the Polycomb group protein complexes and modulation of their target genes, leading to transcription repression and accumulation of cells at the G2/M phase.

vSET-Like Proteins are Universally Encoded by *Chlorella* Viruses

Figure 5A:
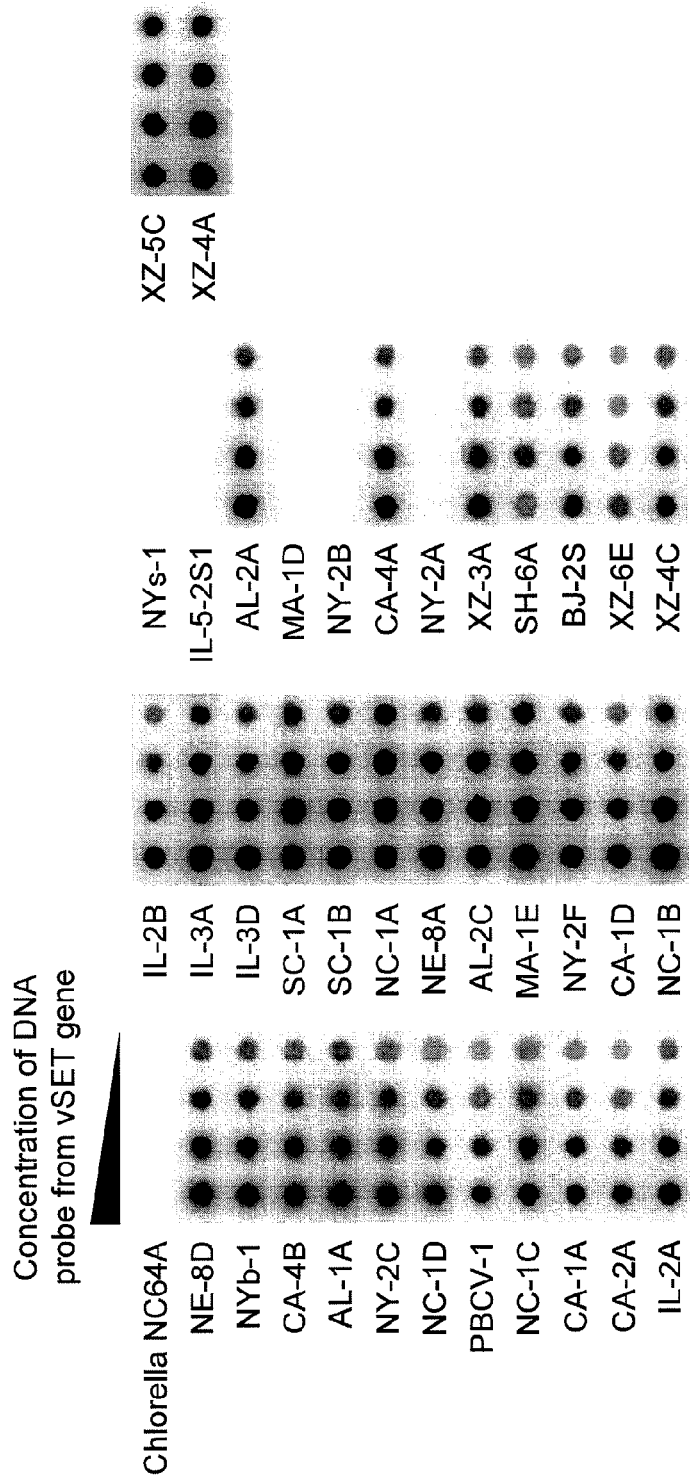
FIGS. 5a-5d show HKMT activity of SET proteins from chlorella viruses. a, Southern dot blot analysis of 37 chlorella viruses confirmed the presence of a vset-like gene in 32 viruses. vset-like genes from 3 of the 5 viruses that did not exhibit positive hybridization signals, i.e. NY-2A, NY-2B and MA-1D were detected using low stringency Southern hybridization. b, Sequence alignment of vSET and SET proteins from chlorella viruses NY2-A, NY-2B and MA-1D. Positions of α helices and β strands in the vSET sequence are shown as indicated. Residues absolutely conserved among all known SET proteins are indicated by a (●) above the residues. Residues in the three viral SET proteins that differ from vSET are also shown. Residues of vSET at the dimer interface are underlined. The NLS sequence in PBCV-1 is boxed. c, Methylation activity of the SET proteins from viruses NY2A, NY-2B and MA-1D measured with H3 peptides using $^{14}$C-methyl-SAM. d, HMT activity of the viral SET proteins using wild-type H3 (residues 1-57) versus the K27R mutant. The fluorogram shows that NY-2A, NY-2B and MA-1D SET proteins methylate wild-type H3 but not the K27R mutant. H3 modified by vSET served as a control.
Figures 5B, 5C:
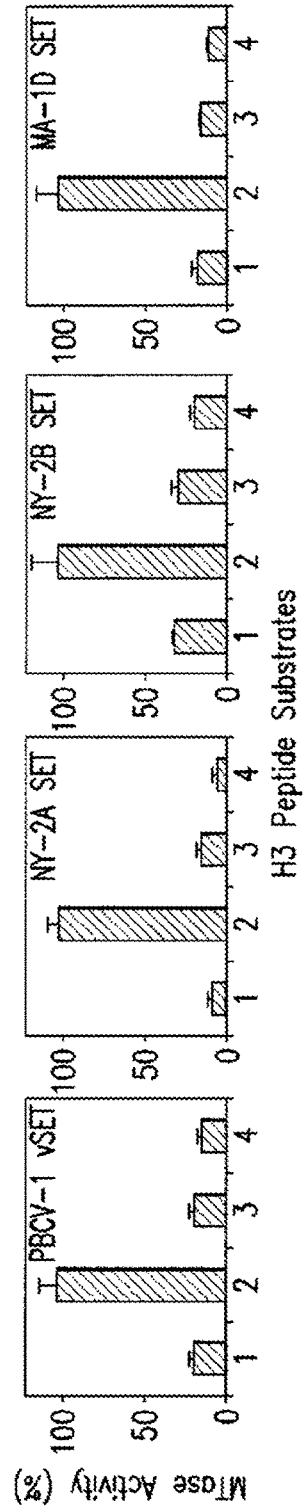

To determine if vSET is functionally unique or universal in the *chlorella* viruses, genomic DNA from 36 other *chlorella* viruses was hybridized with a vset gene probe. Thirty-one of these viruses hybridized to the probe (FIG. 5a). The probe did not hybridize to DNA from 5 viruses or the host DNA. However, a vset gene was identified in 3 of these 5 viruses using low stringency Southern hybridization. The vSET proteins from these three viruses, NY-2A, NY-2B and MA-1D, have 85% amino acid identity to PBCV-1 vSET, including the conserved active-site residues in the SET domain family (FIG. 5b).

Figure 5D:
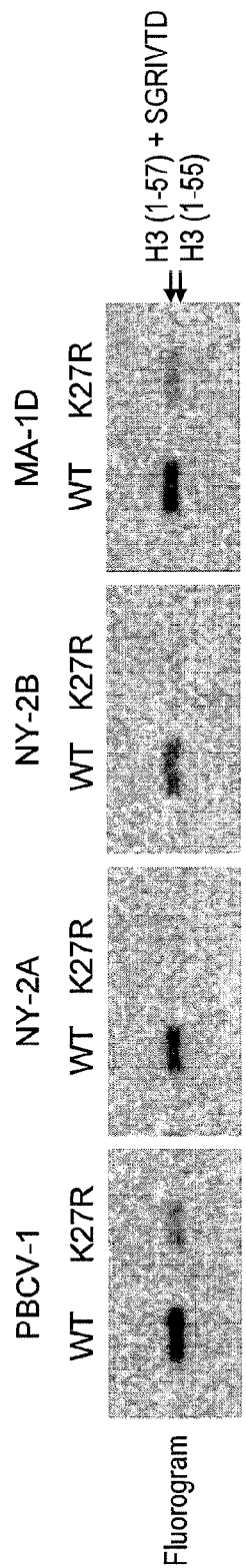

Using core histones H2A, H2B, H3 and H4 as substrates, it was established that the SET proteins from these 3 viruses selectively methylate H3 (data not shown). Like vSET, these viral SET proteins only methylated a H3 peptide containing residues 15-30 but not a peptide containing H3 residues 1-20 (FIG. 5c). They showed little methyltransferase activity if the H3 peptide was previously di-methylated at K27 or phosphorylated at S28, suggesting a preferred methylation site at H3-K27. The selective methylation at H3-K27 was confirmed using GST-histone H3 (residues 1-57), in which these viral SET proteins had robust methylation activity on wild-type H3 but little or diminished activity on the K27R mutant (FIG. 5d). Collectively, these results establish that SET proteins from the *chlorella* viruses possess selective H3-K27 methylation activity, and suggest that vSET function in host chromatin modification and transcription repression is conserved among the *chlorella* viruses.

Discussion

Histone modifications provide epigenetic control of gene transcription on the chromatin. Viruses recruit host cellular proteins to either integrate their genomes into host chromatin or to facilitate viral transcription and replication (You et al., Wu et al., Ghosh et al., Don et al., supra). Here, it has been shown for the first time that viruses take control of the host transcription machinery via direct modifications of chromatin. This study reveals that vSET is packaged in the PBCV-1 virion and is capable of directly methylating host H3-K27, an important epigenetic modification in eukaryotes that has been functionally linked to Hox gene silencing, X-inactivation and stem cell pluripotency (Czermin et al., Muller et al., Cao et al., Kuzmichev et al., Cao & Zhang, Plath et al., Boggs et al., Bernstein et al., Boyer et al., Lee et al., supra). The results establish that vSET H3-K27 methylation promotes the recruitment of the PRC1 complex via a molecular interaction between the chromodomain of CBX8 and di- and/or tri-methylated H3-K27 that results in transcriptional repression and cell accumulation at the G2/M phase in cell cycle in the continuously dividing cells (Czermin et al., Muller et al., Cao et al., Kuzmichev et al., Cao & Zhang, Plath et al., Boggs et al., Bernstein et al., Boyer et al., Lee et al., supra). These results support a hypothesis that the role of vSET is to globally shut off host gene transcription in infected *chlorella* cells. The demonstration that a protein with H3-K27 methylation activity is encoded by all the *chlorella* viruses provides additional support for this hypothesis.

Several unusual features of vSET emerged from this study and highlight its efficiency as a viral transcription suppressor. First, vSET is packaged in mature virions, and becomes active immediately after viral infection and host cell entry. Second, vSET has a nuclear localization signal that allows transport to the host nucleus. Third, vSET has high substrate specificity for H3-K27 but not H3-K9 sites even though the two sites have similar amino acid sequences (Qian et al., supra). Fourth, the literature on functional significance of H3-K27 mono-methylation remains elusive, and how H3-K27 di- and/or tri-methylation is functionally linked to development and gene silencing is also equivocal (Cao & Zhang, supra). vSET can be an important tool for resolving questions about the role of H3-K27 methylation states on cellular processes as the ability of vSET to produce mono-, di-, and tri-methylations at this site can be controlled by amino acid substitutions in vSET at its active site (Qian et al., supra). Finally, vSET is the smallest SET domain HKMTase; vSET lacks the pre- and post-SET motifs present in mammalian SET HKMTases (Qian & Zhou, supra). In contrast to mammalian monomeric SET HKMTases, vSET functions as a dimer. It may be postulated that in the quest for efficiency, the dimeric form of this viral SET HKMTase may have evolved to allow methylation of histone pairs within one nucleosome or in neighboring nucleosomes, thereby increasing its efficiency in modifying host chromatin.

The presence of a viral encoded and virion packaged enzyme with direct chromatin-modifying properties may provide advantages to the *chlorella* viruses. For example, it would eliminate the need for using cellular proteins as functional mediators and therefore, the expression of such cellular proteins would not be a factor. It would also increase the efficiency with which the virus modifies cellular processes before host resistance responses are activated. Collectively, our findings suggest a unique and powerful mechanism by which some viruses commandeer host transcription machinery through direct modifications of histones and thereby govern a wide range of chromatin-mediated cellular processes.

Example 2: Expression of vSET in a Host Cell Results in Global Gene Silencing that Triggers Cell Cycle Arrest or Apoptosis Transgenic *Arabidopsis* plants were generated containing a beta-estradiol inducible vSET expression vector as well as another transferred pSGCOR1 vector, which carries a promoter from the *Arabidopsis* ubiquitin gene driving the expression of a fusion protein that is made up of GAL4, estrogen receptor, and VP-16. The latter transferred DNA confers hygromycin resistance to the plant. The transformed plants live normally, exhibiting a wild-type phenotype prior to the induction of vSET expression (FIG. 8a, control). About 10 days after beta-estradiol (10 µM) induced expression of vSET, the plants exhibited massive cell death as shown in FIG. 8b-c.

Example 3: Transcriptional Silencing of Human Disease Causing Genes by vSET

The ability of vSET to repress Gal4-based promoter system and HOXA7 promoter at the transcriptional level through its histone H3 lysine 27 methylation (see, Example 1, supra; and Mujtaba et al., Nat Cell Biol., 10(9):1114-22 (2008)), prompted the examination of whether and how vSET could silence genes that have been implicated in etiology and pathogenesis of human diseases such as androgen receptor (AR) in prostate cancer (Heinlein et al., Endocr Rev, 25(2):276-308 (2004)) as well as selected genes in other diseases as listed in Table 1.

Methods

In this study, human HeLa cells were co-transfected with selected gene promoters (Table 1) in tandem with the luciferase gene with either an empty vector (pcDNA4TO) as a control or with vSET cloned into the pcDNA4TO vector. vSET expression was induced after treating the HeLa cells with 5 µg of tetracycline. Target gene expression was then assessed by measuring luciferase values using a dual luciferase assay kit (Promega, Cat# E1510), and normalized with the *renilla* luciferase value.

Results

As shown in FIG. 1, co-transfection of pcNDA4TO expression and luciferase reporter gene has little effects on target gene expression. However, upon expression induced tetracycline, vSET can effectively repress transcription of AR (prostate cancer) (Heinlein et al., Endocr Rev, 25(2): 276-308 (2004)), HOXA7 (ovarian cancer) (Naora et al., Proc Natl Acad Sci USA, 98(26):15209-14 (2001)). HOXA9 (blood disorders) (Kroon et al., EMBO J, 20(3):350-61 (2001)), HOXC8 (prostate cancer) (Waltregny et al., Prostate, 50(3):162-9 (2002)), RAR (leukemia) (Zelent et al., Oncogene, 20(49):7186-203 (2001)), cyclin D (cancers) (Knudsen et al., Oncogene, 25(11):1620-8 (2006)), and NK-κB (inflammation) (Christman et al., Intensive Care Med, 24(11):1131-8 (1998)) See also Table 1. Moreover, vSET H3K27 methylation activity also resulted in an increased transcription of E. cadherin (Sawada et al., Cancer Res, 68(7):2329-39 (2008)) and M50/beta catenin (Lin et al., Proc Natl Acad Sci USA, 97(8):4262-6 (2000)) (see FIG. 1), suggesting that these genes are suppressed by other regulatory genes, which transcription is likely targeted by vSET. Taken together, this study demonstrates that vSET can effectively suppress transcription of genes implicated in human diseases through its activity of methylation of histone H3 lysine 27 at chromatin sites where the target genes are resided.

As such, vSET can be developed into a target gene specific silencing technology. This will be achieved by fusing vSET to a DNA binding protein domain that recognizes specifically the promoter sequence of a given target gene, or to a histone binding protein domain that interacts with a core histone H3 or H4 carrying a distinct post-translational amino acid modification at the target gene site. Furthermore, vSET will be engineered to possess regulatory capacity via mutagenesis of amino acid residues at the enzyme active site or methyl donor (S-adenosyl-methionine) co-factor binding site, in which a novel small-molecule chemical compound could be developed to control the enzymatic activity of vSET in a spatial and temporal manner. As such, a vSET-based target specific gene silencing technology could be developed into novel disease therapies for various human diseases by silencing disease-causing gene expression.

TABLE 1

Genes Selected for vSET Transcriptional Silencing Analysis

| Gene | Human Disease | References |
| --- | --- | --- |
| Androgen Receptor | Prostate cancer | Heinlein et al., End. Reviews. 2004, 25 (2): 276-308 |
| HOXA2 | Developmental disorder | Chatonnet et al., Neural Development 2007, 2: 19 |

TABLE 1-continued

Genes Selected for vSET Transcriptional Silencing Analysis

| Gene | Human Disease | References |
|---|---|---|
| HOXA5 | Breast cancer | Raman *et al., Nature* 405, 974-978 |
| HOXA7 | Ovarian cancer | Naora *et al., PNAS*, 2001, 18; 98: 15209-14 |
| HOXC8 | Prostate cancer | Waltregny *et al., Prostate*, 2002, 15; 50: 162-9. |
| HOXA9 | Blood disorders | Kroon *et al., The EMBO J.* 2001, 20; 350-361 |
| Retinoic Acid receptor (RAR) | Leukemia | Zelent *et al., Oncogene*, 2001, 20; 49: 7186-03 |
| Retinoic Acid X receptor (RXR) | Cancers | Altucci *et al., Nature Rev Drug Dis.* 2007, 6; 793-810 |
| Cyclin D | Cancers | Knudsen *et al., Oncogene*, 2006, 25; 1620-1628 |
| E Cadherin | Breast and ovarian cancers | Sawada *et al., Cancer Research*, 2008, 68; 2329 |
| NF-κB | Inflammation | Christman *et al., Inten. Care Med.* 1998, 24: 1131-1138 |
| M50/Beta Catenin | Cancers | Lin *et al., PNAS*, 2000, 97: 4262-4266 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A pharmaceutical composition for human administration comprising a purified fusion protein comprising a *Chlorella* virus SET domain of a viral histone lysine methyltransferase protein (vSET), or of a vSET-like protein, fused to a protein that binds to a target gene, in a pharmaceutically acceptable carrier.

2. The composition of claim 1, wherein the vSET protein comprises an amino acid sequence defined by SEQ ID NO:2.

3. The composition of claim 1, wherein the purified fusion protein further comprises a nuclear localization signal.

4. The composition of claim 3, wherein the nuclear localization signal is a Lys-Arg-Met-Arg (KRMR) (SEQ ID NO:3) peptide.

5. The composition of claim 1, wherein the *Chlorella* virus SET domain of a viral histone lysine methyltransferase protein (vSET) or of a vSET-like protein is covalently linked to the protein that binds to a target gene.

6. The composition of claim 1, wherein the target gene is a cytokine, an oncogenic gene, a homeodomain gene, a transcription factor, a receptor, a regulatory gene, a cell cycle regulating protein or a viral replication gene.

7. The composition of claim 6, wherein the target gene is a cytokine selected from the group consisting of TNF-α, TGF-β, IFN-γ, IL-2, IL-10 and any combination thereof.

8. The composition of claim 6, wherein the target gene is an oncogenic gene selected from the group consisting of MDM2, Src tyrosine kinases, Ras kinases, receptor tyrosine kinases, epidermal growth factor receptors (EGFRs), platelet-derived growth factor receptors (PDGFRs), vascular endothelial growth factor receptors (VEGFRs) and any combination thereof.

9. The composition of claim 6, wherein the target gene is a homeodomain gene selected from the group consisting of HOXA2, HOXA5, HOXA7, HOXA9, HOXB9, HOXC6, HOXC8, HOXD8, Hey1 and any combination thereof.

10. The composition of claim 6, wherein the target gene is a transcription factor selected from the group consisting of myc, NF-κB and combination thereof.

11. The composition of claim 6, wherein the target gene is a receptor selected from the group consisting of an androgen receptor, a retinoic acid receptor (RAR), a retinoic acid x receptor (RXR) and any combination thereof.

12. The composition of claim 6, wherein the target gene is a regulatory gene selected from the group consisting of E cadherin, M50/Beta-catenin and combination thereof.

13. The composition of claim 6, wherein the target gene is a cell cycle regulating protein selected from the group consisting of any cyclin D proteins and any combination thereof.

14. The composition of claim 6, wherein the target gene is a HIV transcriptional activator protein tat.

15. The composition of claim 1, wherein the protein that binds to a target gene is selected from the group consisting of transcription factors, enhancer proteins, suppressor proteins, the DNA binding domains thereof and any combination thereof.

16. The composition of claim 15, wherein the protein that binds to a target gene is selected from the group consisting of NF-kB, HOXC6, HOXC8, the DNA binding domains thereof and any combination thereof.

17. A pharmaceutical composition for selectively inhibiting transcriptional expression of a target gene in a subject in need thereof, comprising:
   i) a purified fusion protein comprising:
      a) a *Chlorella* virus SET domain of a viral histone lysine methyltransferase protein (vSET) or of a vSET-like protein, covalently linked to
      b) a protein that binds to the target gene, and
   ii) a pharmaceutically acceptable carrier.

* * * * *

SEQUENCE LISTING

```
<160> NUMBER OF SEQ ID NOS: 54

<210> SEQ ID NO 1
<211> LENGTH: 360
<212> TYPE: DNA
<213> ORGANISM: Paramecium bursaria Chlorella virus 1

<400> SEQUENCE: 1
ttaattttgt gttaatctag gtctagacaa ccagtagtca tcgccataac ttatcgttat      60
ttcttcaccg atggctattg gttttatggt gaatatccgc atgcgcttga gacctgctgt     120
cagttcatgt ctagcgttag ggtctttgct atggttaaaa attgcaccaa aaccaagagc     180
cattgcagac atattctttc tcgaaaacaa ataatcttca agggcggtcc cccaatcatc     240
attatggcgc actatacaca aacattcttc aacaagttct cccttctcga aagattttct     300
cgcaaataca ccatatccac ccaatgggga ttttttcacg atgactctgt cattaaacat     360

<210> SEQ ID NO 2
<211> LENGTH: 119
<212> TYPE: PRT
<213> ORGANISM: Paramecium bursaria Chlorella virus 1

<400> SEQUENCE: 2

Met Phe Asn Asp Arg Val Ile Val Lys Lys Ser Pro Leu Gly Gly Tyr
1               5                   10                  15

Gly Val Phe Ala Arg Lys Ser Phe Glu Lys Gly Glu Leu Val Glu Glu
            20                  25                  30

Cys Leu Cys Ile Val Arg His Asn Asp Asp Trp Gly Thr Ala Leu Glu
        35                  40                  45

Asp Tyr Leu Phe Ser Arg Lys Asn Met Ser Ala Met Ala Leu Gly Phe
    50                  55                  60

Gly Ala Ile Phe Asn His Ser Lys Asp Pro Asn Ala Arg His Glu Leu
65                  70                  75                  80

Thr Ala Gly Leu Lys Arg Met Arg Ile Phe Thr Ile Lys Pro Ile Ala
                85                  90                  95

Ile Gly Glu Glu Ile Thr Ile Ser Tyr Gly Asp Asp Tyr Trp Leu Ser
            100                 105                 110
```

Arg Pro Arg Leu Thr Gln Asn
        115

<210> SEQ ID NO 3
<211> LENGTH: 4
<212> TYPE: PRT
<213> ORGANISM: Unknown
<220> FEATURE:
<223> OTHER INFORMATION: nuclear localization signal

<400> SEQUENCE: 3

Lys Arg Met Arg
1

<210> SEQ ID NO 4
<211> LENGTH: 4
<212> TYPE: PRT
<213> ORGANISM: Unknown
<220> FEATURE:
<223> OTHER INFORMATION: mutated PBCV-1 vSET nuclear localization signal

<400> SEQUENCE: 4

Ala Ala Met Ala
1

<210> SEQ ID NO 5
<211> LENGTH: 4
<212> TYPE: PRT
<213> ORGANISM: Unknown
<220> FEATURE:
<223> OTHER INFORMATION: nuclear localization signal

<400> SEQUENCE: 5

Pro Arg Ile Val
1

<210> SEQ ID NO 6
<211> LENGTH: 4
<212> TYPE: PRT
<213> ORGANISM: Unknown
<220> FEATURE:
<223> OTHER INFORMATION: nuclear localization signal

<400> SEQUENCE: 6

Lys Arg Pro Arg
1

<210> SEQ ID NO 7
<211> LENGTH: 4
<212> TYPE: PRT
<213> ORGANISM: Unknown
<220> FEATURE:
<223> OTHER INFORMATION: nuclear localization signal

<400> SEQUENCE: 7

Arg Arg Pro Arg
1

<210> SEQ ID NO 8
<211> LENGTH: 15
<212> TYPE: DNA
<213> ORGANISM: Artificial sequence
<220> FEATURE:
<223> OTHER INFORMATION: oligonucleotide primer

<400> SEQUENCE: 8
atggcccgca ccaag                                                    15

<210> SEQ ID NO 9
<211> LENGTH: 15
<212> TYPE: DNA
<213> ORGANISM: Artificial sequence
<220> FEATURE:
<223> OTHER INFORMATION: oligonucleotide primer

<400> SEQUENCE: 9
ttaggcgcgc tcgcc         15

<210> SEQ ID NO 10
<211> LENGTH: 135
<212> TYPE: PRT
<213> ORGANISM: Chlorella NC64A

<400> SEQUENCE: 10

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
                20                  25                  30

Gly Gly Val Lys Lys Pro His Arg Tyr Arg Pro Gly Thr Val Ala Leu
            35                  40                  45

Arg Glu Ile Arg Lys Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Leu Ala Leu Gln Glu Ala Ala
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 11
<211> LENGTH: 135
<212> TYPE: PRT
<213> ORGANISM: Homo sapiens

<400> SEQUENCE: 11

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 12
<211> LENGTH: 135
<212> TYPE: PRT
<213> ORGANISM: Mus musculus

<400> SEQUENCE: 12

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 13
<211> LENGTH: 135
<212> TYPE: PRT
<213> ORGANISM: Xenopus laevis

<400> SEQUENCE: 13

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Ser
                85                  90                  95

Glu Ala Tyr Leu Val Gly Leu Phe Glu Asp Thr Asn Leu Cys Gly Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 14
<211> LENGTH: 135
<212> TYPE: PRT
<213> ORGANISM: Caenorhabditis elegans

```
<400> SEQUENCE: 14

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Ser
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Arg
50                  55                  60

Ala Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Ala
                85                  90                  95

Glu Ala Tyr Leu Val Gly Leu Phe Glu Asp Thr Asn Leu Cys Ala Ile
                100                 105                 110

His Ala Lys Arg Val Thr Ile Met Pro Lys Asp Ile Gln Leu Ala Arg
            115                 120                 125

Arg Ile Arg Gly Glu Arg Ala
130                 135

<210> SEQ ID NO 15
<211> LENGTH: 134
<212> TYPE: PRT
<213> ORGANISM: Chlamydomonas reinhardtii

<400> SEQUENCE: 15

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Thr Pro Ala Thr Gly
                20                  25                  30

Gly Val Lys Lys Pro His Arg Tyr Arg Pro Gly Thr Val Ala Leu Arg
            35                  40                  45

Glu Ile Arg Lys Tyr Gln Lys Ser Thr Glu Leu Leu Ile Arg Lys Leu
50                  55                  60

Pro Phe Gln Arg Leu Val Arg Glu Ile Ala Gln Asp Phe Lys Thr Asp
65                  70                  75                  80

Leu Arg Phe Gln Ser Gln Ala Val Val Ala Leu Gln Glu Ala Ala Glu
                85                  90                  95

Ala Tyr Leu Val Gly Leu Phe Glu Asp Thr Asn Leu Cys Ala Ile Thr
                100                 105                 110

Ala Lys Arg Val Thr Ile Met Pro Lys Asp Ile Gln Leu Ala Arg Arg
            115                 120                 125

Ile Arg Gly Glu Arg Ala
130

<210> SEQ ID NO 16
<211> LENGTH: 119
<212> TYPE: PRT
<213> ORGANISM: Paramecium Bursaria Chlorella virus NY2A

<400> SEQUENCE: 16

Met Tyr Asn Asp Arg Val Ile Val Lys Lys Ser Pro Leu Gly Gly Tyr
1               5                   10                  15

Gly Val Phe Ala Lys Lys Ser Phe Asp Lys Gly Asp Leu Ile Glu Asp
                20                  25                  30
```

Cys Leu Cys Val Val Arg Tyr Asn Asp Asp Trp Gly Ser Ala Leu Glu
            35                  40                  45

Asp Tyr Leu Phe Ser Arg Lys Asn Met Ser Ala Met Pro Leu Gly Phe
    50                  55                  60

Gly Ala Ile Phe Asn His Gly Lys Asp Pro Asn Ala Arg His Glu Leu
65                  70                  75                  80

Thr Ser Gly Leu Lys Ser Met Arg Ile Phe Ala Thr Arg Pro Ile Ile
                85                  90                  95

Ala Gly Glu Glu Ile Thr Ile Asn Tyr Gly Asn Ala Tyr Trp Leu Ser
                100                 105                 110

Arg Ala Arg Leu Lys Met Asn
        115

<210> SEQ ID NO 17
<211> LENGTH: 119
<212> TYPE: PRT
<213> ORGANISM: Paramecium Bursaria Chlorella virus NY2B

<400> SEQUENCE: 17

Met Phe Asn Asp Arg Val Val Ile Lys Lys Ser Pro Leu Gly Gly Tyr
1               5                   10                  15

Gly Val Phe Ala Lys Lys Ser Phe Asp Lys Gly Asp Leu Ile Glu Glu
            20                  25                  30

Cys Leu Cys Ile Val Arg His Asn Asp Asp Trp Gly Ile Ala Leu Glu
            35                  40                  45

Asp Tyr Leu Phe Ser Arg Lys Asn Met Ser Ala Met Pro Leu Gly Phe
    50                  55                  60

Gly Ala Ile Phe Asn His Gly Lys Asp Pro Asn Ala Arg His Glu Leu
65                  70                  75                  80

Thr Ser Gly Leu Lys Gln Met Arg Val Phe Ala Ile Lys Ser Ile Ile
                85                  90                  95

Pro Gly Glu Glu Ile Lys Ile Ser Tyr Gly Asp Asp Tyr Trp Lys Ser
                100                 105                 110

Arg Pro Arg Leu Thr Gln Asn
        115

<210> SEQ ID NO 18
<211> LENGTH: 119
<212> TYPE: PRT
<213> ORGANISM: Paramecium Bursaria Chlorella virus MA1D

<400> SEQUENCE: 18

Met Phe Asn Asp Arg Val Val Lys Lys Ser Pro Leu Gly Gly Tyr
1               5                   10                  15

Gly Val Phe Ala Lys Lys Ser Phe Asp Lys Gly Asp Leu Ile Glu Glu
            20                  25                  30

Cys Leu Cys Ile Val Arg His Asn Asp Asp Trp Gly Ile Ala Leu Glu
            35                  40                  45

Asp Tyr Leu Phe Ser Arg Lys Asn Met Ser Ala Met Pro Leu Gly Phe
    50                  55                  60

Gly Ala Ile Phe Asn His Gly Lys Asp Pro Asn Ala Arg His Glu Leu
65                  70                  75                  80

Thr Ser Gly Leu Lys Gln Met Arg Val Phe Ala Ile Lys Ser Ile Ile
                85                  90                  95

Pro Gly Glu Glu Ile Lys Ile Ser Tyr Gly Asp Asp Tyr Trp Lys Ser
                100                 105                 110

-continued

Arg Pro Arg Leu Thr Gln Asn
        115

<210> SEQ ID NO 19
<211> LENGTH: 20
<212> TYPE: PRT
<213> ORGANISM: Unknown
<220> FEATURE:
<223> OTHER INFORMATION: Amino acids 1-20 of H3 polypeptide

<400> SEQUENCE: 19

Ala Arg Thr Lys Gln Thr Ala Arg Lys Ser Thr Gly Gly Lys Ala Pro
1               5                   10                  15

Arg Lys Gln Leu
        20

<210> SEQ ID NO 20
<211> LENGTH: 16
<212> TYPE: PRT
<213> ORGANISM: Unknown
<220> FEATURE:
<223> OTHER INFORMATION: Amino acids 15-30 of H3 polypeptide

<400> SEQUENCE: 20

Ala Pro Arg Lys Gln Leu Ala Thr Lys Ala Ala Arg Lys Ser Ala Pro
1               5                   10                  15

<210> SEQ ID NO 21
<211> LENGTH: 16
<212> TYPE: PRT
<213> ORGANISM: Unknown
<220> FEATURE:
<223> OTHER INFORMATION: Amino acids 15-30 of H3 polypeptide
<220> FEATURE:
<221> NAME/KEY: UNSURE
<222> LOCATION: (13)..(13)
<223> OTHER INFORMATION: di-methylated

<400> SEQUENCE: 21

Ala Pro Arg Lys Gln Leu Ala Thr Lys Ala Ala Arg Lys Ser Ala Pro
1               5                   10                  15

<210> SEQ ID NO 22
<211> LENGTH: 16
<212> TYPE: PRT
<213> ORGANISM: Unknown
<220> FEATURE:
<223> OTHER INFORMATION: Amino acids 15-30 of H3 polypeptide
<220> FEATURE:
<221> NAME/KEY: UNSURE
<222> LOCATION: (14)..(14)
<223> OTHER INFORMATION: Phosphorylation

<400> SEQUENCE: 22

Ala Pro Arg Lys Gln Leu Ala Thr Lys Ala Ala Arg Lys Ser Ala Pro
1               5                   10                  15

<210> SEQ ID NO 23
<211> LENGTH: 57
<212> TYPE: PRT
<213> ORGANISM: Unknown
<220> FEATURE:
<223> OTHER INFORMATION: Amino acids 1-57 of Paramecium bursaria
      Chlorella NC64A H3 polypeptide

<400> SEQUENCE: 23

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser
    50                  55

<210> SEQ ID NO 24
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with 5R mutation

<400> SEQUENCE: 24

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Arg Ser Ala Pro Ser Thr
            20                  25                  30

Gly Gly Val Arg Arg Pro His Arg Tyr Arg Pro Gly Thr Val Ala Leu
        35                  40                  45

Arg Glu Ile Arg Arg Tyr Gln Lys Ser
    50                  55

<210> SEQ ID NO 25
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K27/K4R/K9R mutation

<400> SEQUENCE: 25

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser
    50                  55

<210> SEQ ID NO 26
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K27/4R mutation

<400> SEQUENCE: 26

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Lys Ser Ala Pro Ser Thr
            20                  25                  30

Gly Gly Val Arg Arg Pro His Arg Tyr Arg Pro Gly Thr Val Ala Leu
        35                  40                  45

Arg Glu Ile Arg Arg Tyr Gln Lys Ser
    50                  55

<210> SEQ ID NO 27
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K36/4R mutation

<400> SEQUENCE: 27

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Arg Ser Ala Pro Ser Thr
            20                  25                  30

Gly Gly Val Lys Arg Pro His Arg Tyr Arg Pro Gly Thr Val Ala Leu
        35                  40                  45

Arg Glu Ile Arg Arg Tyr Gln Lys Ser
    50                  55

<210> SEQ ID NO 28
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K37/4R mutation

<400> SEQUENCE: 28

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Arg Ser Ala Pro Ser Thr
            20                  25                  30

Gly Gly Val Arg Lys Pro His Arg Tyr Arg Pro Gly Thr Val Ala Leu
        35                  40                  45

Arg Glu Ile Arg Arg Tyr Gln Lys Ser
    50                  55

<210> SEQ ID NO 29
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K27R/K36R mutation

<400> SEQUENCE: 29

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Arg Ser Ala Pro Ser Thr
            20                  25                  30

Gly Gly Val Arg Lys Pro His Arg Tyr Arg Pro Gly Thr Val Ala Leu
        35                  40                  45

Arg Glu Ile Arg Arg Tyr Gln Lys Ser
    50                  55

<210> SEQ ID NO 30
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K36/K37/3R mutation

<400> SEQUENCE: 30

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Arg Ser Ala Pro Ser Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser
    50                  55

<210> SEQ ID NO 31
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K27/K37/3R mutation

<400> SEQUENCE: 31

Ala Arg Thr Arg Gln Thr Ala Arg Arg Ser Thr Gly Gly Lys Ala Pro
1               5                   10                  15

Arg Lys Gln Leu Ala Thr Lys Ala Ala Arg Lys Ser Ala Pro Ser Thr
                20                  25                  30

Gly Gly Val Arg Lys Pro His Arg Tyr Arg Pro Gly Thr Val Ala Leu
            35                  40                  45

Arg Glu Ile Arg Arg Tyr Gln Lys Ser
    50                  55

<210> SEQ ID NO 32
<211> LENGTH: 57
<212> TYPE: PRT
<213> ORGANISM: Unknown
<220> FEATURE:
<223> OTHER INFORMATION: amino acids 1-57 of Paramecium bursaria
      Chlorella NC64A H3 polypeptide with K27R mutation

<400> SEQUENCE: 32

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Arg Ser Ala Pro Ser Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser
    50                  55

<210> SEQ ID NO 33
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 33
gaggacggau ucccaauaau u                                          21

<210> SEQ ID NO 34
<211> LENGTH: 21
<212> TYPE: RNA
<213> ORGANISM: Artificial sequence
<220> FEATURE:
<223> OTHER INFORMATION: Synthetic oligonucleotide

```
<400> SEQUENCE: 34
gcugaagccu caauguuuau u                                              21

<210> SEQ ID NO 35
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 35
uaacggugau cacaggauau u                                              21

<210> SEQ ID NO 36
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 36
gcaaauucuc ggugucaaau u                                              21

<210> SEQ ID NO 37
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 37
uuauugggaa gccguccucu u                                              21

<210> SEQ ID NO 38
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 38
uaaacauuga ggcuucagcu u                                              21

<210> SEQ ID NO 39
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 39
uauccuguga ucaccguuau u                                              21

<210> SEQ ID NO 40
<211> LENGTH: 21
<212> TYPE: RNA
<213> ORGANISM: Artificial sequence
<220> FEATURE:
<223> OTHER INFORMATION: Synthetic oligonucleotide

<400> SEQUENCE: 40
uuugacaccg agaauuugcu u                                              21

<210> SEQ ID NO 41
<211> LENGTH: 19
```

```
<212> TYPE: DNA
<213> ORGANISM: Artificial sequence
<220> FEATURE:
<223> OTHER INFORMATION: Synthetic oligonucleotide

<400> SEQUENCE: 41
caaaatgccg agccgactt                                              19

<210> SEQ ID NO 42
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 42
tagccggacg caaaggg                                                17

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
cagccaactg gcttcatgcg                                             20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
cactcgtctt ttgctcggtc                                             20

<210> SEQ ID NO 45
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 45
aactggctgc acgctcggt                                              19

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tcacattact ctttgccctg                                             20

<210> SEQ ID NO 47
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 47
```
ggatacgata acttacagag ac                    22

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
tagagtttgg aagcgactgt                       20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
tgcaacacca actgcttagc                       20

<210> SEQ ID NO 50
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 50
ggcatggact gtggtcatga g                     21

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
gaggcgccgc tgtagtta                         18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
ggcgtgcgcg tcaaagta                         18

<210> SEQ ID NO 53
<211> LENGTH: 7
<212> TYPE: PRT
<213> ORGANISM: Artificial Sequence
<220> FEATURE:
<223> OTHER INFORMATION: Vector Sequence

<400> SEQUENCE: 53

Ser Gly Arg Ile Val Thr Asp
1               5

<210> SEQ ID NO 54
<211> LENGTH: 4
<212> TYPE: PRT

```
<213> ORGANISM: Artificial Sequence
<220> FEATURE:
<223> OTHER INFORMATION: Nuclear Localization Signal

<400> SEQUENCE: 54

Arg Arg Ile Val
1
```